(12) United States Patent
Nagaraja et al.

(10) Patent No.: US 7,449,310 B2
(45) Date of Patent: Nov. 11, 2008

(54) **RECOMBINANT *FUSOBACTERIUM NECROPHORUM* LEUKOTOXIN VACCINE AND PREPARATION THEREOF**

(75) Inventors: Tiruvoor G. Nagaraja, Manhattah, KS (US); George C. Stewart, Manhattan, KS (US); Sanjeev K. Narayanan, Irving, TX (US); Muckatira M. Chengappa, Manhattan, KS (US)

(73) Assignee: Kansas State University Research Foundation, Manhattan, KS (US)

( * ) Notice: Subject to any disclaimer, the term of this patent is extended or adjusted under 35 U.S.C. 154(b) by 196 days.

(21) Appl. No.: 10/647,057

(22) Filed: Aug. 22, 2003

(65) Prior Publication Data

US 2004/0047871 A1 Mar. 11, 2004

Related U.S. Application Data

(60) Division of application No. 09/841,786, filed on Apr. 24, 2001, now Pat. No. 6,669,940, which is a continuation-in-part of application No. 09/558,257, filed on Apr. 25, 2000, now abandoned.

(51) Int. Cl.
*C12P 21/04* (2006.01)
*C12P 21/06* (2006.01)
*C07H 21/04* (2006.01)
*C12N 1/20* (2006.01)
*A61K 39/02* (2006.01)

(52) U.S. Cl. ............... 435/69.7; 435/320.1; 435/252.3; 435/71.1; 435/69.3; 435/69.1; 530/350; 536/23.7; 536/23.1; 424/236.1; 424/234.1; 424/184.1

(58) Field of Classification Search .............. 435/69.1, 435/69.3, 71.1, 252.3, 320.1, 69.7; 530/350; 536/23.5, 23.7, 23.1; 424/236.1, 234.1, 192.1, 424/185.1, 184.1, 176.1
See application file for complete search history.

(56) References Cited

U.S. PATENT DOCUMENTS

| 4,152,415 A | 5/1979 | Harris et al. |
| 4,203,968 A | 5/1980 | Harris et al. |
| 4,919,929 A | 4/1990 | Beck |
| 5,455,034 A | 10/1995 | Nagaraja et al. |
| 5,804,190 A * | 9/1998 | Struck et al. ............. 424/190.1 |
| 5,861,162 A | 1/1999 | Nagaraja et al. |

OTHER PUBLICATIONS

Bowie et al. Science, vol. 247: 1990; p. 1306; p. 1308.*
Houghten et al. (Vaccines, 1986, Edited by Fred Brown: Cold Spring Harbor Laboratory).*
Abe et al.; *Fusobacterium necrophorum* infection in mice as a model for the study of liver abscess formation and induction of immunity; (1976); Infect. Immun. 13:1473-1478.

Abe et al.; Immunization of Mice Against *Fusobacterium necrophorum* infection by Parenteral or Oral Administration of Vaccine; (1978); Am J. Vet Res.; 39:115-118.

Berson, G.; Silver staining of proteins in polyacrylamide gels: increased sensitivity by a blue toning, (1983); Anal. Biochem. 134:230-234.

Cameron et al.; Antibody Response to and Immunity Induced by Corynebacterium Pyogenes Vaccine; Onderstepoort J. vet. Res. 43 (3), 97-104 (1976).

Cameron et al.; Failure to INduce in Rabbits Effective Immunity to a Mixed Infection of *Fusobacterium mectrophorum* and *Corynebacterium pyogenes* with a Combined Bacterin; Onderstepoort J. vet. Res. 44 (4), 253-256 (1977).

Conion et al.; Evaluation of experimentally induced *Fusobacterium necrophorum* infections in mice; (1977); Infect. Immun. 15:510-517.

Coyle-Dennis, et al.; Biological and Biochemical Characteristics of *Fusobacterium necrophorum* Leukocidin; Am. J. Vet Res. (1978); 39:1790-1793.

Coyle-Dennis, et al.; Correlation between leukocidin production and virulence of two isolates of *Fusobacterium necrophorum*. (1979) Am. J. Vet Res. 40:274-276.

Emery et al.; Generation of immunity against *Fusobacterium necrophorum* in mice inoculated with extracts containing leukocidin; (1986) Vet. Microbiol. 12:255-268.

Emery et al.; Biochemical and functional properties of a leukocidin produced by several strains of *Fusobacterium necrophorum*; (1984); Aus. Vet. J.; 61:382-385.

Emery et al.; Studies on the purification of the leukocidin of *Fusobacterium necrophorum* and its neutralization by specific antisera; (1986); Vet. Microbiol. 11:357-372.

Emery et al.; Virulence determinants of *Fusobacterium necrophorum* and their prophylactic potential in animals. In: Stewart, D.J., Peterson, J.E., McKern, N.M. and Emery D.L. (eds), Foot rot in reminants. Proceedings of a workshop, Melbourne (CSIRO Division of animal health, Australian wool corporation, Australia), 267-274.

(Continued)

*Primary Examiner*—Robert B Mondesi
*Assistant Examiner*—Padma V Baskar
(74) *Attorney, Agent, or Firm*—Tracey S. Truitt

(57) ABSTRACT

The *F. necrophorum* gene expressing leukotoxin was sequenced and cloned. The leukotoxin open reading frame (lktA) is part of a multi-gene operon containing 9,726 bp, and encoding a protein containing 3,241 amino acids with an overall molecular weight of 335,956 daltons. The protein encoded by the gene was truncated into five polypeptides having overlapping regions by truncating the full length gene into five different sections and amplifying, expressing, and recovering the protein encoded by each of these sections. Additionally, a region upstream of the gene was sequenced and the polypeptide encoded by that nucleotide sequence was purified and isolated. These polypeptides along with the full length protein are then tested to determine their immunogenicity and protective immunity in comparison to the efficacy of immunization conferred by inactivated native leukotoxin in *F. necrophorum* culture supernatant.

21 Claims, 13 Drawing Sheets

OTHER PUBLICATIONS

Garcia et al.; Biological characterization of *Fusobacterium necrophorum* cell fractions in preparation for toxin and immunization studies; (1975); Infect. Immun. 11:606-616.
Garcia, et al; Results of a preliminary trial with sphaerophorus necrophorus toxoids to control liver abscesses in feedlot cattle; Can. J. Comp. Med., (1974) 38:222-226.
Garcia, et al.; Intraperitoneal immunization against necrobacillosis in experimental animals; (1978) Can. J. Comp. Med. 42:121-127.
Hunter, et al.; Failure of an Actinomyces Pyogenes Vaccine to Protect Sheep Against an Intravenous Challenge; Onderstepoort J. vet. Res., 57, 239-241 (1990).
Langworth, B.F.; *Fusobacterium necrophorum*; (1977); Bacteriol. Rev. 41:373-390.
Nagaraja et al.; Liver abscesses in feedlot cattle: A review; (1998); J. Anim. Sci. 76:287-298.
Narayanan et al.; Cloning, sequencing and expression of the leukotoxin gene from *Fusobacterium necrophorum*; Infect. and Immun.; Spet. 2001, vol. 69, No. 9, p. 5447-5455.
Rowe et al.; Microtechnique for most-probable-number analysis; (1977); Appl. Environ. Microbiol. 33:675-680.
Saginala et al.; Effect of *Fusobacterium necrophorum* leukotoxoid vaccine on susceptibility to experimentally induced liver abscesses in cattle; (1997); J. Anim. Sci. 75:1160-1166.
Saginala et al.; The serum neutralizing antibody response in cattle to *Fusobacterium necrophorum* leukotoxoid and possible protection against experimentally induced hepatic abscesses; (1996a); Vet. Res. Comm., 20:493-504.
Saginala et al.; The serum neutralizing antibody response and protection against experimentally induced liver abscesses in steers vaccinated with *Fusobacterium necrophorum*; (1996b); Am. J. Vet. Res. 57:483-488.
Smith, et al.; Pathogenicity of *Fusobacterium necrophorum* strains from man and animals; (1993); Epidemiol. Infect. 110:499-506.
Smith, et al.; Necrobacillus and immunity in mice; (1989); Epidemiol. Infect. 103:211-215.
Tan et al.; Selective anumeration of *Fusobacterium necrophorum* from the bovine rumen; (1994b); Appl. Environ. Microbiol. 60:1387-1389.
Tan et al.; *Fusobacterium necrophorum* infections: virulence factors, pathogenic mechanism and control measures; (1996); Vet. Res. Comm. 20:113-140.
Tan et al.; Biological and biochemical characterization of *Fusobacterium necrophorum* leukotoxin; (1994c); Am. J. Vet. Res. 55:515.
Tan et al.; Purification and quantification of *Fusobacterium necrophorum* leukotoxin using monoclonal antibodies; (1994d); Vet. Microbiol 42:121-133.
Warner et al.; Passive Hemmagglutination Test for Determining the Immune Response of Rabbits to Sphaerophorus necrophorus of bovine hepatic abscess origin; (1974); Am. J. Vet. Res. 35:551-554.
Nagaraja et al., The Compendium, Sep. 1996, pp. S230-241.
Nagaraja et al., The Compendium, Oct. 1996; pp. S264-273.
Gillis et al.; Evaluation of Primary Rumen Epithelial Cell Culture Technique in Sheep, Fed. Proc. 11:LB210.
Zeller, U.P., Toxin Production by Corynebacterium pyogenes, toxin storage, antibody titres in blood and milk serum samples from healthy and mastitic cows. CAB Accession No. 792236623 (1978).
Vladutiu, O. et al.; Immunization of swine against corynebacterial osteoarthropathy; CAB Accession No. 792237402; (1975/1976).
Funk et al.; Identification and partial characterization of an actinomyces pyogenes hemolysin; Vet. Micro., 50 (1996) 129-142.
Morrison et al.; Identification of Actinomyces (Corynebacterium) pyogenes with the API 20 Strep System, J. Clinical Microbiology; vol. 26, No. 9, 1988, pp. 1865-1866.
Narayanan et al.; Biochemical and biological characterizations and ribotyping of actinomyces pyogenes and actinomyces pyogenes-like organisms from liver abscesses in cattle; Veterinary Microbiology, 61 (1998), pp. 289-303.
Billington, et al.; Molecular characterization of the pore-forming toxin, pyolysin, a major virulence determinant; Veterinary Microbiology, 82 (2001), 261-274.
Billington, et al. The Aracanobacterium (Actinomyces) pyogenes Hemolysin, Pyolysin, is a novel member of the Thiol-Activated Cytolysin Family; J. Bacteriology, Oct. 1997, p. 6100-6106.
Billington, et al.; Tyiol-activated cytolysins: structure, function and role in pathogenesis; FEMS Microbiology Letters 182 (2000, 197-205.
Jost et al.; An arcanobacterium (actinomyces) pyogenes mutant deficient in production of the pore-forming cytolysin pyolysin has reduced virulence; Infection and Immunity, Apr. 1999, p. 1723-1728.
Koromyslov, G.F., Vaccine for prevention of necrobacteriosis in cattle; SU 1835295 (Abstract).
Manual of Clinical Microbiology (3rd Ed.), *Culture Media*, p. 975.
Quinones, Sowerby, C.A., New vaccine against bovine keratoconjunctivitis; CAB Accession No. 792237182 (1978).
Testing of Combined Fusobacterium Necrophorum Leukotoxoid and Actinomyces Pyogenes Vaccine for Prevention of Liver Abscesses, undated.

* cited by examiner

SEQUENCE LISTING

<160> NUMBER OF SEQ ID NOS: 15

<210> SEQ ID NO 1
<211> LENGTH: 3241
<212> TYPE: PRT
<213> ORGANISM: Fusobacterium necrophorum

```
<400> SEQUENCE: 1

Met Ser Gly Ile Lys Asn Asn Val Gln Arg Thr Arg Lys Arg Ile Ser
1               5                   10                  15

Asp Ser Lys Lys Val Leu Met Ile Leu Gly Leu Leu Ile Asn Thr Met
            20                  25                  30

Thr Val Arg Ala Asn Asp Thr Ile Thr Ala Thr Glu Asn Phe Gly Thr
        35                  40                  45

Lys Ile Glu Lys Lys Asp Asn Val Tyr Asp Ile Thr Thr Asn Lys Ile
50                  55                  60

Gln Gly Glu Asn Ala Phe Asn Ser Phe Asn Arg Phe Ala Leu Thr Glu
65                  70                  75                  80

Asn Asn Ile Ala Asn Leu Tyr Phe Gly Glu Lys Asn Ser Thr Gly Val
                85                  90                  95

Asn Asn Leu Phe Asn Phe Val Asn Gly Lys Ile Glu Val Asp Gly Ile
            100                 105                 110

Ile Asn Gly Ile Arg Glu Asn Lys Ile Gly Gly Asn Leu Tyr Phe Leu
        115                 120                 125

Ser Ser Glu Gly Met Ala Val Gly Lys Asn Gly Val Ile Asn Ala Gly
130                 135                 140

Ser Phe His Ser Ile Ile Pro Lys Gln Asp Asp Phe Lys Lys Ala Leu
145                 150                 155                 160

Glu Glu Ala Lys His Gly Lys Val Phe Asn Gly Ile Ile Pro Val Asp
                165                 170                 175

Gly Lys Val Lys Ile Pro Leu Asn Pro Asn Gly Ser Ile Thr Val Glu
            180                 185                 190

Gly Lys Ile Asn Ala Val Glu Gly Ile Gly Leu Tyr Ala Ala Asp Ile
        195                 200                 205

Arg Leu Lys Asp Thr Ala Ile Leu Lys Thr Gly Ile Thr Asp Phe Lys
210                 215                 220

Asn Leu Val Asn Ile Ser Asp Arg Ile Asn Ser Gly Leu Thr Gly Asp
225                 230                 235                 240

Leu Lys Ala Thr Lys Thr Lys Ser Gly Asp Ile Ile Leu Ser Ala His
                245                 250                 255

Ile Asp Ser Pro Gln Lys Ala Met Gly Lys Asn Ser Thr Val Gly Lys
            260                 265                 270

Arg Ile Glu Glu Tyr Val Lys Gly Asn Thr Lys Ala Asn Ile Glu Ser
        275                 280                 285

Asp Ala Val Leu Glu Ala Asp Gly Asn Ile Lys Ile Ser Ala Lys Ala
290                 295                 300

Thr Asn Gly Arg Phe Ile Lys Lys Glu Gly Lys Glu Thr Tyr Asn
305                 310                 315                 320

Thr Pro Leu Ser Leu Ser Asp Val Glu Ala Ser Val Arg Val Asn Lys
                325                 330                 335

Gly Lys Val Ile Gly Lys Asn Val Asp Ile Thr Ala Glu Ala Lys Asn
            340                 345                 350

Phe Tyr Asp Ala Thr Leu Val Thr Lys Leu Ala Lys His Ser Phe Ser
        355                 360                 365

Phe Val Thr Gly Ser Ile Ser Pro Ile Asn Leu Asn Gly Phe Leu Gly
370                 375                 380

Leu Leu Thr Ser Lys Ser Ser Val Val Ile Gly Lys Asp Ala Lys Val
385                 390                 395                 400

Glu Ala Thr Glu Gly Lys Ala Asn Ile His Ser Tyr Ser Gly Val Arg
```

-continued

```
            405                 410                 415
Ala Thr Met Gly Ala Ala Thr Ser Pro Leu Lys Ile Thr Asn Leu Tyr
            420                 425                 430
Leu Glu Lys Ala Asn Gly Lys Leu Leu Ser Ile Gly Ala Gly Tyr Ile
            435                 440                 445
Ser Ala Lys Ser Asn Ser Asn Val Thr Ile Glu Gly Glu Val Lys Ser
            450                 455                 460
Lys Gly Arg Ala Asp Ile Thr Ser Lys Ser Glu Asn Thr Ile Asp Ala
465                 470                 475                 480
Ser Val Ser Val Gly Thr Met Arg Asp Ser Asn Lys Val Ala Leu Ser
            485                 490                 495
Val Leu Val Thr Glu Gly Glu Asn Lys Ser Ser Val Lys Ile Ala Lys
            500                 505                 510
Gly Ala Lys Val Glu Ser Glu Thr Asp Asp Val Asn Val Arg Ser Glu
            515                 520                 525
Ala Ile Asn Ser Ile Arg Ala Ala Val Lys Gly Gly Leu Gly Asp Ser
            530                 535                 540
Gly Asn Gly Val Val Ala Ala Asn Ile Ser Asn Tyr Asn Ala Ser Ser
545                 550                 555                 560
Arg Ile Asp Val Asp Gly Tyr Leu His Ala Lys Lys Arg Leu Asn Val
            565                 570                 575
Glu Ala His Asn Ile Thr Lys Asn Ser Val Leu Gln Thr Gly Ser Asp
            580                 585                 590
Leu Gly Thr Ser Lys Phe Met Asn Asp His Val Tyr Glu Ser Gly His
            595                 600                 605
Leu Lys Ser Ile Leu Asp Ala Ile Lys Gln Arg Phe Gly Gly Asp Ser
            610                 615                 620
Val Asn Glu Glu Ile Lys Asn Lys Leu Thr Asn Leu Phe Ser Val Gly
625                 630                 635                 640
Val Ser Ala Thr Ile Ala Asn His Asn Asn Ser Ala Ser Val Ala Ile
            645                 650                 655
Gly Glu Ser Gly Arg Leu Ser Ser Gly Val Glu Gly Ser Asn Val Arg
            660                 665                 670
Ala Leu Asn Glu Ala Gln Asn Leu Arg Ala Thr Thr Ser Ser Gly Ser
            675                 680                 685
Val Ala Val Arg Lys Glu Glu Lys Lys Leu Ile Gly Asn Ala Ala
            690                 695                 700
Val Phe Tyr Gly Asn Tyr Lys Asn Asn Ala Ser Val Thr Ile Ala Asp
705                 710                 715                 720
His Ala Glu Leu Val Ser Glu Gly Lys Ile Asp Ile Asn Ser Glu Asn
            725                 730                 735
Lys Ile Glu Tyr Lys Asn Pro Ser Lys Met Ala Lys Ser Val Ile Asp
            740                 745                 750
Lys Leu Glu Leu Leu Lys Arg Ala Phe Gly Lys Glu Thr Lys Thr Pro
            755                 760                 765
Glu Tyr Asp Pro Lys Asp Ile Glu Ser Ile Glu Lys Leu Leu Asn Ala
            770                 775                 780
Phe Ser Glu Lys Leu Asp Gly Lys Pro Glu Leu Leu Leu Asn Gly Glu
785                 790                 795                 800
Arg Met Thr Ile Ile Leu Pro Asp Gly Thr Ser Lys Thr Gly Thr Ala
            805                 810                 815
Ile Glu Ile Ala Asn Tyr Val Gln Gly Glu Met Lys Lys Leu Glu Glu
            820                 825                 830
```

```
Lys Leu Pro Lys Gly Phe Lys Ala Phe Ser Glu Gly Leu Ser Gly Leu
        835                 840                 845

Ile Lys Glu Thr Leu Asn Phe Thr Gly Val Gly Asn Tyr Ala Asn Phe
    850                 855                 860

His Thr Phe Thr Ser Ser Gly Ala Asn Gly Glu Arg Asp Val Ser Ser
865                 870                 875                 880

Val Gly Gly Ala Val Ser Trp Val Glu Gln Glu Asn Tyr Ser Lys Val
                885                 890                 895

Ser Val Gly Lys Gly Ala Lys Leu Ala Ala Lys Lys Asp Leu Asn Ile
            900                 905                 910

Lys Ala Ile Asn Lys Ala Glu Thr Val Asn Leu Val Gly Asn Ile Gly
        915                 920                 925

Leu Ala Arg Ser Ser Thr Ser Gly Ser Ala Val Gly Gly Arg Leu Asn
        930                 935                 940

Val Gln Arg Ser Lys Asn Ser Ala Ile Val Glu Ala Lys Glu Lys Ala
945                 950                 955                 960

Glu Leu Ser Gly Glu Asn Ile Asn Ala Asp Ala Leu Asn Arg Leu Phe
                965                 970                 975

His Val Ala Gly Ser Phe Asn Gly Gly Ser Gly Gly Asn Ala Ile Asn
            980                 985                 990

Gly Met Gly Ser Tyr Ser Gly Gly Ile Ser Lys Ala Arg Val Ser Ile
        995                 1000                1005

Asp Asp Glu Ala Tyr Leu Lys Ala Asn Lys Lys Ile Ala Leu Asn
    1010                1015                1020

Ser Lys Asn Asp Thr Ser Val Trp Asn Ala Ala Gly Ser Ala Gly
    1025                1030                1035

Ile Gly Thr Lys Asn Ala Ala Val Gly Val Ala Val Ala Val Asn
    1040                1045                1050

Asp Tyr Asp Ile Ser Asn Lys Ala Ser Ile Glu Asp Asn Asp Glu
    1055                1060                1065

Gly Gln Ser Lys Tyr Asp Lys Asn Lys Asp Asp Glu Val Thr Val
    1070                1075                1080

Thr Ala Glu Ser Leu Glu Val Asp Ala Lys Thr Thr Gly Thr Ile
    1085                1090                1095

Asn Ser Ile Ser Val Ala Gly Gly Ile Asn Lys Val Gly Ser Lys
    1100                1105                1110

Pro Ser Glu Glu Lys Pro Lys Ser Glu Glu Arg Pro Glu Gly Phe
    1115                1120                1125

Phe Gly Lys Ile Gly Asn Lys Val Asp Ser Val Lys Asn Lys Ile
    1130                1135                1140

Thr Asp Ser Met Asp Ser Leu Thr Glu Lys Ile Thr Asn Tyr Ile
    1145                1150                1155

Ser Glu Gly Val Lys Lys Ala Gly Asn Leu Pro Ser Asn Val Ser
    1160                1165                1170

His Thr Pro Asp Lys Gly Pro Ser Phe Ser Leu Gly Ala Ser Gly
    1175                1180                1185

Ser Val Ser Phe Asn Asn Ile Lys Lys Glu Thr Ser Ala Val Val
    1190                1195                1200

Asp Gly Val Lys Ile Asn Leu Lys Gly Ala Asn Lys Lys Val Glu
    1205                1210                1215

Val Thr Ser Ser Asp Ser Thr Phe Val Gly Ala Trp Gly Gly Ser
    1220                1225                1230
```

-continued

Ala Ala Leu Gln Trp Asn His Ile Gly Ser Gly Asn Ser Asn Ile
1235                1240                1245

Ser Ala Gly Leu Ala Gly Ala Ala Val Asn Asn Ile Gln Ser
1250                1255                1260

Lys Thr Ser Ala Leu Val Lys Asn Ser Asp Ile Arg Asn Ala Asn
1265                1270                1275

Lys Phe Lys Val Asn Ala Leu Ser Gly Gly Thr Gln Val Ala Ala
1280                1285                1290

Gly Ala Gly Leu Glu Ala Val Lys Glu Ser Gly Gln Gly Lys
1295                1300                1305

Ser Tyr Leu Leu Gly Thr Ser Ala Ser Ile Asn Leu Val Asn Asn
1310                1315                1320

Glu Val Ser Ala Lys Ser Glu Asn Asn Thr Val Ala Gly Glu Ser
1325                1330                1335

Glu Ser Gln Lys Met Asp Val Asp Val Thr Ala Tyr Gln Ala Asp
1340                1345                1350

Thr Gln Val Thr Gly Ala Leu Asn Leu Gln Ala Gly Lys Ser Asn
1355                1360                1365

Gly Thr Val Gly Ala Thr Val Thr Val Ala Lys Leu Asn Asn Lys
1370                1375                1380

Val Asn Ala Ser Ile Ser Gly Gly Arg Tyr Thr Asn Val Asn Arg
1385                1390                1395

Ala Asp Ala Lys Ala Leu Leu Ala Thr Thr Gln Val Thr Ala Ala
1400                1405                1410

Val Thr Thr Gly Gly Thr Ile Ser Ser Gly Ala Gly Leu Gly Asn
1415                1420                1425

Tyr Gln Gly Ala Val Ser Val Asn Lys Ile Asp Asn Asp Val Glu
1430                1435                1440

Ala Ser Val Asp Lys Ser Ser Ile Glu Gly Ala Asn Glu Ile Asn
1445                1450                1455

Val Ile Ala Lys Asp Val Lys Gly Ser Ser Asp Leu Ala Lys Glu
1460                1465                1470

Tyr Gln Ala Leu Leu Asn Gly Lys Asp Lys Lys Tyr Leu Glu Asp
1475                1480                1485

Arg Gly Ile Asn Thr Thr Gly Asn Gly Tyr Tyr Thr Lys Glu Gln
1490                1495                1500

Leu Glu Lys Ala Lys Lys Lys Glu Gly Ala Val Ile Val Asn Ala
1505                1510                1515

Ala Leu Ser Val Ala Gly Thr Asp Lys Ser Ala Gly Gly Val Ala
1520                1525                1530

Ile Ala Val Asn Thr Val Lys Asn Lys Phe Lys Ala Glu Leu Ser
1535                1540                1545

Gly Ser Asn Lys Glu Ala Gly Glu Asp Lys Ile His Ala Lys His
1550                1555                1560

Val Asn Val Glu Ala Lys Ser Ser Thr Val Val Asn Ala Ala
1565                1570                1575

Ser Gly Leu Ala Ile Ser Lys Asp Ala Phe Ser Gly Met Gly Ser
1580                1585                1590

Gly Ala Trp Gln Asp Leu Ser Asn Asp Thr Ile Ala Lys Val Asp
1595                1600                1605

Lys Gly Arg Ile Ser Ala Asp Ser Leu Asn Val Asn Ala Asn Asn
1610                1615                1620

Ser Ile Leu Gly Val Asn Val Ala Gly Thr Ile Ala Gly Ser Leu

-continued

```
            1625                1630                1635

Ser  Thr  Ala  Val  Gly  Ala  Ala  Phe  Ala  Asn  Asn  Thr  Leu  His  Asn
       1640                1645                1650

Lys  Thr  Ser  Ala  Leu  Ile  Thr  Gly  Thr  Lys  Val  Asn  Pro  Phe  Ser
       1655                1660                1665

Gly  Lys  Asn  Thr  Lys  Val  Asn  Val  Gln  Ala  Leu  Asn  Asp  Ser  His
       1670                1675                1680

Ile  Thr  Asn  Val  Ser  Ala  Gly  Ala  Ala  Ser  Ile  Lys  Gln  Ala
       1685                1690                1695

Gly  Ile  Gly  Gly  Met  Val  Ser  Val  Asn  Arg  Gly  Ser  Asp  Glu  Thr
       1700                1705                1710

Glu  Ala  Leu  Val  Ser  Asp  Ser  Glu  Phe  Glu  Gly  Val  Ser  Ser  Phe
       1715                1720                1725

Asn  Val  Asp  Ala  Lys  Asp  Gln  Lys  Thr  Ile  Asn  Thr  Ile  Ala  Gly
       1730                1735                1740

Asn  Ala  Asn  Gly  Gly  Lys  Ala  Ala  Gly  Val  Gly  Ala  Thr  Val  Ala
       1745                1750                1755

His  Thr  Asn  Ile  Gly  Lys  Gln  Ser  Val  Ile  Ala  Ile  Val  Lys  Asn
       1760                1765                1770

Ser  Lys  Ile  Thr  Thr  Ala  Asn  Asp  Gln  Asp  Arg  Lys  Asn  Ile  Asn
       1775                1780                1785

Val  Thr  Ala  Lys  Asp  Tyr  Thr  Met  Thr  Asn  Thr  Ile  Ala  Val  Gly
       1790                1795                1800

Val  Gly  Gly  Ala  Lys  Gly  Ala  Ser  Val  Gln  Gly  Ala  Ser  Ala  Ser
       1805                1810                1815

Thr  Thr  Leu  Asn  Lys  Thr  Val  Ser  Ser  His  Val  Asp  Gln  Thr  Asp
       1820                1825                1830

Ile  Asp  Lys  Asp  Leu  Glu  Glu  Glu  Asn  Asn  Gly  Asn  Lys  Glu  Lys
       1835                1840                1845

Ala  Asn  Val  Asn  Val  Leu  Ala  Glu  Asn  Thr  Ser  Gln  Val  Val  Thr
       1850                1855                1860

Asn  Ala  Thr  Val  Leu  Ser  Gly  Ala  Ser  Gly  Gln  Ala  Ala  Val  Gly
       1865                1870                1875

Ala  Gly  Val  Ala  Val  Asn  Lys  Ile  Thr  Gln  Asn  Thr  Ser  Ala  His
       1880                1885                1890

Ile  Lys  Asn  Ser  Thr  Gln  Asn  Val  Arg  Asn  Ala  Leu  Val  Lys  Ser
       1895                1900                1905

Lys  Ser  His  Ser  Ser  Ile  Lys  Thr  Ile  Gly  Ile  Gly  Ala  Gly  Val
       1910                1915                1920

Gly  Ala  Gly  Gly  Ala  Gly  Val  Thr  Gly  Ser  Val  Ala  Val  Asn  Lys
       1925                1930                1935

Ile  Val  Asn  Asn  Thr  Ile  Ala  Glu  Leu  Asn  His  Ala  Lys  Ile  Thr
       1940                1945                1950

Ala  Lys  Gly  Asn  Val  Gly  Val  Ile  Thr  Glu  Ser  Asp  Ala  Val  Ile
       1955                1960                1965

Ala  Asn  Tyr  Ala  Gly  Thr  Val  Ser  Gly  Val  Ala  Arg  Ala  Ala  Ile
       1970                1975                1980

Gly  Ala  Ser  Thr  Ser  Val  Asn  Glu  Ile  Thr  Gly  Ser  Thr  Lys  Ala
       1985                1990                1995

Tyr  Val  Lys  Asp  Ser  Thr  Val  Ile  Ala  Lys  Glu  Glu  Thr  Asp  Asp
       2000                2005                2010

Tyr  Ile  Thr  Thr  Gln  Gly  Gln  Val  Asp  Lys  Val  Val  Asp  Lys  Val
       2015                2020                2025
```

```
Phe Lys Asn Leu Asn Ile Asn Glu Asp Leu Ser Gln Lys Arg Lys
    2030            2035                2040

Ile Ser Asn Lys Lys Gly Phe Val Thr Asn Ser Ser Ala Thr His
    2045            2050                2055

Thr Leu Lys Ser Leu Leu Ala Asn Ala Ala Gly Ser Gly Gln Ala
    2060            2065                2070

Gly Val Ala Gly Thr Val Asn Ile Asn Lys Val Tyr Gly Glu Thr
    2075            2080                2085

Glu Ala Leu Val Glu Asn Ser Ile Leu Asn Ala Lys His Tyr Ser
    2090            2095                2100

Val Lys Ser Gly Asp Tyr Thr Asn Ser Ile Gly Val Val Gly Ser
    2105            2110                2115

Val Gly Val Gly Gly Asn Val Gly Val Gly Ala Ser Ser Asp Thr
    2120            2125                2130

Asn Ile Ile Lys Arg Asn Thr Lys Thr Arg Val Gly Lys Thr Thr
    2135            2140                2145

Met Ser Asp Glu Gly Phe Gly Glu Ala Glu Ile Thr Ala Asp
    2150            2155                2160

Ser Lys Gln Gly Ile Ser Ser Phe Gly Val Gly Val Ala Ala Ala
    2165            2170                2175

Gly Val Gly Ala Gly Val Ala Gly Thr Val Ser Val Asn Gln Phe
    2180            2185                2190

Ala Gly Lys Thr Glu Val Asp Val Glu Glu Ala Lys Ile Leu Val
    2195            2200                2205

Lys Lys Ala Glu Ile Thr Ala Lys Arg Tyr Ser Ser Val Ala Ile
    2210            2215                2220

Gly Asn Ala Ala Val Gly Val Ala Ala Lys Gly Ala Gly Ile Gly
    2225            2230                2235

Ala Ala Val Ala Val Thr Lys Asp Glu Ser Asn Thr Arg Ala Arg
    2240            2245                2250

Val Lys Asn Ser Lys Ile Met Thr Arg Asn Lys Leu Asp Val Ile
    2255            2260                2265

Ala Glu Asn Glu Ile Lys Ser Gly Thr Gly Ile Gly Ser Ala Gly
    2270            2275                2280

Ala Gly Ile Leu Ala Ala Gly Val Ser Gly Val Val Ser Val Asn
    2285            2290                2295

Asn Ile Ala Asn Lys Val Glu Thr Asp Ile Asp His Ser Thr Leu
    2300            2305                2310

His Ser Ser Thr Asp Val Asn Val Lys Ala Leu Asn Lys Ile Ser
    2315            2320                2325

Asn Ser Leu Thr Ala Gly Gly Gly Ala Ala Gly Leu Ala Ala Val
    2330            2335                2340

Thr Gly Val Val Ser Val Asn Thr Ile Asn Ser Ser Val Ile Ala
    2345            2350                2355

Arg Val His Asn Asn Ser Asp Leu Thr Ser Val Arg Glu Lys Val
    2360            2365                2370

Asn Val Thr Ala Lys Glu Glu Lys Asn Ile Lys Gln Thr Ala Ala
    2375            2380                2385

Asn Ala Gly Ile Gly Gly Ala Ala Ile Gly Ala Asn Val Leu Val
    2390            2395                2400

Asn Asn Phe Gly Thr Ala Val Glu Asp Arg Lys Asn Ser Glu Gly
    2405            2410                2415
```

-continued

```
Lys Gly Thr Glu Val Leu Lys Thr Leu Asp Glu Val Asn Lys Glu
2420                2425                2430

Gln Asp Lys Lys Val Asn Asp Ala Thr Lys Lys Ile Leu Gln Ser
2435                2440                2445

Ala Gly Ile Ser Thr Glu Asp Thr Ser Val Lys Ala Asp Arg Gly
2450                2455                2460

Asp Thr Gln Gly Glu Gly Ile Lys Ala Ile Val Lys Thr Ser Asp
2465                2470                2475

Ile Ile Gly Lys Asn Val Asp Ile Thr Thr Glu Asp Lys Asn Asn
2480                2485                2490

Ile Thr Ser Thr Gly Gly Leu Gly Thr Ala Gly Leu Ala Ser Ala
2495                2500                2505

Ser Gly Thr Val Ala Val Thr Asn Ile Lys Arg Asn Ser Gly Val
2510                2515                2520

Thr Val Glu Asn Ser Phe Val Lys Ala Ala Glu Lys Val Asn Val
2525                2530                2535

Arg Ser Asp Ile Thr Gly Asn Val Ala Leu Thr Ala Tyr Gln Gly
2540                2545                2550

Pro Val Gly Ala Leu Gly Ile Gly Ala Ala Tyr Ala Glu Leu Asn
2555                2560                2565

Ser Asn Gly Arg Ser Asn Ile Ser Ile Lys Asn Ser Lys Leu Leu
2570                2575                2580

Gly Lys Asn Ile Asp Val Ile Val Lys Asp Lys Ser Glu Leu Arg
2585                2590                2595

Ala Glu Ala Lys Gly Leu Thr Val Gly Ala Val Ala Ala Gly Ala
2600                2605                2610

Ile Ile Ser Lys Ala Lys Asn Glu Met Asn Ser Glu Val Glu Ile
2615                2620                2625

Glu Lys Ser Ile Phe Asn Glu Glu Asn Arg Val Thr Ser Pro Ser
2630                2635                2640

Lys Gly Ile Gly Arg Glu Ile Asn Val Lys Val Glu Lys Glu Asn
2645                2650                2655

Arg Val Thr Ala Glu Ser Gln Gly Ala Ser Val Gly Ala Val Ala
2660                2665                2670

Gly Ala Gly Ile Ile Ser Glu Ala Lys Asp Ala Gly Ser Ser Tyr
2675                2680                2685

Leu Lys Val Ser Thr Lys Ser Gly Arg Ser Ile Phe His Ala Asp
2690                2695                2700

Asn Val Asn Met Glu Ala Thr His Lys Met Lys Val Thr Ala Val
2705                2710                2715

Ser Lys Ala Val Thr Gly Ser Val Leu Gly Gly Val Gly Val Thr
2720                2725                2730

Lys Ala Glu Ala Thr Ala Ala Gly Lys Thr Met Val Glu Val Glu
2735                2740                2745

Glu Gly Asn Leu Phe Arg Thr Asn Arg Leu Asn Ala Ile Ser Lys
2750                2755                2760

Val Glu Gly Leu Asp Glu Asp Lys Val Thr Ala Lys Ser Ser Val
2765                2770                2775

Val Ser Gly Asn Gly Gly Ile Ala Gly Ala Gly Val Asn Thr
2780                2785                2790

Ser Thr Ala Gln Ser Asn Thr Glu Ser Val Val Arg Leu Arg Lys
2795                2800                2805

Gln Asp Tyr Glu Asn Asn Asp Tyr Thr Lys Lys Tyr Ile Ser Glu
```

-continued

```
              2810                2815                2820
Val Asn Ala Leu Ala Leu Asn Asp Thr Lys Asn Glu Ala Asn Ile
        2825                2830                2835
Glu Ser Leu Ala Val Ala Gly Val His Ala Gln Gly Thr Asn Lys
        2840                2845                2850
Ala Phe Thr Arg Ser Asn Lys Leu Thr Ser Thr Thr Val Asn Gly
        2855                2860                2865
Gly Asn Val Ser Gln Leu Arg Ala Lys Ala Leu Ala Lys Asn Glu
        2870                2875                2880
Asn Tyr Gly Asn Val Lys Gly Thr Gly Gly Ala Leu Val Gly Ala
        2885                2890                2895
Glu Thr Ala Ala Val Glu Asn Tyr Thr Lys Ser Thr Thr Gly Ala
        2900                2905                2910
Leu Val Ala Gly Asn Trp Glu Ile Gly Asp Lys Leu Glu Thr Ile
        2915                2920                2925
Ala Arg Asp Asn Thr Ile Val Arg Val Asn Gly Asp Gly Thr Lys
        2930                2935                2940
Gly Gly Leu Val Gly Lys Asn Gly Ile Ser Val Lys Asn Thr Ile
        2945                2950                2955
Ser Gly Glu Thr Lys Ser Ser Ile Glu Asp Lys Ala Arg Ile Val
        2960                2965                2970
Gly Thr Gly Ser Val Asn Val Asp Ala Leu Asn Glu Leu Asp Val
        2975                2980                2985
Asp Leu Gln Gly Lys Ser Gly Gly Tyr Gly Gly Ile Gly Ile Gly
        2990                2995                3000
Asn Val Asp Val Asn Asn Val Ile Lys Lys Asn Val Glu Ala Lys
        3005                3010                3015
Ile Gly Arg His Ala Ile Val Glu Thr Thr Gly Lys Gln Glu Tyr
        3020                3025                3030
Gln Ala Phe Thr Arg Ala Lys Val Asn Ile Leu Gly Lys Gly Asp
        3035                3040                3045
Ala Ala Ala Ala Ala Ala Ile Ser Asn Val His Ile Ser Asn Glu
        3050                3055                3060
Met Asp Ile Lys Asn Leu Ala Lys Gln Tyr Ala Ser Ser Gln Leu
        3065                3070                3075
Ile Thr Lys Asn Ser Lys Asn Asn Ile Thr Leu Ala Ser Ser Ser
        3080                3085                3090
Glu Ser Asn Val Asn Val His Gly Val Ala Glu Ala Arg Gly Ala
        3095                3100                3105
Gly Ala Lys Ala Thr Val Ser Val Lys Asn Gln Ile Asn Arg Thr
        3110                3115                3120
Asn Asn Val Asp Leu Ala Gly Lys Ile Lys Thr Glu Gly Asn Ile
        3125                3130                3135
Asn Val Tyr Ala Gly Tyr Asp Lys Asn Tyr Asn Ile Ser Lys Thr
        3140                3145                3150
Asn Ser Lys Ala Ile Ala Asp Ala Lys Ser His Ala Ala Ala Ala
        3155                3160                3165
Ser Ala Thr Ala Thr Ile Glu Lys Asn Glu Val Lys Phe Asn Asn
        3170                3175                3180
Ala Ile Arg Glu Phe Lys Asn Asn Leu Ala Arg Leu Glu Gly Lys
        3185                3190                3195
Ala Asn Lys Lys Thr Ser Val Gly Ser Asn Gln Val Asp Trp Tyr
        3200                3205                3210
```

```
Thr Asp Lys Tyr Thr Trp His Ser Ser Glu Lys Ala Tyr Lys Lys
    3215                3220                3225

Leu Thr Tyr Gln Ser Lys Arg Gly Glu Lys Gly Lys Lys
    3230                3235            3240

<210> SEQ ID NO 2
<211> LENGTH: 369
<212> TYPE: PRT
<213> ORGANISM: Fusobacterium necrophorum

<400> SEQUENCE: 2

Met Ser Gly Ile Lys Asn Asn Val Gln Arg Thr Arg Lys Arg Ile Ser
1               5                   10                  15

Asp Ser Lys Lys Val Leu Met Ile Leu Gly Leu Leu Ile Asn Thr Met
            20                  25                  30

Thr Val Arg Ala Asn Asp Thr Ile Thr Ala Thr Glu Asn Phe Gly Thr
        35                  40                  45

Lys Ile Glu Lys Lys Asp Asn Val Tyr Asp Ile Thr Thr Asn Lys Ile
    50                  55                  60

Gln Gly Glu Asn Ala Phe Asn Ser Phe Asn Arg Phe Ala Leu Thr Glu
65                  70                  75                  80

Asn Asn Ile Ala Asn Leu Tyr Phe Gly Glu Lys Asn Ser Thr Gly Val
                85                  90                  95

Asn Asn Leu Phe Asn Phe Val Asn Gly Lys Ile Glu Val Asp Gly Ile
            100                 105                 110

Ile Asn Gly Ile Arg Glu Asn Lys Ile Gly Gly Asn Leu Tyr Phe Leu
        115                 120                 125

Ser Ser Glu Gly Met Ala Val Gly Lys Asn Gly Val Ile Asn Ala Gly
    130                 135                 140

Ser Phe His Ser Ile Ile Pro Lys Gln Asp Asp Phe Lys Lys Ala Leu
145                 150                 155                 160

Glu Glu Ala Lys His Gly Lys Val Phe Asn Gly Ile Ile Pro Val Asp
                165                 170                 175

Gly Lys Val Lys Ile Pro Leu Asn Pro Asn Gly Ser Ile Thr Val Glu
            180                 185                 190

Gly Lys Ile Asn Ala Val Glu Gly Ile Gly Leu Tyr Ala Ala Asp Ile
        195                 200                 205

Arg Leu Lys Asp Thr Ala Ile Leu Lys Thr Gly Ile Thr Asp Phe Lys
    210                 215                 220

Asn Leu Val Asn Ile Ser Asp Arg Ile Asn Ser Gly Leu Thr Gly Asp
225                 230                 235                 240

Leu Lys Ala Thr Lys Thr Lys Ser Gly Asp Ile Ile Leu Ser Ala His
                245                 250                 255

Ile Asp Ser Pro Gln Lys Ala Met Gly Lys Asn Ser Thr Val Gly Lys
            260                 265                 270

Arg Ile Glu Glu Tyr Val Lys Gly Asn Thr Lys Ala Asn Ile Glu Ser
        275                 280                 285

Asp Ala Val Leu Glu Ala Asp Gly Asn Ile Lys Ile Ser Ala Lys Ala
    290                 295                 300

Thr Asn Gly Arg Phe Ile Lys Lys Glu Gly Glu Lys Glu Thr Tyr Asn
305                 310                 315                 320

Thr Pro Leu Ser Leu Ser Asp Val Glu Ala Ser Val Arg Val Asn Lys
                325                 330                 335

Gly Lys Val Ile Gly Lys Asn Val Asp Ile Thr Ala Glu Ala Lys Asn
```

```
                   340                 345                 350
Phe Tyr Asp Ala Thr Leu Val Thr Lys Leu Ala Lys His Ser Phe Ser
            355                 360                 365

Phe

<210> SEQ ID NO 3
<211> LENGTH: 927
<212> TYPE: PRT
<213> ORGANISM: Fusobacterium necrophorum

<400> SEQUENCE: 3

Gly Arg Phe Ile Lys Lys Glu Gly Glu Lys Glu Thr Tyr Asn Thr Pro
1               5                   10                  15

Leu Ser Leu Ser Asp Val Glu Ala Ser Val Arg Val Asn Lys Gly Lys
            20                  25                  30

Val Ile Gly Lys Asn Val Asp Ile Thr Ala Glu Ala Lys Asn Phe Tyr
        35                  40                  45

Asp Ala Thr Leu Val Thr Lys Leu Ala Lys His Ser Phe Ser Phe Val
    50                  55                  60

Thr Gly Ser Ile Ser Pro Ile Asn Leu Asn Gly Phe Leu Gly Leu Leu
65                  70                  75                  80

Thr Ser Lys Ser Ser Val Val Ile Gly Lys Asp Ala Lys Val Glu Ala
            85                  90                  95

Thr Glu Gly Lys Ala Asn Ile His Ser Tyr Ser Gly Val Arg Ala Thr
            100                 105                 110

Met Gly Ala Ala Thr Ser Pro Leu Lys Ile Thr Asn Leu Tyr Leu Glu
        115                 120                 125

Lys Ala Asn Gly Lys Leu Leu Ser Ile Gly Ala Gly Tyr Ile Ser Ala
    130                 135                 140

Lys Ser Asn Ser Asn Val Thr Ile Glu Gly Glu Val Lys Ser Lys Gly
145                 150                 155                 160

Arg Ala Asp Ile Thr Ser Lys Ser Glu Asn Thr Ile Asp Ala Ser Val
            165                 170                 175

Ser Val Gly Thr Met Arg Asp Ser Asn Lys Val Ala Leu Ser Val Leu
            180                 185                 190

Val Thr Glu Gly Glu Asn Lys Ser Ser Val Lys Ile Ala Lys Gly Ala
        195                 200                 205

Lys Val Glu Ser Glu Thr Asp Asp Val Asn Val Arg Ser Glu Ala Ile
    210                 215                 220

Asn Ser Ile Arg Ala Ala Val Lys Gly Gly Leu Gly Asp Ser Gly Asn
225                 230                 235                 240

Gly Val Val Ala Ala Asn Ile Ser Asn Tyr Asn Ala Ser Ser Arg Ile
            245                 250                 255

Asp Val Asp Gly Tyr Leu His Ala Lys Lys Arg Leu Asn Val Glu Ala
            260                 265                 270

His Asn Ile Thr Lys Asn Ser Val Leu Gln Thr Gly Ser Asp Leu Gly
        275                 280                 285

Thr Ser Lys Phe Met Asn Asp His Val Tyr Glu Ser Gly His Leu Lys
    290                 295                 300

Ser Ile Leu Asp Ala Ile Lys Gln Arg Phe Gly Gly Asp Ser Val Asn
305                 310                 315                 320

Glu Glu Ile Lys Asn Lys Leu Thr Asn Leu Phe Ser Val Gly Val Ser
            325                 330                 335

Ala Thr Ile Ala Asn His Asn Asn Ser Ala Ser Val Ala Ile Gly Glu
```

-continued

```
                340                 345                 350
Ser Gly Arg Leu Ser Ser Val Glu Gly Ser Asn Val Arg Ala Leu
            355                 360                 365
Asn Glu Ala Gln Asn Leu Arg Ala Thr Thr Ser Ser Gly Ser Val Ala
        370                 375                 380
Val Arg Lys Glu Glu Lys Lys Leu Ile Gly Asn Ala Ala Val Phe
385                 390                 395                 400
Tyr Gly Asn Tyr Lys Asn Ala Ser Val Thr Ile Ala Asp His Ala
                405                 410                 415
Glu Leu Val Ser Glu Gly Lys Ile Asp Ile Asn Ser Glu Asn Lys Ile
            420                 425                 430
Glu Tyr Lys Asn Pro Ser Lys Met Ala Lys Ser Val Ile Asp Lys Leu
        435                 440                 445
Glu Leu Leu Lys Arg Ala Phe Gly Lys Glu Thr Lys Thr Pro Glu Tyr
450                 455                 460
Asp Pro Lys Asp Ile Glu Ser Ile Glu Lys Leu Leu Asn Ala Phe Ser
465                 470                 475                 480
Glu Lys Leu Asp Gly Lys Pro Glu Leu Leu Leu Asn Gly Glu Arg Met
            485                 490                 495
Thr Ile Ile Leu Pro Asp Gly Thr Ser Lys Thr Gly Thr Ala Ile Glu
            500                 505                 510
Ile Ala Asn Tyr Val Gln Gly Glu Met Lys Lys Leu Glu Glu Lys Leu
        515                 520                 525
Pro Lys Gly Phe Lys Ala Phe Ser Glu Gly Leu Ser Gly Leu Ile Lys
        530                 535                 540
Glu Thr Leu Asn Phe Thr Gly Val Gly Asn Tyr Ala Asn Phe His Thr
545                 550                 555                 560
Phe Thr Ser Ser Gly Ala Asn Gly Glu Arg Asp Val Ser Ser Val Gly
            565                 570                 575
Gly Ala Val Ser Trp Val Glu Gln Asn Tyr Ser Lys Val Ser Val
            580                 585                 590
Gly Lys Gly Ala Lys Leu Ala Ala Lys Lys Asp Leu Asn Ile Lys Ala
        595                 600                 605
Ile Asn Lys Ala Glu Thr Val Asn Leu Val Gly Asn Ile Gly Leu Ala
        610                 615                 620
Arg Ser Ser Thr Ser Gly Ser Ala Val Gly Gly Arg Leu Asn Val Gln
625                 630                 635                 640
Arg Ser Lys Asn Ser Ala Ile Val Glu Ala Lys Glu Lys Ala Glu Leu
                645                 650                 655
Ser Gly Glu Asn Ile Asn Ala Asp Ala Leu Asn Arg Leu Phe His Val
            660                 665                 670
Ala Gly Ser Phe Asn Gly Gly Ser Gly Gly Asn Ala Ile Asn Gly Met
        675                 680                 685
Gly Ser Tyr Ser Gly Gly Ile Ser Lys Ala Arg Val Ser Ile Asp Asp
        690                 695                 700
Glu Ala Tyr Leu Lys Ala Asn Lys Lys Ile Ala Leu Asn Ser Lys Asn
705                 710                 715                 720
Asp Thr Ser Val Trp Asn Ala Ala Gly Ser Ala Gly Ile Gly Thr Lys
                725                 730                 735
Asn Ala Ala Val Gly Val Ala Val Ala Val Asn Asp Tyr Asp Ile Ser
            740                 745                 750
Asn Lys Ala Ser Ile Glu Asp Asn Asp Glu Gly Gln Ser Lys Tyr Asp
        755                 760                 765
```

```
Lys Asn Lys Asp Asp Glu Val Thr Val Thr Ala Glu Ser Leu Glu Val
        770                 775                 780

Asp Ala Lys Thr Thr Gly Thr Ile Asn Ser Ile Ser Val Ala Gly Gly
785                 790                 795                 800

Ile Asn Lys Val Gly Ser Lys Pro Ser Glu Lys Pro Lys Ser Glu
            805                 810                 815

Glu Arg Pro Glu Gly Phe Phe Gly Lys Ile Gly Asn Lys Val Asp Ser
            820                 825                 830

Val Lys Asn Lys Ile Thr Asp Ser Met Asp Ser Leu Thr Glu Lys Ile
        835                 840                 845

Thr Asn Tyr Ile Ser Glu Gly Val Lys Lys Ala Gly Asn Leu Pro Ser
        850                 855                 860

Asn Val Ser His Thr Pro Asp Lys Gly Pro Ser Phe Ser Leu Gly Ala
865                 870                 875                 880

Ser Gly Ser Val Ser Phe Asn Asn Ile Lys Lys Glu Thr Ser Ala Val
            885                 890                 895

Val Asp Gly Val Lys Ile Asn Leu Lys Gly Ala Asn Lys Lys Val Glu
            900                 905                 910

Val Thr Ser Ser Asp Ser Thr Phe Val Gly Ala Trp Gly Gly Ser
        915                 920                 925

<210> SEQ ID NO 4
<211> LENGTH: 580
<212> TYPE: PRT
<213> ORGANISM: Fusobacterium necrophorum

<400> SEQUENCE: 4

Gly Ala Ser Gly Ser Val Ser Asn Asn Lys Lys Thr Ser Ala Val Val
1               5                   10                  15

Asp Gly Val Lys Asn Lys Gly Ala Asn Lys Lys Val Val Thr Ser Ser
            20                  25                  30

Asp Ser Thr Val Gly Ala Trp Gly Gly Ser Ala Ala Trp Asn His Gly
        35                  40                  45

Ser Gly Asn Ser Asn Ser Ala Gly Ala Gly Ala Ala Val Asn Asn
    50                  55                  60

Ser Lys Thr Ser Ala Val Lys Asn Ser Asp Arg Asn Ala Asn Lys Lys
65                  70                  75                  80

Val Asn Ala Ser Gly Gly Thr Val Ala Ala Gly Ala Gly Ala Val Lys
            85                  90                  95

Ser Gly Gly Gly Lys Ser Tyr Gly Thr Ser Ala Ser Asn Val Asn Asn
            100                 105                 110

Val Ser Ala Lys Ser Asn Asn Thr Val Ala Gly Ser Ser Lys Met Asp
        115                 120                 125

Val Asp Val Thr Ala Tyr Ala Asp Thr Val Thr Gly Ala Asn Ala Gly
        130                 135                 140

Lys Ser Asn Gly Thr Val Gly Ala Thr Val Thr Val Ala Lys Asn Asn
145                 150                 155                 160

Lys Val Asn Ala Ser Gly Gly Arg Tyr Thr Asn Val Asn Arg Ala
            165                 170                 175

Asp Ala Lys Ala Ala Thr Thr Val Thr Ala Val Thr Thr Gly Gly
        180                 185                 190

Thr Ser Ser Gly Ala Gly Gly Asn Tyr Gly Ala Val Ser Val Asn Lys
        195                 200                 205

Asp Asn Asp Val Ala Ser Val Asp Lys Ser Ser Gly Ala Asn Asn Val
```

```
            210                 215                 220
Ala Lys Asp Val Lys Gly Ser Ser Asp Ala Lys Tyr Ala Asn Gly Lys
225                 230                 235                 240

Asp Lys Lys Tyr Asp Arg Gly Asn Thr Thr Gly Asn Gly Tyr Tyr Thr
                245                 250                 255

Lys Lys Ala Lys Lys Gly Ala Val Val Asn Ala Ala Ser Val Ala
            260                 265                 270

Gly Thr Asp Lys Ser Ala Gly Val Ala Ala Val Asn Thr Val Lys
                275                 280                 285

Asn Lys Lys Ala Ser Gly Ser Asn Lys Ala Gly Asp Lys His Ala Lys
290                 295                 300

His Val Asn Val Ala Lys Ser Ser Thr Val Val Asn Ala Ala Ser
305                 310                 315                 320

Gly Ala Ser Lys Asp Ala Ser Gly Met Gly Ser Gly Ala Trp Asp Ser
                325                 330                 335

Asn Asp Thr Ala Lys Val Asp Lys Gly Arg Ser Ala Asp Ser Asn Val
            340                 345                 350

Asn Ala Asn Asn Ser Gly Val Asn Val Ala Gly Thr Ala Gly Ser Ser
            355                 360                 365

Thr Ala Val Gly Ala Ala Ala Asn Asn Thr His Asn Lys Thr Ser Ala
370                 375                 380

Thr Gly Thr Lys Val Asn Ser Gly Lys Asn Thr Lys Val Asn Val Ala
385                 390                 395                 400

Asn Asp Ser His Thr Asn Val Ser Ala Gly Gly Ala Ala Ser Lys Ala
            405                 410                 415

Gly Gly Gly Met Val Ser Val Asn Arg Gly Ser Asp Thr Ala Val Ser
                420                 425                 430

Asp Ser Gly Val Ser Ser Asn Val Asp Ala Lys Asp Lys Thr Asn Thr
            435                 440                 445

Ala Gly Asn Ala Asn Gly Gly Lys Ala Ala Gly Gly Val Gly Ala Thr Val
            450                 455                 460

Ala His Thr Asn Gly Lys Ser Val Ala Val Lys Asn Ser Lys Thr Thr
465                 470                 475                 480

Ala Asn Asp Asp Arg Lys Asn Asn Val Thr Ala Lys Asp Tyr Thr Met
                485                 490                 495

Thr Asn Thr Ala Val Gly Val Gly Gly Ala Lys Gly Ala Ser Val Gly
            500                 505                 510

Ala Ser Ala Ser Thr Thr Asn Lys Thr Val Ser Ser His Val Asp Thr
            515                 520                 525

Asp Asp Lys Asp Asn Asn Gly Asn Lys Lys Ala Asn Val Asn Val Ala
530                 535                 540

Asn Thr Ser Val Val Thr Asn Ala Thr Val Ser Gly Ala Ser Gly Ala
545                 550                 555                 560

Ala Val Gly Ala Gly Val Ala Val Asn Lys Thr Asn Thr Ser Ala His
                565                 570                 575

Lys Asn Ser Thr
            580

<210> SEQ ID NO 5
<211> LENGTH: 628
<212> TYPE: PRT
<213> ORGANISM: Fusobacterium necrophorum

<400> SEQUENCE: 5
```

-continued

```
Ala Val Gly Ala Gly Val Ala Val Asn Lys Ile Thr Gln Asn Thr Ser
1               5                   10                  15

Ala His Ile Lys Asn Ser Thr Gln Asn Val Arg Asn Ala Leu Val Lys
            20                  25                  30

Ser Lys Ser His Ser Ser Ile Lys Thr Ile Gly Ile Gly Ala Gly Val
        35                  40                  45

Gly Ala Gly Gly Ala Gly Val Thr Gly Ser Val Ala Val Asn Lys Ile
    50                  55                  60

Val Asn Asn Thr Ile Ala Glu Leu Asn His Ala Lys Ile Thr Ala Lys
65                  70                  75                  80

Gly Asn Val Gly Val Ile Thr Glu Ser Asp Ala Val Ile Ala Asn Tyr
                85                  90                  95

Ala Gly Thr Val Ser Gly Val Ala Arg Ala Ala Ile Gly Ala Ser Thr
                100                 105                 110

Ser Val Asn Glu Ile Thr Gly Ser Thr Lys Ala Tyr Val Lys Asp Ser
            115                 120                 125

Thr Val Ile Ala Lys Glu Glu Thr Asp Asp Tyr Ile Thr Thr Gln Gly
        130                 135                 140

Gln Val Asp Lys Val Asp Lys Val Phe Lys Asn Leu Asn Ile Asn
145                 150                 155                 160

Glu Asp Leu Ser Gln Lys Arg Lys Ile Ser Asn Lys Lys Gly Phe Val
                165                 170                 175

Thr Asn Ser Ser Ala Thr His Thr Leu Lys Ser Leu Leu Ala Asn Ala
            180                 185                 190

Ala Gly Ser Gly Gln Ala Gly Val Ala Gly Thr Val Asn Ile Asn Lys
        195                 200                 205

Val Tyr Gly Glu Thr Glu Ala Leu Val Glu Asn Ser Ile Leu Asn Ala
    210                 215                 220

Lys His Tyr Ser Val Lys Ser Gly Asp Tyr Thr Asn Ser Ile Gly Val
225                 230                 235                 240

Val Gly Ser Val Gly Val Gly Asn Val Gly Val Gly Ala Ser Ser
                245                 250                 255

Asp Thr Asn Ile Ile Lys Arg Asn Thr Lys Thr Arg Val Gly Lys Thr
                260                 265                 270

Thr Met Ser Asp Glu Gly Phe Gly Glu Glu Ala Glu Ile Thr Ala Asp
            275                 280                 285

Ser Lys Gln Gly Ile Ser Ser Phe Gly Val Gly Val Ala Ala Ala Gly
        290                 295                 300

Val Gly Ala Gly Val Ala Gly Thr Val Ser Val Asn Gln Phe Ala Gly
305                 310                 315                 320

Lys Thr Glu Val Asp Val Glu Glu Ala Lys Ile Leu Val Lys Lys Ala
                325                 330                 335

Glu Ile Thr Ala Lys Arg Tyr Ser Ser Val Ala Ile Gly Asn Ala Ala
            340                 345                 350

Val Gly Val Ala Ala Lys Gly Ala Gly Ile Gly Ala Ala Val Ala Val
        355                 360                 365

Thr Lys Asp Glu Ser Asn Thr Arg Ala Arg Val Lys Asn Ser Lys Ile
    370                 375                 380

Met Thr Arg Asn Lys Leu Asp Val Ile Ala Glu Asn Glu Ile Lys Ser
385                 390                 395                 400

Gly Thr Gly Ile Gly Ser Ala Gly Ala Gly Ile Leu Ala Ala Gly Val
                405                 410                 415

Ser Gly Val Val Ser Val Asn Asn Ile Ala Asn Lys Val Glu Thr Asp
```

-continued

```
                420             425             430
Ile Asp His Ser Thr Leu His Ser Thr Asp Val Asn Val Lys Ala
        435             440             445

Leu Asn Lys Ile Ser Asn Ser Leu Thr Ala Gly Gly Ala Ala Gly
    450             455             460

Leu Ala Ala Val Thr Gly Val Ser Val Asn Thr Ile Asn Ser Ser
465             470             475             480

Val Ile Ala Arg Val His Asn Asn Ser Asp Leu Thr Ser Val Arg Glu
            485             490             495

Lys Val Asn Val Thr Ala Lys Glu Glu Lys Asn Ile Lys Gln Thr Ala
        500             505             510

Ala Asn Ala Gly Ile Gly Gly Ala Ala Ile Gly Ala Asn Val Leu Val
        515             520             525

Asn Asn Phe Gly Thr Ala Val Glu Asp Arg Lys Asn Ser Glu Gly Lys
    530             535             540

Gly Thr Glu Val Leu Lys Thr Leu Asp Glu Val Asn Lys Glu Gln Asp
545             550             555             560

Lys Lys Val Asn Asp Ala Thr Lys Lys Ile Leu Gln Ser Ala Gly Ile
            565             570             575

Ser Thr Glu Asp Thr Ser Val Lys Ala Asp Arg Gly Asp Thr Gln Gly
            580             585             590

Glu Gly Ile Lys Ala Ile Val Lys Thr Ser Asp Ile Ile Gly Lys Asn
        595             600             605

Val Asp Ile Thr Thr Glu Asp Lys Asn Asn Ile Thr Ser Thr Gly Gly
        610             615             620

Leu Gly Thr Ala
625

<210> SEQ ID NO 6
<211> LENGTH: 773
<212> TYPE: PRT
<213> ORGANISM: Fusobacterium necrophorum

<400> SEQUENCE: 6

Gly Ile Lys Ala Ile Val Lys Thr Ser Asp Ile Ile Gly Lys Asn Val
1               5                   10                  15

Asp Ile Thr Thr Glu Asp Lys Asn Asn Ile Thr Ser Thr Gly Gly Leu
            20                  25                  30

Gly Thr Ala Gly Leu Ala Ser Ala Ser Gly Thr Val Ala Val Thr Asn
        35                  40                  45

Ile Lys Arg Asn Ser Gly Val Thr Val Glu Asn Ser Phe Val Lys Ala
    50                  55                  60

Ala Glu Lys Val Asn Val Arg Ser Asp Ile Thr Gly Asn Val Ala Leu
65              70                  75                  80

Thr Ala Tyr Gln Gly Pro Val Gly Ala Leu Gly Ile Gly Ala Ala Tyr
            85                  90                  95

Ala Glu Leu Asn Ser Asn Gly Arg Ser Asn Ile Ser Ile Lys Asn Ser
            100                 105                 110

Lys Leu Leu Gly Lys Asn Ile Asp Val Ile Lys Asp Lys Ser Glu
        115                 120                 125

Leu Arg Ala Glu Ala Lys Gly Leu Thr Val Gly Ala Val Ala Ala Gly
    130                 135                 140

Ala Ile Ile Ser Lys Ala Lys Asn Glu Met Asn Ser Glu Val Glu Ile
145                 150                 155                 160
```

-continued

```
Glu Lys Ser Ile Phe Asn Glu Glu Asn Arg Val Thr Ser Pro Ser Lys
                165                 170                 175
Gly Ile Gly Arg Glu Ile Asn Val Lys Val Glu Lys Glu Asn Arg Val
            180                 185                 190
Thr Ala Glu Ser Gln Gly Ala Ser Val Gly Ala Val Ala Gly Ala Gly
        195                 200                 205
Ile Ile Ser Glu Ala Lys Asp Ala Gly Ser Ser Tyr Leu Lys Val Ser
210                 215                 220
Thr Lys Ser Gly Arg Ser Ile Phe His Ala Asp Asn Val Asn Met Glu
225                 230                 235                 240
Ala Thr His Lys Met Lys Val Thr Ala Val Ser Lys Ala Val Thr Gly
                245                 250                 255
Ser Val Leu Gly Val Gly Val Thr Lys Ala Glu Ala Thr Ala Ala
            260                 265                 270
Gly Lys Thr Met Val Glu Val Glu Glu Gly Asn Leu Phe Arg Thr Asn
        275                 280                 285
Arg Leu Asn Ala Ile Ser Lys Val Glu Gly Leu Asp Glu Asp Lys Val
290                 295                 300
Thr Ala Lys Ser Ser Val Val Ser Gly Asn Gly Gly Ile Ala Gly
305                 310                 315                 320
Ala Gly Val Asn Thr Ser Thr Ala Gln Ser Asn Thr Glu Ser Val Val
                325                 330                 335
Arg Leu Arg Lys Gln Asp Tyr Glu Asn Asn Asp Tyr Thr Lys Lys Tyr
            340                 345                 350
Ile Ser Glu Val Asn Ala Leu Ala Leu Asn Asp Thr Lys Asn Glu Ala
        355                 360                 365
Asn Ile Glu Ser Leu Ala Val Ala Gly Val His Ala Gln Gly Thr Asn
370                 375                 380
Lys Ala Phe Thr Arg Ser Asn Lys Leu Thr Ser Thr Val Asn Gly
385                 390                 395                 400
Gly Asn Val Ser Gln Leu Arg Ala Lys Ala Leu Ala Lys Asn Glu Asn
                405                 410                 415
Tyr Gly Asn Val Lys Gly Thr Gly Gly Ala Leu Val Gly Ala Glu Thr
            420                 425                 430
Ala Ala Val Glu Asn Tyr Thr Lys Ser Thr Thr Gly Ala Leu Val Ala
        435                 440                 445
Gly Asn Trp Glu Ile Gly Asp Lys Leu Glu Thr Ile Ala Arg Asp Asn
450                 455                 460
Thr Ile Val Arg Val Asn Gly Asp Gly Thr Lys Gly Gly Leu Val Gly
465                 470                 475                 480
Lys Asn Gly Ile Ser Val Lys Asn Thr Ile Ser Gly Thr Lys Ser
                485                 490                 495
Ser Ile Glu Asp Lys Ala Arg Ile Val Gly Thr Gly Ser Val Asn Val
            500                 505                 510
Asp Ala Leu Asn Glu Leu Asp Val Asp Leu Gln Gly Lys Ser Gly Gly
        515                 520                 525
Tyr Gly Gly Ile Gly Ile Gly Asn Val Asp Val Asn Val Ile Lys
530                 535                 540
Lys Asn Val Glu Ala Lys Ile Gly Arg His Ala Ile Val Glu Thr Thr
545                 550                 555                 560
Gly Lys Gln Glu Tyr Gln Ala Phe Thr Arg Ala Lys Val Asn Ile Leu
                565                 570                 575
Gly Lys Gly Asp Ala Ala Ala Ala Ala Ala Ile Ser Asn Val His Ile
```

```
                580             585             590
Ser Asn Glu Met Asp Ile Lys Asn Leu Ala Lys Gln Tyr Ala Ser Ser
                595                 600                 605

Gln Leu Ile Thr Lys Asn Ser Lys Asn Ile Thr Leu Ala Ser Ser
            610                 615                 620

Ser Glu Ser Asn Val Asn Val His Gly Val Ala Glu Ala Arg Gly Ala
625                 630                 635                 640

Gly Ala Lys Ala Thr Val Ser Val Lys Asn Gln Ile Asn Arg Thr Asn
                645                 650                 655

Asn Val Asp Leu Ala Gly Lys Ile Lys Thr Glu Gly Asn Ile Asn Val
            660                 665                 670

Tyr Ala Gly Tyr Asp Lys Asn Tyr Asn Ile Ser Lys Thr Asn Ser Lys
        675                 680                 685

Ala Ile Ala Asp Ala Lys Ser His Ala Ala Ala Ser Ala Thr Ala
    690                 695                 700

Thr Ile Glu Lys Asn Glu Val Lys Phe Asn Asn Ala Ile Arg Glu Phe
705                 710                 715                 720

Lys Asn Asn Leu Ala Arg Leu Glu Gly Lys Ala Asn Lys Lys Thr Ser
                725                 730                 735

Val Gly Ser Asn Gln Val Asp Trp Tyr Thr Asp Lys Tyr Thr Trp His
            740                 745                 750

Ser Ser Glu Lys Ala Tyr Lys Lys Leu Thr Tyr Gln Ser Lys Arg Gly
        755                 760                 765

Glu Lys Gly Lys Lys
    770

<210> SEQ ID NO 7
<211> LENGTH: 338
<212> TYPE: PRT
<213> ORGANISM: Fusobacterium necrophorum

<400> SEQUENCE: 7

Ile Asn Met Ala Ser Gly Lys Val Pro Gly Thr Thr Asp Tyr Phe Val
1               5                   10                  15

Gln Ile Tyr Glu Pro Lys Arg Gln Gln Phe Val Phe Ala Asp Asn
            20                  25                  30

Leu Gly Gln Lys Asn Thr Gly Glu Leu Arg Trp Gly Leu Asn Tyr Ile
        35                  40                  45

Asn Asn Ser Val Thr Gly Asn Arg Asp Gln Leu Ser Leu Thr Ser Leu
    50                  55                  60

Val Thr Glu Gly Thr Ala Ser Leu Ser Ser Phe Tyr Thr Phe Pro Val
65              70                  75                  80

Ser Lys Lys Gly Thr Lys Ile Ser Leu Gln His Ser Val Gly Lys Leu
                85                  90                  95

Lys His Ile Gln Gly Ala Leu His Lys Ile Thr Gly Asn Ser Tyr
            100                 105                 110

Ser Tyr Gly Val Gly Ile Val His Pro Ile Leu Val His Glu Lys Asn
        115                 120                 125

Lys Val Glu Leu Ser Leu Asp Trp Val Lys Gln Arg Thr Val Thr Asp
    130                 135                 140

Leu Leu Lys Leu Lys Trp Val Asn Asn Arg Leu Ser Lys Tyr Thr Ala
145                 150                 155                 160

Gly Ile Gly Ile Ser His Tyr Glu Glu Asp Ser Val Phe Tyr Thr Lys
                165                 170                 175
```

-continued

```
Gln Asn Ile Thr Lys Gly Lys Phe Ile Pro Ile Ser Gly Asp Ala Arg
            180                 185                 190

Asn Tyr Thr Lys Tyr Asp Met Phe Leu Ile Tyr Gln Lys Asn Leu Lys
        195                 200                 205

Tyr Asn Thr Leu Val Thr Leu Lys Met Ala Gly Gln Tyr Ser Leu Ser
    210                 215                 220

Lys Lys Leu Pro Ser Val Glu Gln Ile Tyr Ala Gly Ala Tyr Asn
225                 230                 235                 240

Val Arg Gly Tyr Pro Glu Asn Phe Met Gly Ala Glu His Gly Val Phe
                245                 250                 255

Phe Asn Ala Glu Leu Ser Lys Leu Val Glu Asn Lys Gly Glu Phe Phe
            260                 265                 270

Val Phe Leu Asp Gly Ala Ser Leu His Gly Glu Ser Ala Trp Gln Glu
        275                 280                 285

Asn Arg Ile Phe Ser Ser Gly Phe Gly Tyr Lys Ile Arg Phe Leu Glu
    290                 295                 300

Lys Asn Asn Ile Ala Val Ser Met Ala Phe Pro Trp Lys Lys Lys Ile
305                 310                 315                 320

Asn Ser Ile Ser Val Asp Ser Asn Arg Ile Tyr Ile Thr Ile Asn His
                325                 330                 335

Glu Phe
```

<210> SEQ ID NO 8
<211> LENGTH: 9726
<212> TYPE: DNA
<213> ORGANISM: Fusobacterium necrophorum

<400> SEQUENCE: 8

```
atgagcggca tcaaaaataa cgttcagagg acaaggaaga ggatatcaga ttctaaaaaa    60
gttttaatga ttttgggatt gttgattaac actatgacgg tgagggctaa tgatacaatc   120
accgcgactg agaattttgg aacaaaaata gaaaaaaagg ataatgttta tgacattact   180
acaaacaaga ttcaagggga gaacgctttt aacagtttta atagatttgc tttaacagaa   240
aataatatag caaatctata ttttggggaa agaatagta cggggtaaa taatcttttt   300
aactttgtca atggaaaaat tgaagtagat gggattatca acggaattcg agaaaataaa   360
attggaggaa atttatattt cttaagctcg gaagggatgg cagtaggaaa aaatggagtt   420
atcaatgctg ttcttttca ttctattatt ccaaaacaag atgattttaa gaaggctttg   480
gaagaagcca acatggtaa agttttaat ggaatcattc cagtagatgg aaaagtaaaa   540
attccattga atccgaatgg aagcattacg gtagaaggaa aaatcaatgc tgttgaaggc   600
atcggtttat atgcggcgga tattagattg aaagatactg caatactaaa gacaggaatt   660
acagatttta aaaatttagt caatattagt gatcgaataa attctggtct gaccggagat   720
ttaaaagcta ccaagacaaa atctggagat attattcttt cagctcacat agattctcct   780
caaaaagcta tgggaaaaaa ttcaactgtt ggaaagagaa tagaagaata tgtaaaagga   840
aataccaaag caaatattga atctgatgct gtattggaag cagatggaaa atataaaatt   900
agtgcgaaag ctacaaatgg gagatttata agaagaag gggaaaaaga aacttataac   960
actcctttaa gttatcaga tgtggaagct tccgtaagag taaataaagg aaaagtcata  1020
ggaaagaatg ttgacattac agctgaagca agaatttct atgatgcaac tttagttact  1080
aagcttgcaa agcactcttt tagctttgtt acaggttcta tttctcctat caatttaaat  1140
ggattttag gttattgac aagtaagtcc agtgtcgtta ttggaaaaga tgccaaagtc  1200
```

```
gaagcaacag aaggaaaggc aaatattcat tcttacagtg gagtaagagc aactatggga   1260
gcagctactt ctccattaaa aattaccaat ttatatttgg agaaagccaa tggaaaactt   1320
ctcagtatcg gagcgggata tatttctgca aaaagtaatt ccaatgtaac tattgaagga   1380
gaagtaaaat cgaagggaag agcagatatt acttcaaaat ctgaaaatac tattgatgct   1440
tctgtttctg ttggaacgat gagagattcc aataaagtag ctctttcagt attggtgacg   1500
gaaggagaaa ataaatcttc cgtcaagatt gctaaggag caaaagtaga atcagaaacg    1560
gatgatgtaa atgtgagaag tgaagcgatt aattccattc gagctgctgt aaaaggtgga   1620
ttgggggata gtggtaatgg ggttgtggct gcaaatattt ctaactataa tgcttcctcc   1680
cgtatagatg tagatggata tctacatgcc aagaagcgac taaatgtgga ggctcataac   1740
attactaaaa atagtgttct gcaaacagga tctgatttgg aacttccaa gtttatgaat    1800 gatcacgttt atgaatcagg tcatctaaaa tcaattttag atgcaataaa acagcggttt   1860
ggaggagaca gtgtcaatga ggaaataaag aataagctaa cgaacttatt tagtgtcggt   1920
gtgtctgcaa ccatagcaaa tcataataat tctgcttctg tggcaatagg agagagtgga   1980
agactttctt caggagtgga agggagtaat gtaagggcat aaatgaagc tcaaaatctt    2040 cgagcgacta cgtcaagtgg aagtgtggct gtacgaaagg aagaaaaaaa gaaacttatt   2100
ggaaatgcag cagttttta tggaaactat aaaaataatg cttctgtgac aattgccgat    2160
catgctgaat tggtatcgga aggaaaaatt gatatcaaca gtgaaaataa aattgaatat   2220
aaaaatcctt caaaaatggc aaagtctgtt attgataaat tagaactttt aaagagagct   2280 tttggaaaaag aaacgaaaac tccagaatat gatccgaaag atattgaatc tattgaaaaa   2340
ttattgaatg cattttcaga aaaattggat ggaaaaccgg agcttttact aaatggtgaa   2400
agaatgacaa ttattcttcc ggatggaact tcaaaaacag gaactgctat agaaattgca   2460
aactatgttc agggagaaat gaaaaaatta gaggaaaaat taccgaaagg atttaaagct   2520
ttttcagaag gattgagtgg actgattaaa gaaactttga attttacagg agtaggaaat   2580
tatgcaaatt ttcacacttt tacctcttcc ggagctaatg gagaaagaga tgtttcttct   2640
gtgggaggag ctgtttcgtg ggtagaacag gagaattata gcaaggtatc cgttggaaaa   2700
ggagctaaac ttgctgcaaa aaagattta aatataaaag ctatcaataa agcagaaaca    2760
gtgaatttag ttgaaatat tggacttgcg agaagcagta catccggaag tgcagtcgga    2820
ggaagattaa atgttcaaag atcgaaaaat tcagctatcg tagaagctaa agaaaaagct   2880
gaattatcag gagaaaatat taatgcagat gcattgaaca gacttttca tgtagcggga    2940 tcttttaatg gtggctcagg tgggaatgca atcaatggaa tgggaagtta tagtggaggt   3000
atcagtaagg caagagtttc cattgatgac gaagcatatt tgaaagctaa taaaaaaatt   3060
gctttaaaca gtaagaatga tacttctgtt tggaatgctg ccggttcagc gggaatcgga   3120
acgaaaaatg cggcggtcgg ggttgctgtt gcggtaaatg attatgatat ttcaaacaaa   3180
gcttccattg aagataatga cgaaggacaa agtaaatatg ataagaataa agatgatgaa   3240
gtaacagtaa ctgcggaatc tttagaagta gatgcaaaaa cgaccggaac aatcaacagt   3300
atttctgttg ccggaggaat taataaggtt ggaagtaaac cgagtgaaga aaaaccgaaa   3360
tcagaagaaa gaccagaggg attttttggc aaaatcggaa acaaagtgga ctctgtaaaa   3420
aataaaatta cggatagtat ggattcatta acagaaaaaa ttacaaatta catttctgaa   3480
ggagtaaaaa aagcggggaa tcttccttcg aacgtttctc atactcccga taaggaccg    3540
```

```
tctttcagtt tgggagcttc tggaagtgtt tctttcaata atattaaaaa ggaaacatct    3600
gctgtcgtag atggagtaaa gataaatttg aagggagcaa ataaaaaggt agaggtgact    3660
tcttctgatt ctactttgt tggagcatgg ggcggatctg ctgcacttca gtggaatcat     3720
attggaagtg gaaatagcaa catcagtgct ggtttagctg gagcggctgc tgtaaataat    3780
attcaaagta aaacaagtgc tttggttaaa aatagtgata ttcgaaatgc caataaattt    3840
aaagtaaatg ctttgagtgg aggaactcaa gtagcagcag gagcaggttt ggaagcagtt    3900
aaagaaagtg gaggacaagg aaaaagttat ctattgggaa cttctgcttc tatcaactta    3960
gtgaacaatg aagtttctgc aaaatcagaa aataatacag tagcaggaga atctgaaagc    4020
caaaaaatgg atgttgatgt cactgcttat caagcggaca cccaagtgac aggagcttta    4080
aatttacaag ctggaaagtc aaatggaact gtaggggcta ctgtgactgt tgccaaatta    4140
aacaacaaag taaatgcttc tattagtggt gggagatata ctaacgttaa tcgagcggac    4200
gcaaaagctc ttttagcaac cactcaagtg actgctgcag tgacgacggg agggacaatt    4260
agttctggag cgggattagg aaattatcaa ggggctgttt ctgtcaataa gattgacaat    4320
gacgtggaag ctagcgttga taaatcttcc atcgaaggag ctaatgaaat caatgtcatt    4380
gccaaagatg tcaaaggaag ttctgatcta gcaaagaat atcaggcttt actaaatgga    4440
aaagataaaa aatatttaga agatcgtggt attaatacga ctggaaatgg ttattatacg    4500
aaggaacaac tagaaaaagc aaagaaaaaa gaaggagcgg tcattgtaaa tgctgcttta    4560
tcggttgctg gaacggataa atccgctgga ggagtagcta ttgcagtcaa tactgttaaa    4620
aataaattta aagcagaatt gagtggaagc aataaggaag ccggagagga taaaattcat    4680
gcgaaacatg taaatgtgga ggcaaaatca tctactgttg ttgtgaatgc ggcttctgga    4740
cttgctatca gcaaagatgc ttttcagga atgggatctg gagcatggca agacttatca    4800
aatgacacga ttgcaaaggt ggataaagga agaatttctg ctgattcctt aaatgtgaac    4860
gcaaataatt ccattcttgg ggtgaatgtt gcgggaacca ttgccggttc tctttctacg    4920
gcggtaggag ctgcttttgc gaataatact cttcataata aaacctctgc tttgattaca    4980
ggaacgaagg taaatccttt tagtggaaag aatacaaaag tcaatgtaca agctttgaat    5040
gattctcata ttacaaacgt ttctgctgga ggcgctgcaa gtattaagca ggctggaatc    5100
ggaggaatgg tatctgtcaa tcgtggttct gatgaaacgg aagctttagt tagtgattct    5160
gagtttgaag gagtaagttc tttcaatgta gatgcaaaag atcaaaaaac aataaataca    5220
attgccggaa atgcaaatgg aggaaaagcg gctggagttg gagcaacagt tgctcataca    5280
aatattggaa aacaatcagt tatagctatt gtaaaaaaca gtaaaattac aacggcgaat    5340
gatcaagata gaaaaaatat caatgtgact gcaaagatt atactatgac caatactata    5400
gcagtcggag ttgaggagc aaaaggagcc tctgtgcaag gagcttctgc aagtactacc    5460
ttgaataaga cagtttcttc tcatgttgat caaactgata ttgacaaaga tttagaggaa    5520
gaaaataatg gaaataagga aaaggcaaat gttaatgttc tagctgaaaa tacgagtcaa    5580
gtggtcacaa atgcgacagt gctttccgga gcaagtggac aagctgcagt aggagctgga    5640
gtagcagtta ataaaattac acaaaatact tctgcacata taaaaaatag tactcaaaat    5700
gtacgaaatg ctttggtaaa aagcaaatct cattcatcta ttaaaacaat tggaattgga    5760
gctggagttg gagctggagg agctggagtg acaggttctg tagcagtgaa taagattgta    5820
aataatacga tagcagaatt aaatcatgca aaaatcactg cgaagggaaa tgtcggagtt    5880
attacagagt ctgatgcggt aattgctaat tatgcaggaa cagtgtctgg agtggcccgt    5940
```

```
gcagcaatag gagcctcaac cagtgtgaat gaaattacag gatctacaaa agcatatgta    6000
aaagattcta cagtgattgc taaagaagaa acagatgatt atattactac tcaagggcaa    6060
gtagataaag tggtagataa agtattcaaa aatcttaata ttaacgaaga cttatcacaa    6120
aaaagaaaaa taagtaataa aaaaggattt gttaccaata gttcagctac tcatacttta    6180
aaatctttat tggcaaatgc cgctggttca ggacaagccg gagtggcagg aactgttaat    6240
atcaacaagg tttatggaga aacagaagct cttgtagaaa attctatatt aaatgcaaaa    6300
cattattctg taaaatcagg agattacacg aattcaatcg gagtagtagg ttctgttggt    6360
gttggtggaa atgtaggagt aggagcttct tctgatacca atattataaa aagaaatacc    6420
aagacaagag ttggaaaaac tacaatgtct gatgaaggtt tcggagaaga agctgaaatt    6480
acagcagatt ctaagcaagg aatttcctct tttggagtcg gagtcgcagc agccggggta    6540
ggagccggag tggcaggaac cgtttccgta aatcaatttg caggaaagac ggaagtagat    6600
gtggaagaag caaagatttt ggtaaaaaaa gctgagatta cagcaaaacg ttatagttct    6660
gttgcaattg gaaatgccgc agtcggagtg gctgcaaaag gagctggaat tggagcagca    6720
gtggcagtta ccaaagatga atcaaacacg agagcaagag tgaaaaattc taaaattatg    6780
actcgaaaca gttagatgt aatagcagaa aatgagataa aatcaggtac tggaatcggt    6840
```

```
atttctaaag tagaaggttt ggatgaagat aaagtaactg ctaaatcttc tgtagtatca    8340
ggaaatggag gaggaattgc cggagcagga gtgaatactt ctacagcaca aagtaatact    8400
gaatccgtag ttcgtttacg aaagcaagat tatgaaaata atgattacac aaaaaaatat    8460
atttcagaag tcaatgctct tgctttaaat gatacaaaga atgaagcgaa tatagaatct    8520
ttagcggtag ccggtgtgca tgcacaagga acaaacaaag catttacgag atcaaacaag    8580
ttaacttcta caactgtaaa tggaggaaac gtatctcaac ttcgtgcaaa agctttggct    8640
aaaaatgaaa attatggaaa tgtaaaagga actggaggag ccttagtcgg agcggaaaca    8700
gcagccgttg aaaattatac aaagagtact acaggagcat tggttgcagg aaattgggaa    8760
attggagata aattagaaac gattgcaaga gataatacga ttgtaagagt caacggagac    8820
ggaaccaaag gaggtcttgt cggaaagaat ggtatttctg tgaaaaatac aatttcaggg    8880
gaaacaaaat catccattga agataaagcc agaattgttg gaaccggaag tgtaaatgta    8940
gatgctttga tgaacttgac tgtagatcta caaggaaaaa gtggtggcta tggtggaatt    9000
ggtattggaa atgttgatgt aaataatgtg attaagaaaa atgtagaagc caaaatcgga    9060
agacatgcta ttgtagaaac tactggaaaa caagaatatc aagcatttac aagagcaaaa    9120
gtaaatattc ttggaaaagg agacgctgca gctgcagctg caatatcgaa tgtacacatt    9180
tccaatgaga tggatattaa aaatttggca aagcagtatg catcttctca attaataacc    9240
aaaaattcaa aaataatat tactttagca tcaagtagtg aatcgaatgt gaatgttcat    9300
ggggtggctg aagcaagagg tgcaggagcc aaagcgacag ttagtgtaaa gaatcaaata    9360
aatagaacta ataatgttga tttagcagga aaaattaaaa cagagggaaa catcaatgta    9420
tatgccggat atgataaaaa ttataatata agtaagacaa attctaaggc tattgcggat    9480
gccaaaagtc atgctgcagc tgcttcggca actgccacta ttgaaaaaaa tgaagtaaaa    9540
tttaataatg cgatccgaga atttaaaaat aatctggcaa gattggaagg gaaagctaat    9600
aaaaaaacgt cggtaggatc taatcaggta gactggtata cggataaata tacatggcat    9660
tcttctgaaa aagcatacaa aaaattgaca tatcaatcaa agagaggaga aaagggaaa    9720 aaatga                                                              9726
```

<210> SEQ ID NO 9
<211> LENGTH: 1130
<212> TYPE: DNA
<213> ORGANISM: Fusobacterium necrophorum

<400> SEQUENCE: 9

```
atgagcggca tcaaaaataa cgttcagagg acaaggaaga ggatatcaga ttctaaaaaa     60
gttttaatga ttttgggatt gttgattaac actatgacgg tgagggctaa tgatacaatc    120
accgcgactg agaattttgg aacaaaaata gaaaaaaagg ataatgttta tgacattact    180
acaaacaaga ttcaagggga gaacgctttt aacagtttta atagatttgc tttaacagaa    240
aataatatag caaatctata ttttggggaa aagaatagta cgggggtaaa taatcttttt    300
aactttgtca atgaaaaaat tgaagtagat gggattatca acggaattcg agaaaataaa    360
attggaggaa atttatattt cttaagctcg gaagggatgg cagtaggaaa aaatggagtt    420
atcaatgctg gttcttttca ttctattatt ccaaaacaag atgattttaa gaaggctttg    480
gaagaagcca acatggtaa agtttttaat ggaatcattc cagtagatgg aaaagtaaaa    540
attccattga atccgaatgg aagcattacg gtagaaggaa aaatcaatgc tgttgaaggc    600
atcggtttat atgcggcgga tattagattg aaagatactg caatactaaa gacaggaatt    660
```

| | |
|---|---:|
| acagatttta aaaatttagt caatattagt gatcgaataa attctggtct gaccggagat | 720 |
| ttaaaagcta ccaagacaaa atctggagat attattcttt cagctcacat agattctcct | 780 |
| caaaaagcta tgggaaaaaa ttcaactgtt ggaaagagaa tagaagaata tgtaaaagga | 840 |
| aataccaaag caaatattga atctgatgct gtattggaag cagatggaaa tataaaaatt | 900 |
| agtgcgaaag ctacaaatgg gagatttata agaaagaag gggaaaaaga aacttataac | 960 |
| actcctttaa gtttatcaga tgtggaagct tccgtaagag taaataaagg aaaagtcata | 1020 |
| ggaaagaatg ttgacattac agctgaagca aagaatttct atgatgcaac tttagttact | 1080 |
| aagcttgcaa agcactcttt tagctttgtt acaggttcta tttctcctat | 1130 |

<210> SEQ ID NO 10
<211> LENGTH: 2780
<212> TYPE: DNA
<213> ORGANISM: Fusobacterium necrophorum

<400> SEQUENCE: 10

| | |
|---|---:|
| gggagattta taaagaaaga aggggaaaaa gaaacttata acactccttt aagtttatca | 60 |
| gatgtggaag cttccgtaag agtaaataaa ggaaaagtca taggaaagaa tgttgacatt | 120 |
| acagctgaag caaagaattt ctatgatgca actttagtta ctaagcttgc aaagcactct | 180 |
| tttagctttg ttacaggttc tatttctcct atcaatttaa atggattttt aggtttattg | 240 |
| acaagtaagt ccagtgtcgt tattggaaaa gatgccaaag tcgaagcaac agaaggaaag | 300 |
| gcaaatattc attcttacag tggagtaaga gcaactatgg gagcagctac ttctccatta | 360 |
| aaaattacca atttatattt ggagaaagcc aatggaaaac ttctcagtat cggagcggga | 420 |
| tatatttctg caaaagtaa ttccaatgta actattgaag agaagtaaa atcgaaggga | 480 |
| agagcagata ttacttcaaa atctgaaaat actattgatg cttctgtttc tgttggaacg | 540 |
| atgagagatt ccaataaagt agctctttca gtattggtga cggaaggaga aaataaatct | 600 |
| tccgtcaaga ttgctaaagg agcaaaagta gaatcagaaa cggatgatgt aaatgtgaga | 660 |
| agtgaagcga ttaattccat tcgagctgct gtaaaaggtg gattggggga tagtggtaat | 720 |
| ggggttgtgg ctgcaaatat ttctaactat aatgcttcct cccgtataga tgtagatgga | 780 |
| tatctacatg ccaagaagcg actaaatgtg gaggctcata acattactaa aaatagtgtt | 840 |
| ctgcaaacag atctgatttt ggaacttcc aagtttatga atgatcacgt ttatgaatca | 900 |
| ggtcatctaa aatcaatttt agatgcaata aaacagcggt ttggaggaga cagtgtcaat | 960 |
| gaggaaataa agaataagct aacgaactta tttagtgtcg gtgtgtctgc aaccatagca | 1020 |
| aatcataata attctgcttc tgtggcaata ggagagagtg gaagactttc ttcaggagtg | 1080 |
| gaagggagta atgtaagggc attaaatgaa gctcaaaatc ttcgagcgac tacgtcaagt | 1140 |
| ggaagtgtgg ctgtacgaaa ggaagaaaaa agaaactta ttggaaatgc agcagttttt | 1200 |
| tatggaaact ataaaaataa tgcttctgtg acaattgccg atcatgctga attggtatcg | 1260 |
| gaaggaaaaa ttgatatcaa cagtgaaaat aaaattgaat ataaaaatcc ttcaaaaatg | 1320 |
| gcaaagtctg ttattgataa attagaactt ttaaagagag cttttggaaa agaaacgaaa | 1380 |
| actccagaat atgatccgaa agatattgaa tctattgaaa aattattgaa tgcatttttca | 1440 |
| gaaaaattgg atgaaaaacc ggagctttta ctaaatggtg aaagaatgac aattattctt | 1500 |
| ccggatggaa cttcaaaaac aggaactgct atagaaattg caaactatgt tcagggagaa | 1560 |
| atgaaaaaat tagaggaaaa attaccgaaa ggatttaaag cttttttcaga aggattgagt | 1620 |

```
ggactgatta aagaaacttt gaatttttaca ggagtaggaa attatgcaaa ttttcacact    1680
tttacctctt ccggagctaa tggagaaaga gatgtttctt ctgtgggagg agctgtttcg    1740
tgggtagaac aggagaatta tagcaaggta tccgttggaa aaggagctaa acttgctgca    1800
aaaaaagatt taaatataaa agctatcaat aaagcagaaa cagtgaattt agttggaaat    1860
attggacttg cgagaagcag tacatccgga agtgcagtcg gaggaagatt aaatgttcaa    1920
agatcgaaaa attcagctat cgtagaagct aaagaaaaag ctgaattatc aggagaaaat    1980
attaatgcag atgcattgaa cagacttttt catgtagcgg gatctttaa tggtggctca     2040 ggtgggaatg caatcaatgg aatgggaagt tatagtggag gtatcagtaa ggcaagagtt    2100
tccattgatg acgaagcata tttgaaagct aataaaaaaa ttgcttttaaa cagtaagaat   2160 gatacttctg tttggaatgc tgccggttca gcgggaatcg gaacgaaaaa tgcggcggtc    2220
ggggttgctg ttgcggtaaa tgattatgat atttcaaaca aagcttccat tgaagataat    2280
gacgaaggac aaagtaaata tgataagaat aaagatgatg aagtaacagt aactgcggaa    2340
tctttagaag tagatgcaaa aacgaccgga acaatcaaca gtatttctgt tgccggagga    2400
attaataagg ttggaagtaa accgagtgaa gaaaaaccga aatcagaaga aagaccagag    2460
ggattttttg gcaaaatcgg aaacaaagtg gactctgtaa aaaataaaat tacggatagt    2520
atggattcat taacagaaaa aattacaaat tacatttctg aaggagtaaa aaaagcgggg    2580
aatcttcctt cgaacgtttc tcatactccc gataaaggac cgtctttcag tttgggagct    2640
tctggaagtg tttcttttcaa taatattaaa aggaaacat ctgctgtcgt agatggagta    2700
aagataaatt tgaagggagc aaataaaaag gtagaggtga cttcttctga ttctactttt   2760
gttggagcat ggggcggatc                                                2780

<210> SEQ ID NO 11
<211> LENGTH: 2141
<212> TYPE: DNA
<213> ORGANISM: Fusobacterium necrophorum

<400> SEQUENCE: 11
ggagcttctg gaagtgtttc tttcaataat attaaaaagg aaacatctgc tgtcgtagat     60
ggagtaaaga taaatttgaa gggagcaaat aaaaaggtag aggtgacttc ttctgattct    120
acttttgttg gagcatgggg cggatctgct gcacttcagt ggaatcatat tggaagtgga    180
aatagcaaca tcagtgctgg tttagctgga gcggctgctg taaataatat tcaaagtaaa    240
acaagtgctt tggttaaaaa tagtgatatt cgaaatgcca ataaatttaa agtaaatgct    300
ttgagtggag gaactcaagt agcagcagga gcaggtttgg aagcagttaa agaaagtgga    360
ggacaaggaa aaagttatct attgggaact tctgcttcta tcaacttagt gaacaatgaa    420
gtttctgcaa atcagaaaa taatacagta gcaggagaat ctgaaagcca aaaaatggat    480
gttgatgtca ctgcttatca agcggacacc caagtgacag gagcttttaaa tttacaagct   540 ggaaagtcaa atggaactgt agggggctact gtgactgttg ccaaattaaa caacaaagta    600
aatgcttcta ttagtggtgg gagatatact aacgttaatc gagcggacgc aaaagctctt    660
ttagcaacca ctcaagtgac tgctgcagtg acgacgggag ggacaattag ttctggagcg    720
ggattaggaa attatcaagg ggctgtttct gtcaataaga ttgacaatga cgtgaaagct    780
agcgttgata aatcttccat cgaaggagct aatgaaatca atgtcattgc caaagatgtc    840
aaaggaagtt ctgatctagc aaaagaatat caggctttac taaatggaaa agataaaaaa    900
tatttagaag atcgtggtat taatacgact ggaaatggtt attatacgaa ggaacaacta    960
```

```
gaaaaagcaa agaaaaaaga aggagcggtc attgtaaatg ctgctttatc ggttgctgga      1020
acggataaat ccgctggagg agtagctatt gcagtcaata ctgttaaaaa taaatttaaa      1080
gcagaattga gtggaagcaa taaggaagcc ggagaggata aaattcatgc gaaacatgta      1140
aatgtggagg caaaatcatc tactgttgtt gtgaatgcgg cttctggact tgctatcagc      1200
aaagatgctt tttcaggaat gggatctgga gcatggcaag acttatcaaa tgacacgatt      1260
gcaaaggtgg ataaaggaag aatttctgct gattccttaa atgtgaacgc aaataattcc      1320
attcttgggg tgaatgttgc gggaaccatt gccggttctc tttctacggc ggtaggagct      1380
gcttttgcga ataatactct tcataataaa acctctgctt tgattacagg aacgaaggta      1440
aatcctttta gtggaaagaa tacaaaagtc aatgtacaag ctttgaatga ttctcatatt      1500
acaaacgttt ctgctggagg cgctgcaagt attaagcagg ctggaatcgg aggaatggta      1560
tctgtcaatc gtggttctga tgaaacgaa gctttagtta gtgattctga gtttgaagga      1620
gtaagttctt tcaatgtaga tgcaaaagat caaaaaacaa taaatacaat tgccggaaat      1680
gcaaatggag aaaagcggc tggagttgga gcaacagttg ctcatacaaa tattggaaaa      1740
caatcagtta tagctattgt aaaaaacagt aaaattacaa cggcgaatga tcaagataga      1800
aaaaatatca atgtgactgc aaaagattat actatgacca atactatagc agtcggagtt      1860
ggaggagcaa aaggagcctc tgtgcaagga gcttctgcaa gtactacctt gaataagaca      1920
gtttcttctc atgttgatca aactgatatt gacaaagatt tagaggaaga aaataatgga      1980
aataaggaaa aggcaaatgt taatgttcta gctgaaaata cgagtcaagt ggtcacaaat      2040
gcgacagtgc tttccggagc aagtggacaa gctgcagtag gagctggagt agcagttaat      2100
aaaattacac aaaatacttc tgcacatata aaaaatagta c                         2141

<210> SEQ ID NO 12
<211> LENGTH: 1887
<212> TYPE: DNA
<213> ORGANISM: Fusobacterium necrophorum

<400> SEQUENCE: 12
ctgcagtagg agctggagta gcagttaata aaattacaca aaatacttct gcacatataa       60
aaaatagtac tcaaaatgta cgaaatgctt tggtaaaaag caaatctcat tcatctatta      120
aaacaattgg aattggagct ggagttggag ctggaggagc tggagtgaca ggttctgtag      180
cagtgaataa gattgtaaat aatacgatag cagaattaaa tcatgcaaaa atcactgcga      240
agggaaatgt cggagttatt acagagtctg atgcggtaat tgctaattat gcaggaacag      300
tgtctggagt ggcccgtgca gcaataggag cctcaaccag tgtgaatgaa attacaggat      360
ctacaaaagc atatgtaaaa gattctacag tgattgctaa agaagaaaca gatgattata      420
ttactactca agggcaagta gataaagtgg tagataaagt attcaaaaat cttaatatta      480
acgaagactt atcacaaaaa agaaaaataa gtaataaaaa aggatttgtt accaatagtt      540
cagctactca tactttaaaa tctttattgg caaatgccgc tggttcagga caagccggag      600
tggcaggaac tgttaatatc aacaaggttt atggagaaac agaagctctt gtagaaaatt      660
ctatattaaa tgcaaaacat tattctgtaa atcaggaga ttacgcgaat tcaatcggag      720
tagtaggttc tgttggtgtt ggtggaaatg taggagtagg agcttcttct gataccaata      780
ttataaaaag aaataccaag acaagagttg gaaaaactac aatgtctgat gaaggtttcg      840
gagaagaagc tgaaattaca gcagattcta agcaaggaat ttcctctttt ggagtcggag      900
```

```
tcgcagcagc cggggtagga gccggagtgg caggaaccgt ttccgtaaat caatttgcag    960
gaaagacgga agtagatgtg aagaagcaa agattttggt aaaaaaagct gagattacag   1020
caaaacgtta tagttctgtt gcaattggaa atgccgcagt cggagtggct gcaaaaggag   1080
ctggaattgg agcagcagtg gcagttacca agatgaatc aaacacgaga gcaagagtga   1140
aaaattctaa aattatgact cgaaacaagt tagatgtaat agcagaaaat gagataaaat   1200
caggtactgg aatcggttca gccggagctg gaattcttgc agccggagta tctggagtgg   1260
tttctgtcaa taatattgca ataaggtag aaacagatat cgatcatagt actttacact   1320
cttctactga tgtaaatgta aaagctctta ataaaatttc gaattccttg acagccggtg   1380
gaggagccgc aggtcttgca gcagttaccg gagtggtttc tgttaacact ataaatagtt   1440
ctgtgatagc tcgagttcac aataactctg atttgacttc cgtacgagaa aaagtaaatg   1500
taacggcaaa agaggaaaaa aatattaagc aaacagcagc aaatgcagga atcggaggag   1560
cagcaatcgg agccaatgtc ttggtaaata attttggaac agctgtagaa gatagaaaaa   1620
attctgaagg aaaaggaaca gaagttttaa aaactttaga cgaagttaac aaagaacaag   1680
ataaaaaagt aaatgatgct acgaaaaaaa tcttacaatc agcaggtatt tctacagaag   1740
atacttctgt aaaagcggat agaggagata ctcagggaga aggaattaaa gccattgtga   1800
agacttctga tattattgga aaaaatgtag atattacaac agaggacaag aataatatca   1860
cttctactgg tggtttggga actgcag                                       1887

<210> SEQ ID NO 13
<211> LENGTH: 2322
<212> TYPE: DNA
<213> ORGANISM: Fusobacterium necrophorum

<400> SEQUENCE: 13
ggaattaaag ccattgtgaa gacttctgat attattggaa aaaatgtaga tattacaaca     60
gaggacaaga ataatatcac ttctactggt ggtttgggaa ctgcaggtct tgcttccgca    120
tcaggaacag tggcagttac aaatattaaa agaaattccg gagttactgt tgaaaattct    180
tttgtgaaag cagctgaaaa agtaaatgtt agatcggata ttacaggaaa tgttgcttta    240
acagcatatc aagtcctgt aggagcattg gaataggag ctgcctatgc agaattaaat    300
tctaatggaa gatcaaatat cagtattaaa aattctaagc tattaggaaa aaatattgat    360
gttattgtaa aagataaatc ggaattgaga gcggaagcaa aaggattaac cgtaggagcg    420
gtagctgccg gagccattat ctcaaaagca agaatgaaa tgaattcaga ggttgaaatt    480
gagaagagta ttttcaatga agaaaataga gtaactagcc cttctaaagg aattggaaga    540
gaaatcaatg tcaaagtgga aaaagaaaac agagtgactg ctgaatctca aggagcttct    600
gtaggagcag tagcaggggc aggaattatt tccgaagcaa aagatgccgg aagctcttat    660
ttgaaagtta gtacaaaatc cggaagaagt atttttcatg cagataatgt gaatatggaa    720
gcaacacata aaatgaaagt aacagcagtt tctaaagcag taacaggttc tgtattggga    780
ggagttggag tcaccaaggc agaagctact gctgcaggta aaactatggt agaagttgag    840
gaaggaaatt tgttcagaac aaatcgattg aatgcaattt ctaaagtaga aggtttggat    900
gaagataaag taactgctaa atcttctgta gtatcaggaa atggaggagg aattgccgga    960
gcaggagtga atacttctac agcacaaagt aatactgaat ccgtagttcg tttacgaaag   1020
caagattatg aaaataatga ttacacaaaa aaatatattt cagaagtcaa tgctcttgct   1080
ttaaatgata caaagaatga agcgaatata gaatctttag cggtagccgg tgtgcatgca   1140
```

```
caaggaacaa acaaagcatt tacgagatca acaagttaa cttctacaac tgtaaatgga      1200
ggaaacgtat ctcaacttcg tgcaaaagct ttggctaaaa atgaaaatta tggaaatgta      1260
aaaggaactg gaggagcctt agtcggagcg gaaacagcag ccgttgaaaa ttatacaaag      1320
agtactacag gagcattggt tgcaggaaat tgggaaattg gagataaatt agaaacgatt      1380
gcaagagata tacgattgt aagagtcaac ggagacggaa ccaaaggagg tcttgtcgga      1440
aagaatggta tttctgtgaa aaatacaatt tcaggggaaa caaaatcatc cattgaagat      1500
aaagccagaa ttgttggaac cggaagtgta aatgtagatg ctttgaatga acttgatgta      1560
gatctacaag gaaaaagtgg tggctatggt ggaattggta ttggaaatgt tgatgtaaat      1620
aatgtgatta gaaaaatgt agaagccaaa atcggaagac atgctattgt agaaactact      1680
ggaaaacaag aatatcaagc atttacaaga gcaaagtaa atattcttgg aaaaggagac      1740
gctgcagctg cagctgcaat atcgaatgta cacatttcca atgagatgga tattaaaaat      1800
ttggcaaagc agtatgcatc ttctcaatta ataaccaaaa attcaaaaaa taatattact      1860
ttagcatcaa gtagtgaatc gaatgtgaat gttcatgggg tggctgaagc aagaggtgca      1920
ggagccaaag cgacagttag tgtaaagaat caaataaata gaactaataa tgttgattta      1980
gcaggaaaaa ttaaaacaga gggaaacatc aatgtatatg ccggatatga taaaaattat      2040
aatataagta agacaaattc taaggctatt gcggatgcca aaagtcatgc tgcagctgct      2100
tcggcaactg ccactattga aaaaaatgaa gtaaaattta ataatgcgat ccgagaattt      2160
aaaaataatc tggcaagatt ggaagggaaa gctaataaaa aaacgtcggt aggatctaat      2220
caggtagact ggtatacgga taaatataca tggcattctt ctgaaaaagc atacaaaaaa      2280
ttgacatatc aatcaaagag aggagaaaaa gggaaaaaat ga                        2322

<210> SEQ ID NO 14
<211> LENGTH: 1017
<212> TYPE: DNA
<213> ORGANISM: Fusobacterium necrophorum

<400> SEQUENCE: 14
atcaatatgg cttccggaaa agttccggga acgaccgatt attttgtgca aatctatgaa        60
ccaaaaagac agcagttttt tgtttttgca gataatttag acaaaaaaa tacaggagaa       120 ttacgatggg ggctaaatta tattaataat agtgttacag gaaacagaga tcaactgtct       180
cttacctctt tagtaacaga aggaacggct tctctatctt cttttttatac ttttcctgtt       240 tctaaaaaag gaaccaaaat atcactacaa cattctgtag gaaagttgaa acatatacaa       300 gggggctttaa agcataaaat aactggaaac tcttatagtt atggggttgg aatagttcat       360
cctattctgg ttcatgaaaa aaataaagta gaactttcct tggattgggt aaaacaaagg       420
actgttacag atctattgaa attgaaatgg gtaaataata gactttctaa gtatacagcg       480
ggaattggaa taagccatta tgaggaagat agtgttttct atacaaagca aaatattaca       540
aagggaaaat ttattccaat ttcgggagat gcaagaaatt atacaaagta tgatatgttt       600
ctaatatatc agaaaaactt gaaatataac actttagtaa cactaaagat ggcagggcaa       660
tattctctga gtaaaaaatt accctctgtc gagcaaattt atgcaggagg agcctataat       720
gttcgtggtt atccggaaaa ttttatggga gctgaacacg gagttttttt caatgctgaa       780 ttatcaaat tagtagagaa taaggagaa ttttttgttt tttagatgg ggcttctctt        840 catggagaga gtgcttggca ggaaaataga attttagct caggttttgg atataaaata       900
```

-continued

```
aggttttag aaaaaaataa tattgctgtt agcatggcat ttccatggaa gaaaaaaata    960
aatagtattt cagtagattc taatcgaatc tatattacaa taaatcatga atttttaa   1017
```

<210> SEQ ID NO 15
<211> LENGTH: 11130
<212> TYPE: DNA
<213> ORGANISM: Fusobacterium necrophorum

<400> SEQUENCE: 15

```
gatcaatatg gcttccggaa aagttccggg aacgaccgat tattttgtgc aaatctatga     60
accaaaaaga cagcagtttt ttgttttttgc agataaatta ggacaaaaaa atacaggaga   120
attacgatgg gggctaaatt atattaataa tagtgttaca ggaaacagag atcaactgtc   180
tcttacctct ttagtaacag aaggaacggc ttctctatct tcttttttata cttttcctgt   240
ttctaaaaaa ggaaccaaaa tatcactaca acattctgta ggaaagttga aacatataca   300
aggggcttta aagcataaaa taactggaaa ctcttatagt tatggggttg gaatagttca   360
tcctattctg gttcatgaaa aaaataaagt agaactttcc ttggattggg taaaacaaag   420
gactgttaca gatctattga aattgaaatg ggtaaataat agactttcta agtatacagc   480
gggaattgga ataagccatt atgaggaaga tagtgttttc tatacaaagc aaaatattac   540
aaagggaaaa tttattccaa tttcgggaga tgcaagaaat tatacaaagt atgatatgtt   600
tctaatatat cagaaaaact tgaaatataa cactttagta acactaaaga tggcagggca   660
atattctctg agtaaaaaat taccctctgt cgagcaaatt tatgcaggag agcctataa   720
tgttcgtggt tatccggaaa attttatggg agctgaacac ggagtttttt tcaatgctga   780
attatcaaaa ttagtagaga ataaaggaga atttttttgtt ttttttagatg ggcttctct   840
tcatggagag agtgcttggc aggaaaatag aattttttagc tcaggttttg gatataaaat   900
aaggttttta gaaaaaaata atattgctgt tagcatggca tttccatgga agaaaaaaat   960
aaatagtatt tcagtagatt ctaatcgaat ctatattaca ataaatcatg aattttaaag  1020
ggggtaagac aaaatgagcg gcatcaaaaa taacgttcag aggacaagga agaggatatc  1080
agattctaaa aaagttttaa tgattttggg attgttgatt aacactatga cggtgagggc  1140
taatgataca atcaccgcga ctgagaattt tggaacaaaa atagaaaaaa aggataatgt  1200
ttatgacatt actacaaaca agattcaagg ggagaacgct tttaacagtt ttaatagatt  1260
tgctttaaca gaaaataata tagcaaatct atattttggg gaaaagaata gtacggggggt  1320
aaataatctt tttaactttg tcaatggaaa aattgaagta gatgggatta tcaacggaat  1380
tcgagaaaat aaaaattgga gg gaaatttata tttcttaagc tcggaaggga tggcagtagg  1440
aaaaaatgga gttatcaatg ctggttcttt tcattctatt attccaaaac aagatgattt  1500
taagaaggct ttggaagaag ccaaacatgg taaagtttt aatggaatca ttccagtaga  1560
tggaaaagta aaaattccat tgaatccgaa tggaagcatt acgtagaag gaaaaatcaa  1620
tgctgttgaa ggcatcggtt tatatgcggc ggatattaga ttgaaagata ctgcaatact  1680
aaagacagga attacagatt ttaaaaattt agtcaatatt agtgatcgaa taaattctgg  1740
tctgaccgga gatttaaaag ctaccaagac aaaatctgga gatattattc tttcagctca  1800
catagattct cctcaaaaag ctatgggaaa aaattcaact gttggaaaga aatagaaga  1860
atatgtaaaa ggaaatacca aagcaaatat tgaatctgat gctgtattgg aagcagatgg  1920
aaatataaaa attagtgcga aagctacaaa tgggagattt ataagaaag aaggggaaaa  1980
agaaacttat aacactcctt taagtttatc agatgtggaa gcttccgtaa gagtaaataa  2040
```

```
aggaaaagtc ataggaaaga atgttgacat tacagctgaa gcaaagaatt tctatgatgc    2100
aactttagtt actaagcttg caaagcactc ttttagcttt gttacaggtt ctatttctcc    2160
tatcaattta aatggatttt taggtttatt gacaagtaag tccagtgtcg ttattggaaa    2220
agatgccaaa gtcgaagcaa cagaaggaaa ggcaaatatt cattcttaca gtggagtaag    2280
agcaactatg ggagcagcta cttctccatt aaaaattacc aatttatatt tggagaaagc    2340
caatggaaaa cttctcagta tcggagcggg atatatttct gcaaaagta attccaatgt     2400 aactattgaa ggagaagtaa aatcgaaggg aagagcagat attacttcaa atctgaaaa     2460 tactattgat gcttctgttt ctgttggaac gatgagagat tccaataaag tagctctttc    2520
agtattggtg acggaaggag aaaataaatc ttccgtcaag attgctaaag gagcaaaagt    2580
agaatcagaa acggatgatg taaatgtgag aagtgaagcg attaattcca ttcgagctgc    2640
tgtaaaaggt ggattggggg atagtggtaa tggggttgtg gctgcaaata tttctaacta    2700
taatgcttcc tcccgtatag atgtagatgg atatctacat gccaagaagc gactaaatgt    2760
ggaggctcat aacattacta aaaatagtgt tctgcaaaca ggatctgatt tgggaacttc    2820
caagtttatg aatgatcacg tttatgaatc aggtcatcta aaatcaattt tagatgcaat    2880
aaaacagcgg tttggaggag acagtgtcaa tgaggaaata aagaataagc taacgaactt    2940
atttagtgtc ggtgtgtctg caaccatagc aaatcataat aattctgctt ctgtggcaat    3000
aggagagagt ggaagacttt cttcaggagt ggaagggagt aatgtaaggg cattaaatga    3060
agctcaaaat cttcgagcga ctacgtcaag tggaagtgtg gctgtacgaa aggaagaaaa    3120
aaagaaactt attggaaatg cagcagtttt ttatgaaaac tataaaaata atgcttctgt    3180
gacaattgcc gatcatgctg aattggtatc ggaaggaaaa attgatatca acagtgaaaa    3240
taaaattgaa tataaaaatc cttcaaaaat ggcaaagtct gttattgata aattagaact    3300
tttaaagaga gcttttggaa aagaaacgaa aactccagaa tatgatccga aagatattga    3360
atctattgaa aaattattga atgcattttc agaaaaattg gatggaaaac cggagctttt    3420
actaaatggt gaaagaatga caattattct tccggatgga acttcaaaaa caggaactgc    3480
tatagaaatt gcaaactatg ttcagggaga aatgaaaaaa ttagaggaaa aattaccgaa    3540
aggatttaaa gcttttcag aaggattgag tggactgatt aaagaaactt tgaattttac    3600
aggagtagga aattatgcaa attttcacac ttttacctct tccggagcta atggagaaag    3660
agatgtttct tctgtgggag gagctgtttc gtgggtagaa caggagaatt atagcaaggt    3720
atccgttgga aaaggagcta aacttgctgc aaaaaagat ttaaatataa aagctatcaa    3780
taaagcagaa acagtgaatt tagttggaaa tattggactt gcgagaagca gtacatccgg    3840
aagtgcagtc ggaggaagat taaatgttca aagatcgaaa aattcagcta tcgtagaagc    3900
taaagaaaaa gctgaattat caggagaaaa tattaatgca gatgcattga acagactttt    3960
tcatgtagcg ggatctttta atggtggctc aggtgggaat gcaatcaatg gaatgggaag    4020
ttatagtgga ggtatcagta aggcaagagt ttccattgat gacgaagcat atttgaaagc    4080
taataaaaaa attgctttaa acagtaagaa tgatacttct gtttggaatg ctgccggttc    4140
agcgggaatc ggaacgaaaa atgcggcggt cggggttgct gttgcggtaa atgattatga    4200
tatttcaaac aaagcttcca ttgaagataa tgacgaagga caaagtaaat atgataagaa    4260
taaagatgat gaagtaacag taactgcgga atctttagaa gtagatgcaa aaacgaccgg    4320
aacaatcaac agtatttctg ttgccggagg aattaataag gttggaagta aaccgagtga    4380
```

```
agaaaaaccg aaatcagaag aaagaccaga gggattttt ggcaaaatcg gaaacaaagt    4440
ggactctgta aaaaataaaa ttacggatag tatggattca ttaacagaaa aaattacaaa    4500
ttacatttct gaaggagtaa aaaaagcggg gaatcttcct tcgaacgttt ctcatactcc    4560
cgataaagga ccgtctttca gtttgggagc ttctggaagt gtttctttca ataatattaa    4620
aaaggaaaca tctgctgtcg tagatggagt aaagataaat ttgaagggag caaataaaaa    4680
ggtagaggtg acttcttctg attctacttt tgttggagca tggggcggat ctgctgcact    4740
tcagtggaat catattggaa gtggaaatag caacatcagt gctggtttag ctggagcggc    4800
tgctgtaaat aatattcaaa gtaaaacaag tgctttggtt aaaaatagtg atattcgaaa    4860
tgccaataaa tttaaagtaa atgctttgag tggaggaact caagtagcag caggagcagg    4920 tttgaagca gttaaagaaa gtggaggaca aggaaaaagt tatctattgg gaacttctgc    4980
ttctatcaac ttagtgaaca atgaagtttc tgcaaaatca gaaaataata cagtagcagg    5040
agaatctgaa agccaaaaaa tggatgttga tgtcactgct tatcaagcgg acacccaagt    5100
gacaggagct ttaaatttac aagctggaaa gtcaaatgga actgtagggg ctactgtgac    5160
tgttgccaaa ttaaacaaca aagtaaatgc ttctattagt ggtgggagat atactaacgt    5220
taatcgagcg gacgcaaaag ctcttttagc aaccactcaa gtgactgctg cagtgacgac    5280
gggagggaca attagttctg gagcgggatt aggaaattat caaggggctg tttctgtcaa    5340
taagattgac aatgacgtgg aagctagcgt tgataaatct tccatcgaag gagctaatga    5400
aatcaatgtc attgccaaag atgtcaaagg aagttctgat ctagcaaaag aatatcaggc    5460
tttactaaat ggaaaagata aaaaatattt agaagatcgt ggtattaata cgactggaaa    5520
tggttattat acgaaggaac aactagaaaa agcaaagaaa aaagaaggag cggtcattgt    5580
aaatgctgct ttatcggttg ctggaacgga taaatccgct ggaggagtag ctattgcagt    5640
caatactgtt aaaaataaat ttaaagcaga attgagtgga agcaataagg aagccggaga    5700
ggataaaatt catgcgaaac atgtaaatgt ggaggcaaaa tcatctactg ttgttgtgaa    5760
tgcggcttct ggacttgcta tcagcaaaga tgcttttca ggaatgggat ctggagcatg    5820
gcaagactta tcaaatgaca cgattgcaaa ggtggataaa ggaagaattt ctgctgattc    5880
cttaaatgtg aacgcaaata attccattct tggggtgaat gttgcgggaa ccattgccgg    5940
ttctctttct acggcggtag gagctgcttt tgcgaataat actcttcata taaaacctc    6000 tgctttgatt acaggaacga aggtaaatcc ttttagtgga aagaatacaa aagtcaatgt    6060
acaagctttg aatgattctc atattacaaa cgtttctgct ggaggcgctg caagtattaa    6120
gcaggctgga atcggaggaa tggtatctgt caatcgtggt tctgatgaaa cggaagcttt    6180
agttagtgat tctgagtttg aaggagtaag ttctttcaat gtagatgcaa aagatcaaaa    6240
aacaataaat acaattgccg gaaatgcaaa tggaggaaaa gcggctggag ttggagcaac    6300
agttgctcat acaaatattg gaaaacaatc agttatagct attgtaaaaa acagtaaaat    6360
tacaacggcg aatgatcaag atagaaaaaa tatcaatgtg actgcaaaag attatactat    6420
gaccaatact atagcagtcg gagttggagg agcaaaagga gcctctgtgc aaggagcttc    6480
tgcaagtact accttgaata agacagtttc ttctcatgtt gatcaaactg atattgacaa    6540
agatttagag gaagaaaata atggaaataa ggaaaaggca aatgttaatg ttctagctga    6600
aaatacgagt caagtggtca caaatgcgac agtgctttcc ggagcaagtg gacaagctgc    6660
agtaggagct ggagtagcag ttaataaaat tacacaaaat acttctgcac atataaaaaa    6720
tagtactcaa aatgtacgaa atgctttggt aaaaagcaaa tctcattcat ctattaaaac    6780
```

```
aattggaatt ggagctggag ttggagctgg aggagctgga gtgacaggtt ctgtagcagt    6840
gaataagatt gtaaataata cgatagcaga attaaatcat gcaaaaatca ctgcgaaggg    6900
aaatgtcgga gttattacag agtctgatgc ggtaattgct aattatgcag aacagtgtc    6960 tggagtggcc cgtgcagcaa taggagcctc aaccagtgtg aatgaaatta caggatctac    7020
aaaagcatat gtaaaagatt ctacagtgat tgctaaagaa gaaacagatg attatattac    7080
tactcaaggg caagtagata aagtggtaga taaagtattc aaaaatctta atattaacga    7140
agacttatca caaaaaagaa aaataagtaa taaaaaagga tttgttacca atagttcagc    7200
tactcatact ttaaaatctt tattggcaaa tgccgctggt tcaggacaag ccggagtggc    7260
aggaactgtt aatatcaaca aggtttatgg agaaacagaa gctcttgtag aaaattctat    7320
attaaatgca aaacattatt ctgtaaaatc aggagattac acgaattcaa tcggagtagt    7380
aggttctgtt ggtgttggtg aaatgtagg agtaggagct tcttctgata ccaatattat    7440
aaaaagaaat accaagacaa gagttggaaa aactacaatg tctgatgaag gtttcggaga    7500
agaagctgaa attacagcag attctaagca aggaatttcc tcttttggag tcggagtcgc    7560
agcagccggg gtaggagccg gagtggcagg aaccgtttcc gtaaatcaat ttgcaggaaa    7620
gacggaagta gatgtggaag aagcaaagat tttggtaaaa aaagctgaga ttacagcaaa    7680
acgttatagt tctgttgcaa ttggaaatgc cgcagtcgga gtggctgcaa aaggagctgg    7740
aattggagca gcagtggcag ttaccaaaga tgaatcaaac acgagagcaa gagtgaaaaa    7800
ttctaaaatt atgactcgaa acaagttaga tgtaatagca gaaaatgaga taaaatcagg    7860
tactggaatc ggttcagccg gagctggaat tcttgcagcc ggagtatctg gagtggtttc    7920
tgtcaataat attgcaaata aggtagaaac agatatcgat catagtactt tacactcttc    7980
tactgatgta aatgtaaaag ctcttaataa aatttcgaat tccttgacag ccggtggagg    8040
agccgcaggt cttgcagcag ttaccggagt ggtttctgtt aacactataa atagttctgt    8100
gatagctcga gttcacaata actctgattt gacttccgta cgagaaaaag taaatgtaac    8160
ggcaaaagag gaaaaaaata ttaagcaaac agcagcaaat gcaggaatcg gaggagcagc    8220
aatcggagcc aatgtcttgg taaataattt tggaacagct gtagaagata gaaaaaattc    8280
tgaaggaaaa ggaacagaag ttttaaaaac tttagacgaa gttaacaaag aacaagataa    8340
aaaagtaaat gatgctacga aaaaaatctt acaatcagca ggtatttcta cagaagatac    8400
ttctgtaaaa gcggatagag gagatactca gggagaagga attaaagcca ttgtgaagac    8460
ttctgatatt attggaaaaa atgtagatat tacaacagag gacaagaata atatcacttc    8520
tactggtggt ttgggaactg caggtcttgc ttccgcatca ggaacagtgg cagttacaaa    8580
tattaaaaga aattccggag ttactgttga aaattctttt gtgaaagcag ctgaaaaagt    8640
aaatgttaga tcggatatta caggaaatgt tgctttaaca gcatatcaag gtcctgtagg    8700
agcattggga ataggagctg cctatgcaga attaaattct aatggaagat caaatatcag    8760
tattaaaaat tctaagctat taggaaaaaa tattgatgtt attgtaaaag ataaatcgga    8820
attgagagcg gaagcaaaag gattaaccgt aggagcggta gctgccggag ccattatctc    8880
aaaagcaaag aatgaaatga attcagaggt tgaaattgag aagagtattt tcaatgaaga    8940
aaatagagta actagcccctt ctaaaggaat tggaagagaa atcaatgtca agtggaaaa    9000 agaaaacaga gtgactgctg aatctcaagg agcttctgta ggagcagtag caggggcagg    9060
aattatttcc gaagcaaaag atgccggaag ctccttatttg aaagttagta caaaatccgg    9120
```

-continued

```
aagaagtatt tttcatgcag ataatgtgaa tatggaagca acacataaaa tgaaagtaac    9180
agcagtttct aaagcagtaa caggttctgt attgggagga gttggagtca ccaaggcaga    9240
agctactgct gcaggtaaaa ctatggtaga agttgaggaa ggaaatttgt tcagaacaaa    9300
tcgattgaat gcaatttcta aagtagaagg tttggatgaa gataaagtaa ctgctaaatc    9360
ttctgtagta tcaggaaatg gaggaggaat tgccggagca ggagtgaata cttctacagc    9420
acaaagtaat actgaatccg tagttcgttt acgaaagcaa gattatgaaa ataatgatta    9480
cacaaaaaaa tatatttcag aagtcaatgc tcttgcttta aatgatacaa agaatgaagc    9540
gaatatagaa tctttagcgg tagccggtgt gcatgcacaa ggaacaaaca aagcatttac    9600
gagatcaaac aagttaactt ctacaactgt aaatggagga aacgtatctc aacttcgtgc    9660
aaaagctttg gctaaaaatg aaaattatgg aaatgtaaaa ggaactggag gagccttagt    9720
cggagcggaa acagcagccg ttgaaaatta tacaaagagt actacaggag cattggttgc    9780
aggaaattgg gaattggag ataaattaga aacgattgca agagataata cgattgtaag     9840
agtcaacgga gacggaacca aaggaggtct tgtcggaaag aatggtattt ctgtgaaaaa    9900
tacaatttca ggggaaacaa aatcatccat tgaagataaa gccagaattg ttggaaccgg    9960
aagtgtaaat gtagatgctt tgaatgaact tgatgtagat ctacaaggaa aaagtggtgg   10020
ctatggtgga attggtattg gaaatgttga tgtaaataat gtgattaaga aaaatgtaga   10080
agccaaaatc ggaagacatg ctattgtaga aactactgga aaacaagaat atcaagcatt   10140
tacaagagca aaagtaaata ttcttggaaa aggagacgct gcagctgcag ctgcaatatc   10200
gaatgtacac atttccaatg agatggatat taaaaatttg gcaaagcagt atgcatcttc   10260
tcaattaata accaaaaatt caaaaaataa tattacttta gcatcaagta gtgaatcgaa   10320
tgtgaatgtt catggggtgg ctgaagcaag aggtgcagga gccaaagcga cagttagtgt   10380
aaagaatcaa ataaatagaa ctaataatgt tgatttagca ggaaaaatta aaacagaggg   10440
aaacatcaat gtatatgccg gatatgataa aaattataat ataagtaaga caaattctaa   10500
ggctattgcg gatgccaaaa gtcatgctgc agctgcttcg gcaactgcca ctattgaaaa   10560
aaatgaagta aaatttaata atgcgatccg agaatttaaa aataatctgg caagattgga   10620
agggaaagct aataaaaaaa cgtcggtagg atctaatcag gtagactggt atacggataa   10680
atatacatgg cattcttctg aaaaagcata caaaaaattg acatatcaat caaagagagg   10740
agaaaagg aaaaaatgaa tttaagagag agtaaattta gtgagtttt aaaaaattca     10800
aacataactt gttttgaaag agaagaagtg aaagatgagt tagaaacagt tgtatatcga   10860
agttttatgg aagtagaggg acaaaattta cctatggtaa ttgtgatgga taacagtatt   10920
tatacgaata tccgagtgca aattgctcca aaagtcataa aagatactaa taagaagcg    10980
gtactttcct atatcaatga attgaaccga gaatacaaag tatttaaata ttatgtgaca   11040
gaggatgcag atgtttgttt agatagttgt gtaacctcca ttgcagaaga atttaatcca   11100
gaaatggttt acactatttt aaatgtgatc                                    11130
```

RECOMBINANT *FUSOBACTERIUM NECROPHORUM* LEUKOTOXIN VACCINE AND PREPARATION THEREOF

CROSS-REFERENCE TO RELATED APPLICATIONS

This application is a divisional application of application Ser. No. 09/841,786 filed Apr. 24, 2001, now U.S. Pat. No. 6,669,940, which was a continuation-in-part application to application Ser. No. 09/558,257, filed Apr. 25, 2000, now abandoned. The content and teachings of each of these applications is hereby incorporated by reference herein.

SEQUENCE LISTING

A printed Sequence Listing accompanies this application, and also has been submitted with identical contents in the form of a computer-readable ASCII file on a floppy diskette with application Ser. No. 09/558,257, filed Apr. 25, 2000. Use of this previously filed CRF sequence listing is requested.

BACKGROUND OF THE INVENTION

1. Field of the Invention

The present invention is concerned with methods of cloning and expressing the leukotoxin gene from *Fusobacterium necrophorum* (*F. necrophorum*), sequencing and characterizing the leukotoxin protein expressed by this gene, truncating the gene into a series of nucleotide sequences, amplifying these sequences, expressing and recovering the polypeptides encoded by the nucleotide sequences, and utilizing the protein and the polypeptides in recombinant vaccines in order to confer effective immunity against infection caused by the production of leukotoxin by *F. necrophorum*. More particularly, it is concerned with production of an inactivated recombinant leukotoxin vaccine generated by amplifying five leukotoxin gene fragments and one upstream region through PCR, digesting the nucleotide sequences encoded by the gene fragments with restriction enzymes, expressing the polypeptide sequences coded by the nucleotide sequences through an expression vector, recovering these proteins as five truncated leukotoxin proteins (or polypeptides), purifying these proteins (or polypeptides) to apparent homogeneity, with or without inactivation of the truncated and full length proteins, and combining the inactivated recombinant leukotoxins with adjuvants.

2. Description of the Prior Art

Liver abscesses in feed lot cattle are a serious economic problem, causing condemnation of over 3 million livers and an estimated loss of $15 million annually in the United States. This estimate is based primarily on condemnation of liver and other organs, and does not include economic losses stemming from reduced feed intake, reduced feed efficiencies, decreased carcass dressing percentage and lowered weight gains. A number of studies have confirmed that cattle with abscessed livers gain less (average 4-5%) and have reduced feed efficiencies (average 7%) compared with cattle having healthy livers. The average incidence of abscessed liver in grain-fed cattle approximates 25-30%. To a lesser extent, liver abscesses in sheep and goats are also an economic problem.

*F. necrophorum* is a gram-negative, rod-shaped, nonspore-forming, nonmotile, strictly anaerobic and pleomorphic organism. Morphologically, the organism varies from short rods to filamentous with pointed and rounded ends. Cell lengths range from coccoid bodies of 0.5-0.7 μm in diameter to filaments over 100 μm. Surface colonies are 1-2 mm in diameter, circular, transparent to opaque, and with some strains producing α or β hemolysis. The organism ferments glucose, fructose and maltose only weakly with final pH around 5.0-6.3. It ferments lactate to acetate, propionate, and butyrate. Butyrate is the major product from lactate fermentation. Indole is produced from peptone. *F. necrophorum* has been isolated from the normal flora in the oral cavity, gastrointestinal cavity, and genitourinary tract of humans and animals. The organism is also known to survive in the soil.

*F. necrophorum* is a normal inhabitant of the gastrointestinal tracts of animals and humans. Virulence factors and pathogenic mechanisms that contribute to the transition of this otherwise commensal organism to a pathogen are poorly understood. A leukotoxin, endotoxin, hemolysin, hemagglutinin, and several enzymes such as deoxyribonuclease and proteases have been suggested as possible virulence factors. However, several studies implicate leukotoxin, a protein cytotoxic to ruminantpolymorphonuclear cells, as the major virulence factor. The importance of leukotoxin as a virulence factor in *F. necrophorum* infections is indicated by a correlation between toxin production and ability to induce abscesses in laboratory animals, an inability of nonleukotoxin-producing strains to induce foot abscesses in cattle following intradermal inoculation, and a relationship between antileukotoxin antibody titers and protection against infection in experimental challenge studies.

*F. necrophorum* is an opportunistic pathogen that is the primary etiologic agent of liver abscesses in ruminant animals. (Scanlan, et al., (1983)*Bovine rumenitis-liver abscess complex: a bacteriological review. Cornell Vet.* 73:288-297; Nagaraja, T. G. et al., (1998) *Liver abscesses in feedlot cattle: A review. J. Anim. Sci.*, 76:287-298; and Tan, et al., (1996) *Fusobacterium necrophorum infections: virulence factors, pathogenic mechanism and control measures. Vet. Res. Comm.*, 20:113-140). The organism has been recognized as an animal and human pathogen since the late 1800s, and is associated as a primary or secondary etiologic agent with numerous necrotic disease conditions in domestic and wild animals. In addition to liver abscesses, the organism is also the primary etiologic agent of foot rot, foot abscesses, calf diphtheria, and is frequently isolated from cases of mastitis, metritis, and necrotic lesions of the oral cavity.

Liver abscesses in cattle are part of a disease complex where the abscessation is secondary to primary foci of infection in the rumen epithelium. The pathogenesis can be summarized as follows: (1) ruminal lesions are induced by acidosis that follows rapid change in diet from high-roughage to high grain, prolonged feeding of high grain diet, or occasionally by foreign body penetration of the rumen epithelium; (2) bacteria present in the rumen invade the epithelium and form focal abscesses in the rumen wall; and (3) bacteria enter the portal circulation, and are carried to the liver where they localize in the parenchyma with subsequent abscess formation.

The ability of *F. necrophorum* to establish in the liver is attributed to the production of a toxin which is a secreted protein of high molecular weight active against leukocytes from ruminants called leukotoxin (or leucocidin). The toxin is a soluble extracellular protein that is cytotoxic to neutrophils, macrophages, hepatocytes, and ruminal cells. The leukotoxin protects against phagocytosis and is believed to aid in the establishment of *F. necrophorum* in the liver by directly impairing the normal defense mechanism and indirectly by the damage caused by cytolytic products released from neutrophils and macrophages to the hepatic cells. Therefore, the leukotoxin elaborated from *F. necrophorum* plays a critical role in *F. necrophorum* infection of the liver and is believed to be the primary virulence factor in the pathogenesis of liver abscesses (Tan et al., 1996).

Four biotypes (A, B, AB and C) of *F. necrophorum* have been described. (Langworth, (1977) *Fusobacterium necrophorum: its characteristics and role as an animal pathogen. Bacteriol. Rev.* 41:373-390) Biotype A, most frequently isolated from liver abscesses, is more pathogenic than biotype B, which predominates in ruminal wall abscesses. Biotypes AB and C are rarely isolated in liver abcesses (Berg, et al., (1982) *Studies of Fusobacterium necrophorum from bovine hepatic abscesses: Biotypes, quantitation, virulence, and antibiotic susceptibility. Am. J. Vet. Res.* 43:1580-1586), and biotype A has pathogenicity intermediate that of biotypes A and B while biotype C is non-pathogenic. (Shinjo, et al., (1990) *Recognition of biovar C of Fusobacterium necrophorum (flugge) Moore and Holdeman as Fusobacterium pseudonecrophorum sp. nov., nom. rev. (ex prevot* 1940) *Int. J. Sys. Bacteriol.* 41:395-397) Biotypes A and B, the most frequent types encountered in liver abscesses, have been assigned subspecies status: subsp. *necrophorum* and subsp. *funduliforme*, respectively (Shinjo et al., 1990). The subsp. *necrophorum* is more virulent, produces more leukotoxin and hemagglutinin, and is more frequently isolated from cattle liver abscesses than the subsp. *funduliforme*. Virulence factors and pathogenic mechanisms contributing to the formation of liver abscesses by *F. necrophorum* are poorly understood (Tan et al., 1996). However, several studies implicate leukotoxin to be a major virulence factor (Emery, et al., (1986) *Generation of immunity against Fusobacterium necrophorum in mice inoculated with extracts containing leukotoxin. Vet. Microbiol.* 12:255-268; Tan et al., 1996). The importance of leukotoxin is evidenced by correlation between toxin production and ability to induce abscesses in laboratory animals (Coyle-Dennis, et al., (1979) *Correlation between leukocidin production and virulence of two isolates of Fusobacterium necrophorum. Am. J. Vet. Res.* 40:274-276; Emery and Vaughn, 1986), inability of nonleukotoxin-producing strains to induce foot abscesses in cattle following intradermal inoculation (Emery, et al., (1985) *Culture characteristics and virulence of strains of Fusobacterium necrophorum isolated from feet of cattle and sheep. Australian Vet. J.* 62:43-46) and relationship between antileukotoxin antibody titers and protection in experimental challenge studies (Saginala, et al., (1996a) *The serum neutralizing antibody response in cattle to Fusobacterium necrophorum leukotoxoid and possible protection against experimentally induced hepatic abscesses. Vet. Res. Comm.*, 20:493-504; Saginala, et al., (1996b) *The serum neutralizing antibody response and protection against experimentally induced liver abscesses in steers vaccinated with Fusobacterium necrophorum. Am. J. Vet Res.*, 57:483-488; and Shinjo, et al., (1991) *Proposal of two subspecies of Fusobacterium necrophorum (Flugge) Moore and Holdeman: Fusobacterium necrophorum subsp. necrophorum subsp. nov., nom. rev. (ex Flugge* 1886), *and Fusobacterium necrophorum subsp. funduliforme subsp. nov., nom. rev. (ex Hall* 1898). *Int. J. Sys. Bacteriol.* 41:395-397).

Several investigators have attempted to induce protective immunity against *F. necrophorum* by using a variety of antigenic components. The results of such attempts have varied from ineffectual to significant protection. Clark et al. reported that cattle injected with *F. necrophorum* culture supernatant containing leukotoxin had a low incidence of foot rot caused by *F. necrophorum*. (Clark, et al. (1986), *Studies into immunization of cattle against interdigital necrobacillosis. Aust. Vet. J.* 63:107-110) Cell-free culture supernatant of a high leukotoxin producing strain of *F. necrophorum* (Tan et al., (1992) *Factors affecting leukotoxin activity of F. necrophorum. Vet. Microbiol.* 33:15-28), mixed with an adjuvant, was shown to elicit a high antileukotoxin antibody titer when injected in steers and provided significant protection to experimentally induced liver abscesses (Saginala et al., 1996a, b; 1997). *F. necrophorum* bacterin was used as an agent for immunizing cattle and sheep against liver necrosis as shown in EPO Application No. 460480 of Dec. 11, 1991 (the teachings of which are incorporated herein by reference). Specifically, virulent *F. necrophorum* isolates are inactivated using β-propiolactone, followed by addition of adjuvants. In addition, Abe et al., *Infection and Immunity*, 13:1473-1478, 1976 grew *F. necrophorum* for 48 hours. Cells were obtained by centrifuging, washing three times with saline, and were inactivated with formalin (0.4% in saline). The inactivated cells were then injected into mice to induce immunity. Two weeks after the last booster injection, each mouse was challenged with viable cells of *F. necrophorum*. The mice immunized with killed cells and challenged with live cells had no detectable bacteria in the liver, lung or spleen for up to 28 days. It was concluded that immunization of mice with formalin-killed *F. necrophorum* conferred protection against infection. Garcia et al. (*Canadian J. Comp. Med*, 38:222-226, 1974), conducted field trials to evaluate the efficacy of alum-precipitated toxoids of *F. necrophorum*. The vaccine preparation consisted of washed cells (unlikely to contain leukotoxin) that were ruptured by sonication. The most promising result was achieved with the injection of 15.5 mg protein of cytoplasmic toxoid. In this group, the incidents of liver abscesses was reduced to 10% from an average 35% in the control group. Emery et al., *Vet. Microbiol.*, 12:255-268, 1986, prepared material by gel filtration of 18-hour culture supernate of *F. necrophorum*. This elicited significant immunity against challenge by with viable *F. necrophorum*. The injected preparation contained endotoxin and the majority of the leukotoxic activity. U.S. Pat. No. 5,455,034 (the teachings of which are incorporated herein by reference) by Nagaraja et al. disclosed that prevention of leukotoxin production (or inhibition of its activity) in immunized animals prevents the establishment of *F. necrophorum* infection. Thus, immunization of the animals against *F. necrophorum* leukotoxin, so that the animals' white blood cells or tissue macrophages may phagocytize the bacteria, presented a way to prevent diseases associated with *F. necrophorum* infection, e.g., liver abscesses in cattle and sheep, and foot rot in cattle. In order to produce such a leukotoxoid vaccine, the *F. necrophorum* bacteria was cultured in a way to enhance the elaboration of leukotoxin in the supernate. Thereupon, bacterial growth and leukotoxin elaboration was terminated, and a vaccine prepared by inactivating at least the leukotoxin-containing supernate. In more detail, the leukotoxin elaboration method of the '034 patent involved first forming a culture of *F. necrophorum* bacteria in growth media, and thereafter causing the bacteria to grow in the culture and to simultaneously elaborate leukotoxin in the supernate. At the end of the culturing step, i.e., at the end of the selected culture time within the range of from about 4-10 hours, the bacterial growth and leukotoxin elaboration were terminated, and the leukotoxoid vaccine was prepared. This involved first separating the leukotoxin-containing supernate from the bacteria, followed by inactivation through use of formalin, β-propiolactone, heat, radiation or any other known method of inactivation. Alternately, the entire culture could be inactivated to form the vaccine.

Presently, the control of liver abscesses is with the use of antimicrobial feed additives. Antimicrobial compounds reduce the incidence of liver abscesses but do not eliminate the problem (Nagaraja et al., 1998). Therefore, an effective vaccine would be highly desirable to the feedlot industry. The vaccine approach also would alleviate public health concerns associated with the use of subtherapeutic levels of antibiotics in the feed. Because studies have indicated that antileukotoxin immunity reduces the incidence of hepatic abscesses and interdigital necrobacillosis (Garcia et al., 1974; Clark et al., 1986; Saginala et al., 1996a, b; 1997), the development of a recombinant leukotoxin vaccine will be of great value in the control of hepatic and interdigital necrobacillosis in cattle.

SUMMARY OF THE INVENTION

In order to better define the molecular nature of the *F. necrophorum* leukotoxin, and as a first step toward determining its specific role in the virulence of this bacterium, the leukotoxin gene was isolated, its nucleotide sequence determined, and the recombinant leukotoxin was expressed in *E. coli*.

The leukotoxin open reading frame (lktA) is part of a multi-gene operon containing 9,726 bp, and encoding a protein containing 3,241 amino acids with an overall molecular weight of 335,956 daltons. *F. necrophorum* leukotoxin is highly unstable as evidenced by western blot analysis of native leukotoxin (culture supernatant, sephadex gel or affinity purified) (FIG. 1). In this Figure, lane 1 contains whole cell lysate of *E. coli* cells expressing full-length recombinant leukotoxin, lane 2 contains Immuno-affinity purified native leukotoxin, lane 3 contains Sephadex gel purified leukotoxin, and lane 4 contains culture supernatant from *F. necrophorum* concentrated 60 times. The blots were probed with polyclonal antiserum raised in rabbits against affinity purified native leukotoxin. Because of the apparent instability of the full-length recombinant leukotoxin protein, the protein encoded by the gene was truncated into five recombinant polypeptides (or protein fragments, BSBSE, SX, GAS, SH and FINAL) having overlapping regions by truncating the full length gene into five different sections and amplifying, expressing in *E. coli*, and recovering the protein or polypeptide encoded by each of these sections. These polypeptides along with the full length protein are then tested to determine their immunogenicity and protective immunity in comparison to the efficacy of immunization conferred by inactivated native leukotoxin in *F. necrophorum* culture supernatant.

Specifically, the chromosomal DNA was extracted from *F. necrophorum* and partially digested by restriction endonucleases prior to being size-fractionated by sucrose gradient centrifugation. The 10-12 kb fragments were then ligated into a BamHI digested, dephosphorylated λZAP expression vector. Recombinant phages were infected into *Escherichia coli* and plated onto agar plates. Plaque lifts were performed (with polyclonal antiserum raised in rabbits against affinity purified leukotoxin) using an immunoscreening kit. Six immunoreactive recombinant phages were identified and denominated as clones 816, 611, 513, 911, 101, and 103. These clones were plaque-purified three times to ensure purity, phagemids rescued, and anti-leukotoxin immunoreactivity of the encoded proteins was confirmed. This immunoreactivity verified that the clones represented native leukotoxin *F. necrophorum*.

Expression of a polypeptide encoded by the 3.5 kb from the 5' end of the lktA caused immediate cessation of the growth and lysis of *E. coli* host cells suggesting that regions of leukotoxin could be toxic to *E. coli*. Of course, the objective was to create overlapping gene truncations extending over the entire lktA ORF so that the resulting polypeptide products are small and relatively stable on expression, but are large enough to be immunogenic. Also, the effectiveness of various recombinant truncated leukotoxin polypeptides alone or in combinations as immunogens and evaluated protective immunity against challenge with *F. necrophorum* in mice was investigated. The use of mice as an experimental model for *F. necrophorum* infection in cattle is well established (Abe et al., 1976; Conion et al., 1977; Smith et al., 1989; Garcia and McKay, 1978; Emery and Vaughan, 1986). Extension of the patterns of immunity and infection to cattle has shown that mice can be a valuable model to evaluate the immunogenicity and protection provided by various *F. necrophorum* fractions (Garcia et al., 1975; Garcia and McKay, 1978). Studies have also indicated that strains of *F. necrophorum* that are pathogenic in domestic animals, frequently are pathogenic in mice suggesting necrobacillosis as a disease is similar among these species of animals (Smith and Thornton, 1993).

The nucleotide sequence of the full length version of the gene is designated as SEQ ID No. 8 and the nucleotide sequences of the five truncations of the full length gene are designated as BSBSE (SEQ ID No. 9), SX (SEQ ID No. 10), GAS (SEQ ID No. 11), SH (SEQ ID No. 12), and FINAL (SEQ ID No. 13). Additionally, the nucleotide sequence of the upstream region of the full length gene is designated UPS (SEQ ID No. 14). The amino acid sequence of the full length protein encoded by the *F. necrophorum* gene is designated as SEQ ID No. 1 and the amino acid sequences of the truncated protein fragments respectively encoded by BSBSE, SX, GAS, SH and FINAL are designated as SEQ ID No. 2, SEQ ID No. 3, SEQ ID No. 4, SEQ ID No. 5, and SEQ ID No. 6. In the case of UPS, the polypeptide or truncated protein fragment encoded for by UPS is designated as SEQ ID No. 7. Finally, SEQ ID No. 15 is the full length gene sequence along with contiguous sequences.

Truncated recombinant polypeptides were purified by nickel affinity chromatography, and injected into rabbits to raise polyclonal antisera. Antibodies raised against two of the five polypeptides (BSBSE and GAS) neutralized the toxicity of *F. necrophorum* leukotoxin against bovine neutrophils. The effectiveness of the purified truncated polypeptides to induce a protective immunity was determined by injecting the polypeptides, individually or in mixtures, homogenized with Ribi adjuvant in mice, followed by experimental challenge with *F. necrophorum*. Two polypeptides (BSBSE and SH) induced significant protection in mice against *F. necrophorum* infection and the extent of protection was greater than the full-length native leukotoxin or inactivated culture supernatant. The study provided further credence to the importance of leukotoxin as the major virulence factor of *F. necrophorum* and the protein carries a domain (s) or epitope (s) that induces protective immunity against experimental infection.

The DNA and deduced amino acid sequences were compared with sequences in Genbank but no significant similarities (no sequences having greater than 22% sequence identity) were found. Thus, the *F. necrophorum* leukotoxin appears to be distinct from all known leukotoxins and RTX-type toxins. When the deduced amino acid sequence of the lktA region was subjected to the Kyte-Doolittle hydropathy analysis (FIG. 3), 14 sites of sufficient length and hydrophobic character to be potential membrane spanning regions, were found. Upstream to the leukotoxin ORF is an open reading frame of at least 1.4 kb in length, which is in the same orientation. It encodes a protein that has significant sequence similarity (21% or 62 out of 283 residues) to the heme-hemopexin utilization protein (UxuB) of *Haemophilus influenzae*.

Bacterial leukotoxins and cytotoxins generally have molecular masses of less than 200 kDa. This includes characterized leukotoxins of *Pasteurella hemolytica* (104,000 kDa; 10), *Staphylococcus aureus* (38,000+32,000 kDa; 20), or *Actinomyces actinomycetecomitans* (114,000 kDa; 15) or other pore-forming toxins of gram-negative bacteria (103,000 to 198,000 kDa; 30). However, leukotoxin secreted by *F. necrophorum* was shown to be approximately 300 kDa in size based on sephadex column purification and SDS-PAGE analyses.

As used herein, the following definitions will apply: "Sequence Identity" as it is known in the art refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. et al., eds., M. Stockton Press, New York (1991); and Carillo, H., et al. Applied Math., 48:1073 (1988), the teachings of which are incorporated herein by reference. Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al., Nucleic Acids Research, 12(1):387 (1984)), BLASTP, BLASTN and FASTA (Altschul, S. F. et al., J. Molec. Biol., 215:403-410 (1990). The BLASTX program is publicly available from NCBI and other sources (BLAST Manual, Altschul, S. et al., NCVI NLM NIH Bethesda, Md. 20894, Altschul, S. F. et al., J. Molec. Biol., 215:403-410 (1990), the teachings of which are incorporated herein by reference). These programs optimally align sequences using default gap weights in order to produce the highest level of sequence identity between the given and reference sequences. As an illustration, by a polynucleotide having a nucleotide sequence having at least, for example, 95% "sequence identity" to a reference nucleotide sequence, it is intended that the nucleotide sequence of the given polynucleotide is identical to the reference sequence except that the given polynucleotide sequence may include up to 5 point mutations per each 100 nucleotides of the reference nucleotide sequence. In other words, in a polynucleotide having a nucleotide sequence having at least 95% identity relative to the reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having a given amino acid sequence having at least, for example, 95% sequence identity to a reference amino acid sequence, it is intended that the given amino acid sequence of the polypeptide is identical to the reference sequence except that the given polypeptide sequence may include up to 5 amino acid alterations per each 100 amino acids of the reference amino acid sequence. In other words, to obtain a given polypeptide sequence having at least 95% sequence identity with a reference amino acid sequence, up to 5% of the amino acid residues in the reference sequence may be deleted or substituted with another amino acid, or a number of amino acids up to 5% of the total number of amino acid residues in the reference sequence may be inserted into the reference sequence. These alterations of the reference sequence may occur at the amino or the carboxy terminal positions of the reference amino acid sequence or anywhere between those terminal positions, interspersed either individually among residues in the reference sequence or in the one or more contiguous groups within the reference sequence. Preferably, residue positions which are not identical differ by conservative amino acid substitutions. However, conservative substitutions are not included as a match when determining sequence identity.

Similarly, "sequence homology", as used herein, also refers to a method of determining the relatedness of two sequences. To determine sequence homology, two or more sequences are optimally aligned as described above, and gaps are introduced if necessary. However, in contrast to "sequence identity", conservative amino acid substitutions are counted as a match when determining sequence homology. In other words, to obtain a polypeptide or polynucleotide having 95% sequence homology with a reference sequence, 95% of the amino acid residues or nucleotides in the reference sequence must match or comprise a conservative substitution with another amino acid or nucleotide, or a number of amino acids or nucleotides up to 5% of the total amino acid residues or nucleotides, not including conservative substitutions, in the reference sequence may be inserted into the reference sequence.

A "conservative substitution" refers to the substitution of an amino acid residue or nucleotide with another amino acid residue or nucleotide having similar characteristics or properties including size, charge, hydrophobicity, etc., such that the overall functionality does not change significantly.

Isolated" means altered "by the hand of man" from its natural state., i.e., if it occurs in nature, it has been changed or removed from its original environment, or both. For example, a polynucleotide or polypeptide naturally present in a living organism is not "isolated," but the same polynucleotide or polypeptide separated from the coexisting materials of its natural state is "isolated", as the term is employed herein. Finally, all references and teachings cited herein which have not been expressly incorporated by reference are hereby incorporated by reference.

Preferably, sequences having at least about 50% sequence homology or at least about 60% sequence identity with any of SEQ ID Nos. 1-15 are used for purposes of the present invention. More preferably, sequences having at least about 60% sequence homology or at least about 70% sequence identity are used for purposes of the present invention. Still more preferably, sequences having at least about 75% sequence homology or at least about 85% sequence identity are used for purposes of the present invention. Even more preferably, sequences having at least about 87% sequence homology or at least about 92% sequence identity are used for purposes of the present invention. Most preferably, sequences having at least about 95% sequence homology or at least about 98% sequence identity are used for purposes of the present invention.

DETAILED DESCRIPTION OF THE PREFERRED EMBODIMENT

The following examples set forth preferred embodiments of the present invention. It is to be understood, however, that these examples are provided by way of illustration and nothing therein should be taken as a limitation upon the overall scope of the invention.

EXAMPLE 1

Cloning of the Leukotoxin Encoding *F. necrophorum* Gene

Figure 2:
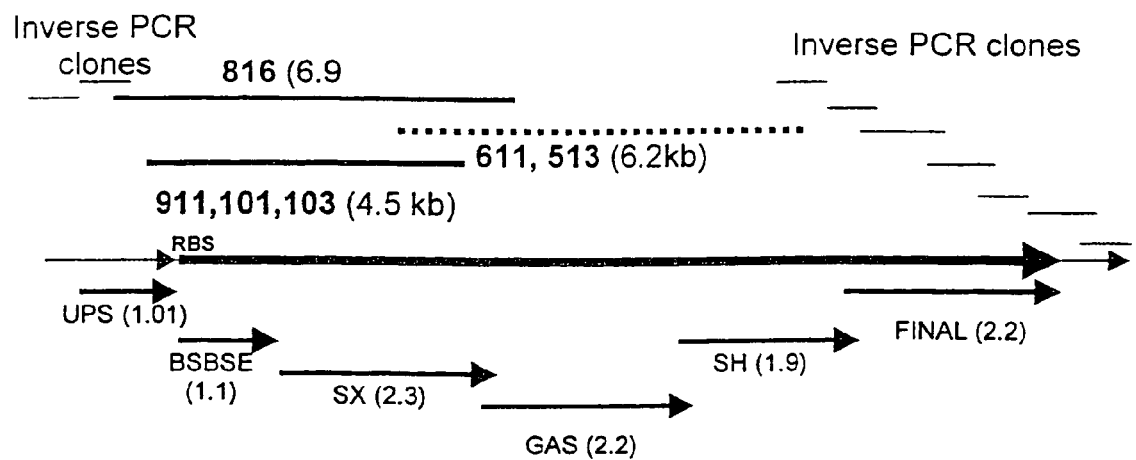
FIG. 2 is an illustration of the full length *F. necrophorum* gene and a map of the truncated regions of the genes and the expression clones encoded by the truncated regions.

Chromosomal DNA, extracted from *Fusobacterium necrophorum* subsp. *necrophorum*, strain A25 (Hull et al., 1981, Construction and expression of recombinant plasmids encoding type 1 or D-mannose-resistant pili from a urinary tract infection *Escherichia coli* isolate. *Infect. Immun.* 33:933-938.), was partially digested with the restriction endonuclease Sau3AI, and size-fractionated by sucrose gradient centrifugation (Baxter-Gabbard, 1972, A simple method for the large scale preparation of sucrose gradients. *FEBS. Lett.* 20117-119). The 10-12 kb DNA fragments were ligated in BamHI-digested, dephosphorylated λZAP Express vector, packaged into lambda phage head and tail protein components (Stratagene, La Jolla, Calif.), and recombinant phages were infected into *Escherichia coli* XL1-Blue MRF' and plated onto agar plates. Plaque lifts were performed (with polyclonal antiserum raised in rabbits against affinity purified leukotoxin) using the Pico-blue immunoscreening kit (Stratagene, La Jolla, Calif.). Six immunoreactive recombinant phages were identified (816, 611, 513, 911, 101, and 103; FIG. 2). These clones were plaque-purified three times to ensure purity, and anti-leukotoxin immunoreactivity of the proteins was confirmed.

Characterization of the Leukotoxin Gene

Excision of the Cloned DNA Insert into a Phagemid Vector

The λZAP Express vector is composed of a plasmid, designated pBK-CMV, which flanks the cloned insert DNA and which can be readily excised in order to obtain a phagemid that contains the cloned insert DNA. Therefore, a recombinant phagemid containing cloned *F. necrophorum* DNA insert was obtained by simultaneously infecting *E. coli* XLOLR with ExAssist helper phage and the recombinant phage (containing the cloned *F. necrophorum* DNA) according to the manufacturers instructions (Stratagene, La Jolla, Calif.). Once the recombinant plasmid was recovered, the presence of the DNA insert was confirmed by restriction endonuclease digestion and agarose gel electrophoresis.

Physical Mapping of the *F. necrophorum* DNA Inserts

Restriction enzyme digestion and mapping of the recombinant phagemid was performed (Sambrook et al., 1989, *Molecular cloning: a laboratory manual*. Cold spring harbor laboratory, Cold Spring Harbor, N.Y.). Combinations of the restriction enzymes SacI, SalI, SpeI, BamHI, EcoRI, HindIII, PstI, DraI, XbaI, HaeIII, BglII, SmaI, and KpnI were used for restriction enzyme mapping since single sites for these enzymes exist in the multiple cloning site of pBK-CMV. Insert DNA from all the six immunoreactive clones contained EcoRI, PstI, HindIII, DraI, HaeIII and BglII sites but not sites for Sac I, SmaI, SalI, XbaI, KpnI or BamHI.

Hybridization of the Cloned DNA Fragments with *F. necrophorum* Chromosomal DNA

Figure 4:
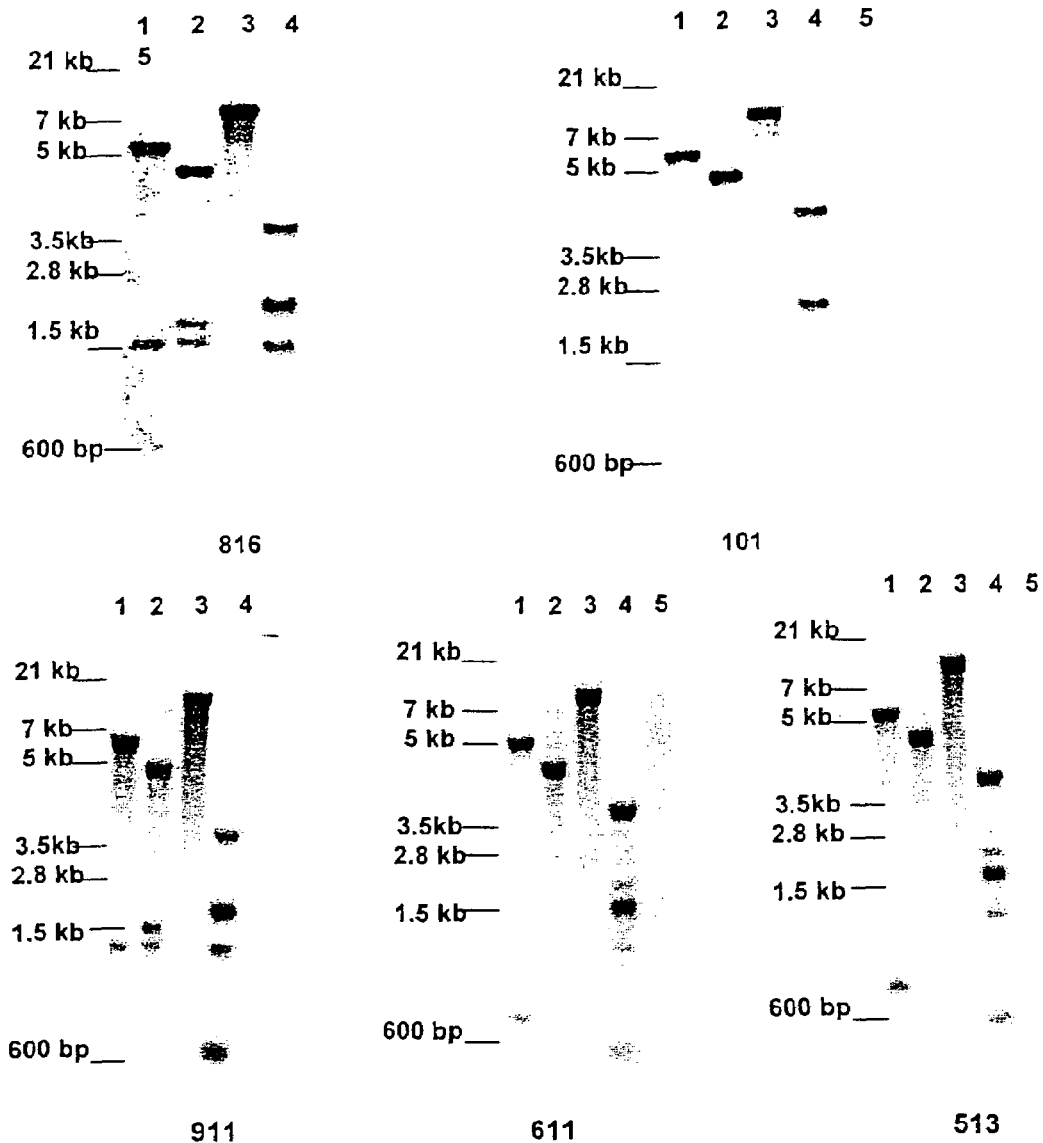
FIG. 4 is an illustration of the Southern Hybridization pattern of the chromosomal DNA of *F. necrophorum* with inserts from clones 513, 611, 816, 911, and 101.

Southern hybridization (Southern, 1975, *Detection of specific sequences among DNA fragments separated by gel electrophoresis. J. Mol. Biol.* 98:503) experiments were performed to confirm that the cloned DNA encoding the putative leukotoxin gene originated from *F. necrophorum* strain A25. Inserts from clones 513, 611, 816 and 911 were separated from the vector sequence by agarose gel electrophoresis of DNA digested with restriction enzymes SalI and XbaI. The insert DNA was used as a probe to hybridize to chromosomal DNA of *F. necrophonum* digested with EcoRI, EcoRV, HaeIII, and HindIII. A negative control, *E. coli* DH5α DNA, was digested with EcoRV. The Southern hybridization patterns included common DNA fragments indicating that the six clones carried overlapping inserts (FIG. 4). FIG. 2 illustrates the overlapping of each of the six immunoreactive clones designated 816, 611, 513, 911, 101, and 103. The expression clones for truncated peptides are designated UPS, BSBSE, SX, GAS, SH, and FINAL while the numbers in parentheses indicate the size in kilo-bases of each insert. The overlaps illustrated in FIG. 2 were further confirmed by sequence analysis.

DNA Sequence Analysis of the *F. necrophorum* DNA Inserts

Subclones of the cloned insert DNAs were constructed based on the restriction enzyme map of the cloned insert. Plasmid DNA was isolated from the resulting subclones (Birnboim and Doly, 1979, *A rapid alkaline extraction procedure for screening recombinant plasmid DNA. Nucleic acids Res*. 7:1513) and subjected to DNA sequence analysis using the Sanger dideoxy chain termination method (Sanger et al., 1977, *DNA sequencing with chain terminating inhibitors. Proc. Natl. Acad. Sci*. 74:5463-5467) using vector based primers. Additional sequence data were obtained by creating deletion clones utilizing restriction endonuclease sites discovered in the preliminary sequencing or by sequencing using primers derived from the sequenced DNA.

A total of 9.3 kb of the leukotoxin chromosomal region was cloned and sequenced. A single large open reading frame (designated lktA) is common to each of the immunoreactive clones. The ORF is preceded by a ribosome binding site (RBS) sequence (AAGGGGGT). Eight base pairs following the RBS sequence is a start codon (the ninth base pair) for the open-reading frame, which is approximately 8 kb in length. The stop codon of lktA was not found in this region. Therefore, the downstream sequences were extended by inverse PCR amplification, followed by cloning and sequencing of the amplified region.

Extension of the lktA Open Reading Frame Using Inverse PCR

Chromosomal DNA from *F. necrophorum* strain A25 was digested with restriction endonucleases TaqI, EcoRI, DdeI, or Sau3AI individually. After complete digestion of the chromosomal DNA with any one of these enzymes, the products were extracted with phenol and chloroform, and ethanol precipitated. Under dilute conditions (100 µl final volume) 200 ng of digested DNA was self-ligated using T4 DNA ligase at 16° C. overnight (Ochman et al., 1990, Amplification of flanking sequences by inverse PCR. In: M. A. Innis, D. H. Gelfand, J. J. Sninsky, and T. J. White (eds); PCR protocols; A guide to methods and applications. Acad. Press, Inc. Harcourt Brace Jovanovich, publishers, Sandiego, 219-227). Ligated DNA was phenol and chloroform extracted, ethanol precipitated and reconstituted in 10 µl of nuclease free water. Two microliters of the ligated DNA were used as template for PCR reaction with forward and reverse primers designed based on the sequence already known to us from previous sequencing reactions. Amplified products were cloned in the pCR 2.1 plasmid vector (Invitrogen) and sequenced using vector specific sequences. Sequencing six consecutive inverse PCR products enabled us to identify the stop codon for leukotoxin gene and the presence of another ORF downstream of lktA.

The entire leukotoxin gene was amplified using heat-stable DNA polymerase (ExTaq) as two fragments using *F. necrophorum* strain A25 chromosomal DNA as the template. The 5'4.3 kb of the lktA open-reading frame encoding the N-terminal half of the leukotoxin, and the 3'5.4 kb representing the C-terminal half of the leukotoxin protein. Making use of the unique Nhe I site present at this location (4.3 kb from the start codon), the leukotoxin gene was joined together to give the giant 9.726 kb ORF. The entire leukotoxin gene was cloned into the modified variant (with coding sequence for six histidine residues in the N-terminus of the expressed protein) of the expression vector pET 14b (Novagen Corp. Madison, Wis.). This T7 polymerase based system should enhance expression of toxic proteins, without damage to the host cell *E. coli*.

EXAMPLE 2

Preparation of Polyclonal Antileukotoxin Antiserum

Leukotoxin from *F. necrophorum* subsp. *necrophorum* strain A25 was purified using an immunoaffinity column containing antileukotoxin monoclonal antibody, F7B10 (Tan, Z. L., T. G. Nagaraja, M. M. Chengappa, J. J. Staats. 1994. Purification and quantification of *Fusobacterium necrophorum* leukotoxin using monoclonal antibodies. Vet. Microbiol. 42:121-133.). Affinity-purified native leukotoxin (0.5 mg) in 100 μl of PBS was homogenized with an equal volume of Freund's complete adjuvant and injected intramuscularly in rabbits. A booster dose was given on day 21 with 0.5 mg of native toxin in 100 μl of PBS homogenized with an equal volume of Freund's incomplete adjuvant. Serum samples were collected on day 42. Naturally occurring rabbit antibodies that react to *E. coli* proteins were removed from the antisera as follows. Cell pellets of *E. coli* XL1-Blue MRF' host cells grown overnight in Luria broth were sonicated in PBS and centrifuged to remove cellular debris, and the supernatant was incubated with 100 mm diameter nitrocellulose membranes at 37° C. for 3 hours. The nitrocellulose membranes were then washed twice in PBS-T (0.05% Tween 20 in PBS [pH 7.2]), blocked in 2% BSA, and washed three times again in PBS-T. Two ml of rabbit antileukotoxin polyclonal antiserum were diluted 10-fold in PBS-T containing 0.2% BSA and exposed to 10 changes of *E. coli* lysate-treated nitrocellulose membranes for 30 minutes duration each at 37° C. The resultant polyclonal antisera had minimal reactivity against *E. coli* proteins. Neutralizing activity of the serum, as determined by the MTT dye neutralization test and the indirect ELISA titer, were measured as described previously (Tan, Z. L., T. G. Nagaraja, M. M. Chengappa. 1992. Factors affecting leukotoxin activity of *Fusobacterium necrophorum*. Vet. Microbiol. 33:15-28; Tan, Z. L., T. G. Nagaraja, M. M. Chengappa, and J. S. Smith. 1994. Biological and biochemical characterization of *Fusobacterium necrophorum* leukotoxin. Am. J. Vet. Res. 55:515-519; Tan, Z. L., T. G. Nagaraja, M. M. Chengappa, J. J. Staats. 1994. Purification and quantification of *Fusobacterium necrophorum* leukotoxin using monoclonal antibodies. Vet. Microbiol. 42:121-133).

Extraction of Genomic Dna from *F. necrophorum* and *E. Coli*

Chromosomal DNA was extracted from highly virulent *F. necrophorum* subsp. *necrophorum*, strain A25 (18) and *E. coli* DH5α ($F^{-}\lambda^{-}\phi80\Delta$ [lacZYA-argF] endA1 recA1 hsdR17 deoR thi-1 supE44 gyrA96 relA1), using a modification of the method described by Hull and coworkers (Hull, R. A., R. E. Gill, P. Hsu, B. H. Minshew, and S. Falkow. 1981. Construction and expression of recombinant plasmids encoding type 1 or D-mannose-resistant pili from a urinary tract infection *Escherichia coli* isolate. Infect. Immun. 33:933-938). *E. coli* was cultured in Luria broth with shaking under aerobic conditions at 37° C. and *F. necrophorum* was grown overnight in a prereduced anaerobically sterilized brain heart infusion broth in serum bottles under anaerobic conditions at 39° C. Cell pellets were resuspended in TES buffer (25% sucrose, 50 mM Tris-HCl [pH 7.5] and 1 mM EDTA); spheroplasted with lysozyme at room temperature for 30 min; and lysed using sarkosyl in the presence of proteinase K at 60° C. for 1 hour. The product was extracted with buffer-saturated phenol and chloroform, and the DNA was precipitated in 2.5 volumes of ice-cold ethanol. The DNA pellet was resuspended in TE buffer (10 mM Tris-HCl [pH 8.0] and 1 mM EDTA) and subjected to ultracentrifugation in a cesium-chloride step-gradient (43.5% to 60%) containing ethidium bromide (0.4 mg/ml final volume). The chromosomal DNA band was extracted with TE buffer and CsCl saturated isopropanol to remove ethidium bromide and dialyzed against double-distilled water. The DNA concentration and purity were checked spectrophotometrically.

Genomic Library and Screening

Genomic DNA of *F. necrophorum* A25 was digested partially with restriction endonuclease Sau3AI, and the fragments were size-fractionated in a sucrose gradient. Ten to 12 kb fragments were cloned into BamHI digested and alkaline phosphatase-treated Lambda zap Express vector (Stratagene Corp. La Jolla, Calif.) as per the manufacturer's instructions. Recombinant lambda DNA was packaged (Gigapack gold; Stratagene) and used to infect XL1 Blue MRF' host cells (Stratagene). Plaques were lifted onto nitrocelluose membrane and screened with antileukotoxin polyclonal antiserum using a Picoblue immuno-screening kit as per the manufacturer's protocol (Stratagene). Immunoreactive clones were plaque purified three times using the polyclonal antiserum. The recombinant DNA from immunoreactive clones was rescued as phagemid (pBKCMV) clones using Exassist helper phage in *E. coli* XLOLR strain as per the manufacturer's protocol (Stratagene).

DNA Sequencing Analysis

Phagemids from immunoreactive clones, purified PCR products, and plasmid subclones were sequenced using vector-specific or internal primers with a model 373A automated DNA sequencer (Applied Biosystems, Foster City, Calif.). The DNA sequences were aligned and analyzed using Sequencher (version 3.1.1, Gene Codes Corp., Ann Arbor, Mich.) and DNA Strider (Version 1.2).

Inverse Pcr and Sequence Extension

Chromosomal DNA from *F. necrophorum* strain A25 was digested singly with restriction endonucleases TaqI, EcoRI, DdeI, or Sau3AI. After complete digestion of the chromosomal DNA with any one of these enzymes, the products were extracted with phenol and chloroform, and precipitated with ethanol. Under dilute conditions (200 ng of digested DNA in 100 µml total volume), DNA was self-ligated using T4 DNA ligase at 16° C. overnight. Ligated DNA was extracted with phenol and chloroform, precipitated with ethanol and reconstituted in 10 ml of nuclease free water. Two microliters of the ligated DNA were used as templates for 100 ml PCR reactions with forward and reverse primers designed based on the sequence obtained from previous sequencing reactions. The products from inverse PCR were cloned in pCR TOPO cloning vectors (TA, Blunt2 or Blunt4) as per the manufacturer's instructions (Invitrogen Corp. San Diego, Calif.), and sequenced directly or after subcloning, using vector specific primers. Six successive inverse PCRs were carried out to reach the 3' end of the leukotoxin gene.

Creation of Gene Truncations

Polymerase chain reaction using thermnostable polymerase (EXTaq; Takara Corporation, Madison, Wis.) was used to amplify five overlapping regions of the leukotoxin gene ranging in size from 1.1 kb to 2.8 kb. Chromosomal DNA from *F. necrophorum* strain A25 was used as the template. The forward primers were designed to contain a SacI site, and the reverse primers had an XmaI site, for in-frame insertion into the His-tag expression vector pQE30 (Qiagen Inc. Valencia, Calif.). Each truncated gene product overlapped with the adjacent product by at least 100 bp. One kb of DNA from the 3' end of the upstream open reading frame (ups) was amplified and cloned in pQE30 vector as described above. Recombinant plasmids were transformed into *E. coli* host strain M15 for inducible expression of proteins encoded by cloned genes under the control of the lac promoter. The five truncated leukotoxin polypeptides and the C-terminus of the upstream polypeptide were purified using nickel chelation chromatography under denaturing conditions to apparent homogeneity as indicated by silver-stained SDS-PAGE gels (data not shown).

Preparation of Polyclonal Antiserum against the Truncated Leukotoxin Polypeptides New-Zealand White rabbits were injected intramuscularly with the five truncated leukotoxin polypeptides or the upstream polypeptide (0.5 mg/animal) precipitated with aluminum hydroxide. A booster dose was given on day 21 (0.5 mg /animal). Serum samples were collected on days 21 and 42 and antileukotoxin titers were determined by indirect ELISA using affinity purified native leukotoxin (Tan, Z. L., T. G. Nagaraja, M. M. Chengappa, J. J. Staats. 1994. Purification and quantification of *Fusobacterium necrophorum* leukotoxin using monoclonal antibodies. Vet. Microbiol. 42:121-133.). Leukotoxin neutralizing activities of the 42 day serum samples were determined by the MTT dye neutralization assay using 200 units of toxin (id.).

Immunoblot Analysis

Affinity-purified native leukotoxin, the truncated leukotoxin polypeptides and upstream polypeptide purified over nickel columns, whole cell lysates from bacterial clones carrying recombinant expression plasmids, and concentrated culture supernatants were resolved by SDS-PAGE (6 or 10% acrylamide) and electroblotted to nitrocellulose membranes (BioRad minigel II electrophoresis and transfer unit). Monoclonal antibody against native leukotoxin (F7B10) or polyclonal antisera raised against native leukotoxin, various truncated leukotoxin or upstream polypeptides were used to probe the western blotted proteins. Goat antimouse or anti-rabbit IgG conjugated to alkaline phosphatase (Sigma Chemical Company, St. Louis, Mo.) was used as the secondary antibody, and the immunoreactive proteins were detected using nitro blue tetrazolium and 5-bromo-4-chloro-3-indolyl-phosphate as substrates.

Cloning and Expression of Full-length Leukotoxin ORF

A 4.3 kb DNA fragment containing the 5' end of the lktA open reading frame up to the internal NheI restriction endonuclease recognition site was amplified from A25 chromosomal DNA. This fragment was cloned into the kanamycin resistance encoding vector pCR Blut II TOPO. A 5.4 kb DNA fragment extending from the NheI site to the 3' end of the lktA open reading frame was PCR amplified and cloned into the low-copy, spectinomycin resistance plasmid pCL1921 (Lerner, C. G., and M. Inouye. 1990. Low copy number plasmids for regulated low level expression of cloned genes in *Escherichia coli* with blue/white insert screening capability. Nucl. Acid. Res.18:4631-4633.). The two resulting plasmid clones were ligated together making use of the unique NheI site present in lktA ORF, and the transformants were selected on media containing spectinomycin (100 µg/ml) and kanamycin (21 µg/ml). The pCR Blunt II vector specific sequences were then removed by digesting the resultant plasmid with SacI followed by ligation under dilute conditions and selection on L-agar containing 100 µg/ml spectinomycin. Thus the entire 9,726 base pairs of the leukotoxin ORF were cloned in a low-copy number plasmid pCL 1921 to produce pSN 1999. Making use of the unique XmaI site introduced into at the 3' end of the open reading frame and the SacI site introduced into the 5' end of the reading frame, the entire lktA coding sequence was cloned in-frame into the expression plasmid pQE30 to give pSN2000.

Flow Cytometric Analysis of Leukotoxin Biological Activity

Bovine peripheral polymorphonuclear leukocytes were isolated as described previously (Tan, Z. L., T. G. Nagaraja, M. M. Chengappa. 1992. Factors affecting leukotoxin activity of *Fusobacterium necrophorum*. Vet. Microbiol. 33:15-28; Tan, Z. L., T. G. Nagaraja, M. M. Chengappa, and J. S. Smith. 1994. Biological and biochemical characterization of *Fusobacterium necrophorum* leukotoxin. Am. J. Vet. Res. 55:515-519). Untreated cells (negative control) or those treated with either 200 units of native leukotoxin from *F. necrophorum* (positive control) or whole-cell lysates from clones expressing full-length recombinant leukotoxin were tested for viability by flow cytometry (Facstar, Becton Dickinson Immunocytometry Systems, San Jose, Calif.). Briefly, 1 ml of bovine peripheral PMNs ($9 \times 10^6$ cells/ml) was incubated with various preparations of toxin for 45 min at 37° C. in a chamber containing 5% $CO_2$. The cells were then washed twice in 2 ml of HBSS (pH 7.2) and resuspended in 300 µl of HBSS. These cells were treated for 10 min in the dark at room temperature with 10 µl of 5 mg/ml propidium iodide (PI). The red fluorescence (FL-2 [585/42]) is proportional to the number of cells which have lost membrane integrity and, therefore, do not exclude the propidium iodide. Leukocyte subpopulations were displayed in a dot plot and gated according to size based on forward scatter (FSC) and granularity or 90 degree light scatter (SSC). A region was placed around granulocytes, cells of larger size and granularity and thus excluding monocytes, and data were collected on 10,000 gated cells. The identity of the gated cells as granulocytes by was indicated by indirect immunofluorescence labelling with monoclonal antibody DH59B (VMRD Inc., Pullman, Wash.) which reacts with the granulocyte-monocyte-1 receptor. Fluorescence signals displayed as a dot plot were used to determine the percent positive cells by quadrant statistics.

Southern Blot Analysis

Genomic DNA was extracted from several strains of *F. necrophorum* subsp. *necrophorum* and subsp. *funduliforme* isolated from ruminal contents or liver abscesses. Chromosomal DNA was digested to completion with HaeIII, which cleaves the leukotoxin ORF once. The digested DNA was electrophoresed in a 1% agarose gel and Southern blotted onto a nitrocellulose membrane. The full-length lktA ORF cloned in pQE30 (pSN2000) was released by digestion with SacI and XmaI, and the insert DNA was gel purified, radiolabelled with [$\alpha$-$^{35}$S]dATP, and hybridized.

Nucleotide Sequence Accession Number

The nucleotide sequence of *F. necrophorum* subsp. *necrophorum* strain A25 lktA has been assigned GenBank accession number AF312861.

Cloning and Nucleotide Sequence of the *F. necrophorum* Leukotoxin Determinant

Figure 1:
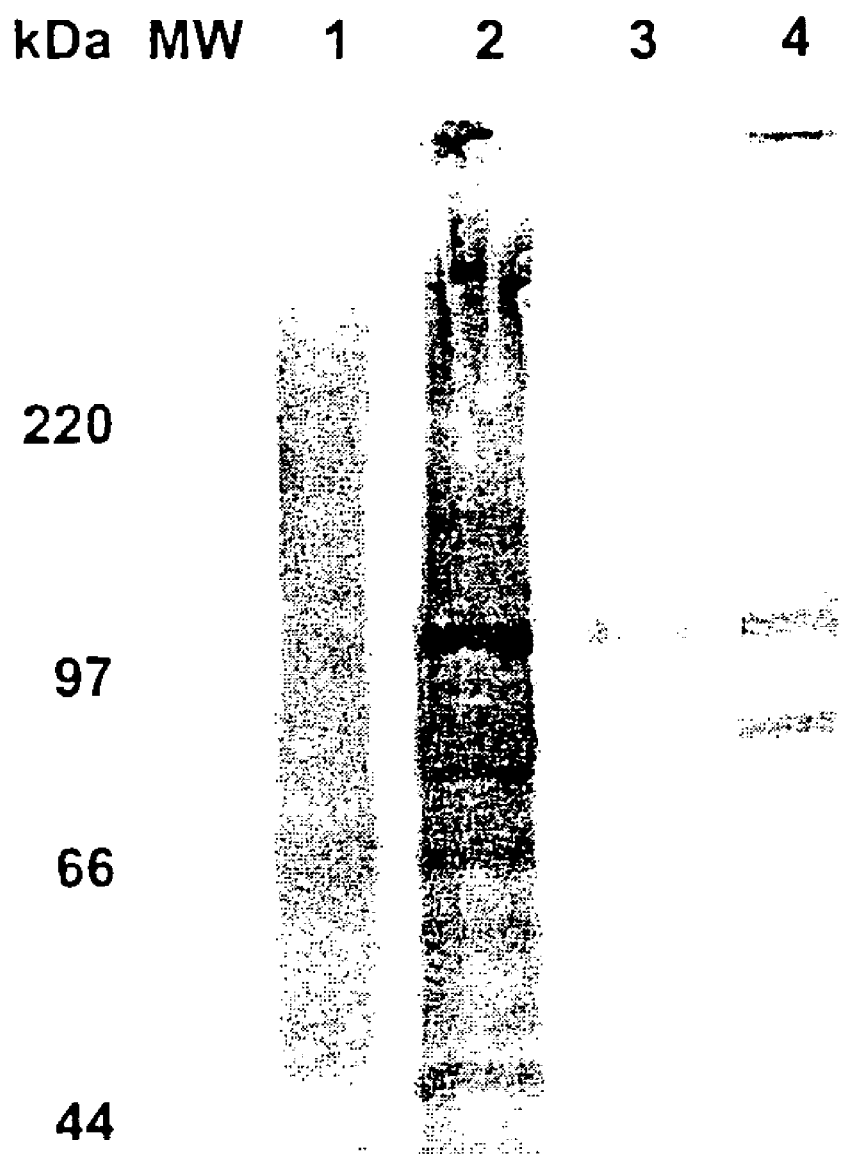
FIG. 1 is a Western blot assay of native and recombinant leukotoxins.
Figure 5:
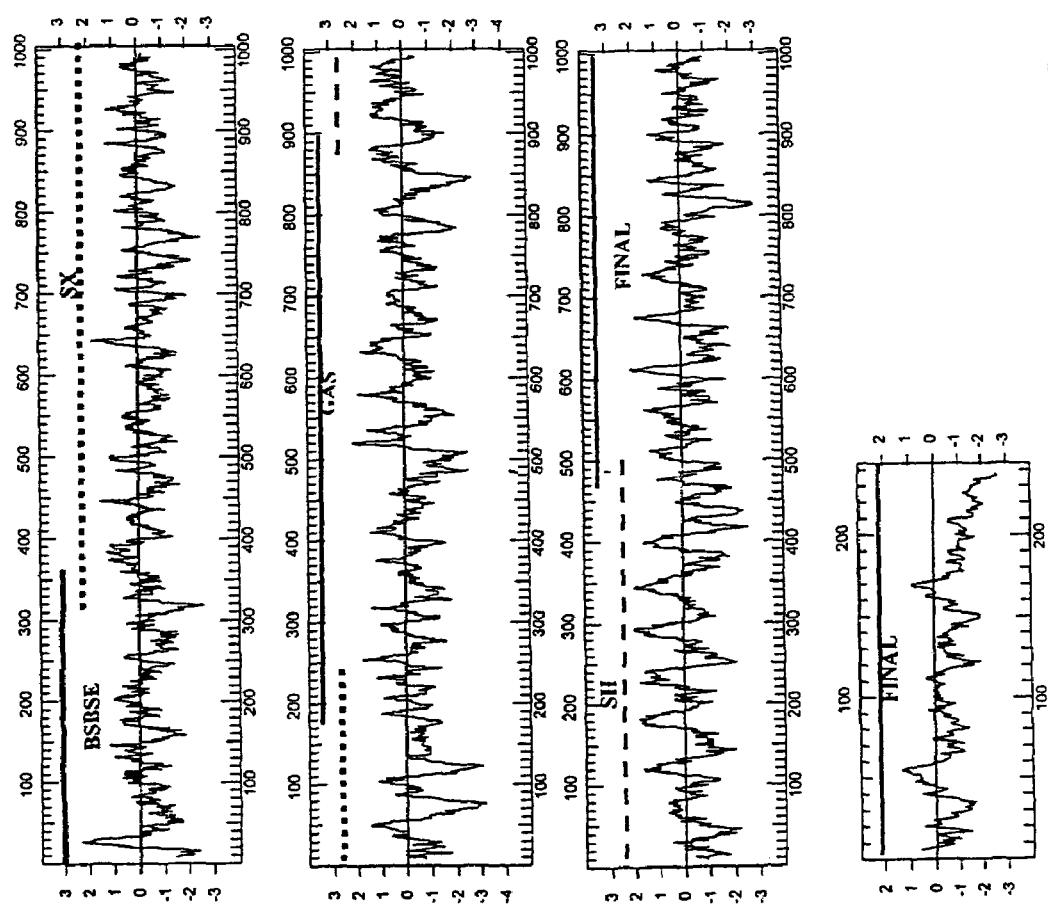
FIG. 5 is a Kyte-Doolittle hydropathy plots of deduced amino acid sequences from the *F. necrophorum* leukotoxin gene wherein the lines above the plot correspond to the regions of the five truncated LktA polypeptides (BSBSE, SX, GAS, SH, and FINAL)

A Sau3A-generated genomic library of *F. necrophorum* strain A25 DNA was screened using rabbit polyclonal antisera raised against immunoaffinity-purified native leukotoxin and immunoreactive clones were identified. The clones carried inserts of approximately 4.6, 5.5, and 6.3 kb in length. The immunoreactive clones containing the leukotoxin open reading frame (designated lktA) are depicted in FIG. 1. Inverse PCR was used to extend the cloned region to allow completion of the sequence of the lktA open reading frame. The 11,130 bp sequence of *F. necrophorum* DNA contained one complete and two partial ORFs. The upstream (orfB) partial ORF comprises the first 1,018 bp. The lktA ORF initiates 16 bp downstream of the lktB ochre codon. A putative ribosome-binding site (RBS) with the sequence AAGGGGGT precedes the lktA ORF. The first two bases of the RBS were the last two bases of the lktB stop codon. The leukotoxin determinant is 9,726 bp and encodes a protein of 3,241 amino acids with an overall molecular weight of 335,956. The deduced protein sequence is unusual in that it lacks cysteine residues. The protein has substantial hydrophobic character (FIG. 5) and possesses 14 regions with sufficient hydrophobic character and length to be membrane spanning. However, this is a secreted toxin in *F. necrophorum*. The potential transmembrane domains may provide a clue as to the mode of action of the leukotoxin on the target neutrophils.

A BLAST search of the protein database with the deduced leukotoxin did not indicate significant sequence similarity to any bacterial cytotoxins. Some sequence similarity, generally 17-20% amino acid identity over a window of 1,500 to 2,000 residues, was found to certain high molecular weight cell surface proteins. These include the SrpA serine-rich protein from *Streptococcus cristatus* (accession number U96166), the hemagglutinin from *Streptococcus gordonii* (AB029393), a surface protein from *Xylella fastidiosa* (AE003982), the outer membrane protein A from *Rickettsia australis* (AF149108), the 190 kDa surface antigen precursor from *R. rickettsii* (A41477), and the high molecular weight antigen (HmwA) of *Haemophilus influenzae* (AF 180944). Given the molecular size of the leukotoxin protein, which is larger than any known bacterial exotoxin, its lack of cysteine residues, and its lack of sequence similarity to other bacterial leukotoxins, the LktA protein from *F. necrophorum* appears to be a novel leukotoxin.

The deduced amino acid sequence of the carboxy terminus of the OrfB protein has some sequence identity to heme-hemopexin utilization protein (HxuB) of *Haemophilus influenzae* (21% amino acid identity over a 283 residue window). The putative open reading frame upstream of the leukotoxin determinant does encode a protein product. The 1 kb sequence encoding the carboxyl terminus of this ORF was cloned into pQE30, and the polypeptide was expressed with the six histidine tag at its N-terminus. The protein was purified by nickel chelation chromatography, and the antiserum was raised against this protein in rabbits. Western blot analysis revealed that this antiserum recognized a 60 kDa protein in whole-cell lysates of *F. necrophorum* (data not shown). This protein was not present in culture supernatants or in purified outer membranes of *F. necrophorum*.

Downstream of lktA is another apparent open reading frame, which extends to the end of the cloned sequences (375 bp). The putative ATG start codon overlaps the opal stop codon of lktA. The nucleotide and deduced amino acid sequences do not show significant sequence similarity to any sequences currently in GenBank.

Figure 6:
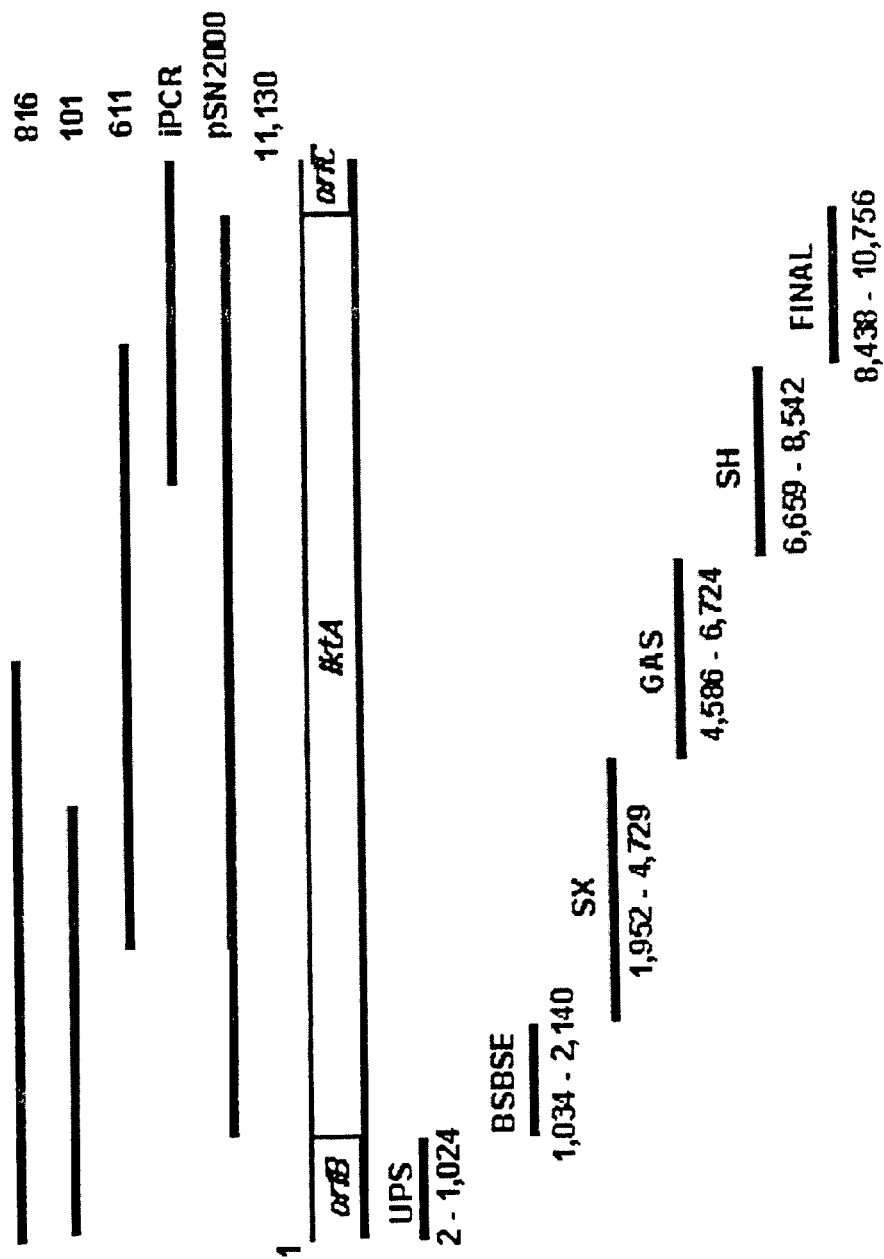
FIG. 6 is an illustration of the leukotoxin locus of *F. necrophorum*.

Creation of Truncated Leukotoxin Polypeptides and Characteristics of Polyclonal Antisera Raised against them A 3.5 kb sequence from the 5' end of lktA gene was amplified by PCR and cloned in-frame in the expression vector pQE30. Induced expression of this truncated version of the leukotoxin protein with IPTG resulted in the immediate cessation of growth and lysis of the host *E. coli* cells. In order to obtain better expression of recombinant protein and less toxicity to *E. coli* host cells, smaller truncations of the leukotoxin gene were constructed. The truncated polypeptides were named BSBSE, SX, GAS, SH, and FINAL starting from the N-terminus and ending at the C-terminus of the leukotoxin protein (FIG. 6). In this Figure, the boxes represent the leukotoxin open reading frame (lktA) and its flanking putative open reading frames. The lines above the boxes represent the phagemid clones (816, 101, and 611) obtained from the immunoreactive plaques in the cloning experiments. The region designated iPCR represents the sequence obtained from sequencing a series of inverse PCR clones. The plasmid pSN2000 contains the entire lktA open reading frame. Below the boxes are the clones expressing the truncated leukotoxin polypeptides. The numbers refer to the nucleotide positions of the boundaries of each truncation relative to the 11,130 bp sequence deposited in GenBank.

Figure 7A:
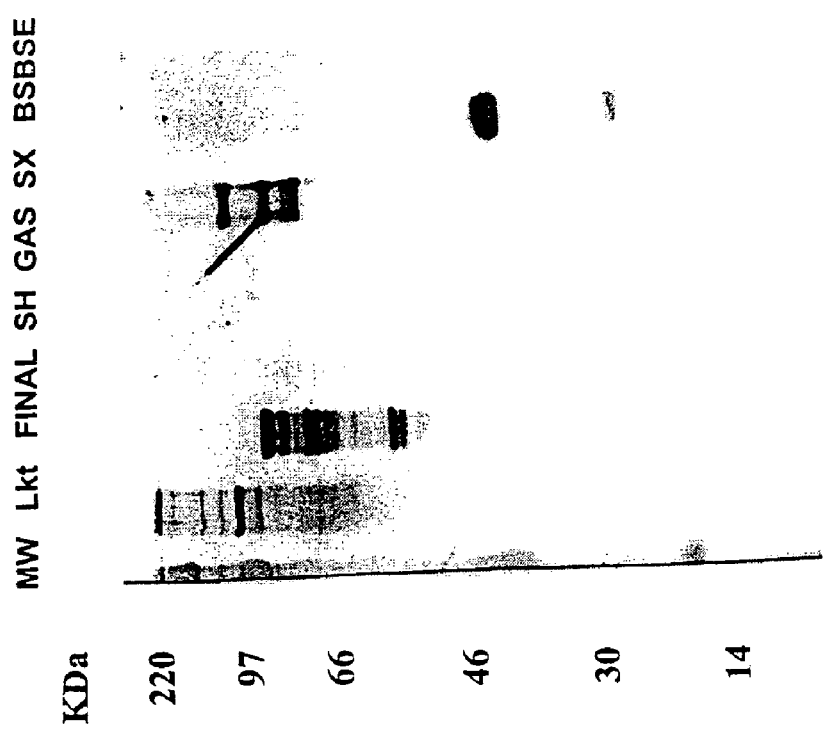
FIG. 7a is a Western blot analysis of truncated forms of purified recombinant leukotoxin protein probed with polyclonal antileukotoxin antiserum.
Figure 7B:
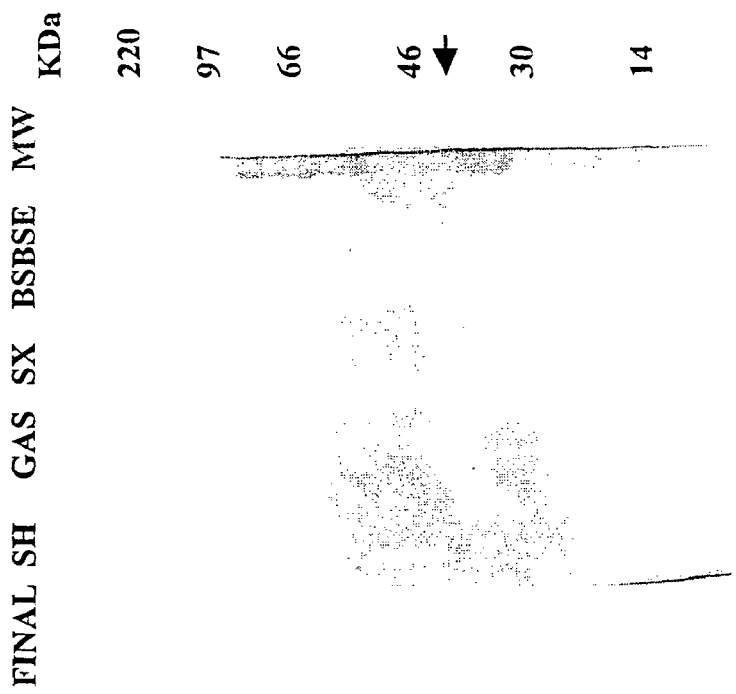
FIG. 7b is a Western blot analysis of truncated forms of purified recombinant leukotoxin protein probed with monoclonal antibody F7B10.

Each polypeptide had an overlap of at least 21 amino acids with its adjacent polypeptide. The C-terminal truncated polypeptide of the upstream protein and the polyclonal antiserum raised against it, served as a negative control in our toxicity and toxin-neutralization studies. Purified truncated leukotoxin and upstream polypeptides were then analyzed by western blots, for their reactivity against polyclonal and monoclonal antisera raised against affinity-purified native leukotoxin, using western blot analysis. Antileukotoxin polyclonal antisera reacted strongly with polypeptides BSBSE, SX, and FINAL and weakly with polypeptides GAS and SH (FIG. 7a). Monoclonal antileukotoxin antibody reacted with the N-terminal polypeptide, BSBSE, but not any other truncated leukotoxin polypeptides (FIG. 7b). As expected, the UPS polypeptide did not react with polyclonal or monoclonal antileukotoxin antibodies. Polyclonal antisera raised in rabbits against each of the truncated leukotoxin polypeptides reacted strongly with the corresponding polypeptide and also the native leukotoxin. These results are shown below in Table 1. Antibodies raised against individual truncations reacted weakly to their adjacent polypeptides because of the presence of the overlapping amino acid sequences between them (data not shown). Antiserum raised against UPS (from the upstream ORF) failed to recognize the leukotoxin.

TABLE 1

Neutralization of Leukotoxin from *F. Necrophorum* by Rabbit Polyclonal Antisera Raised Against the Recombinant Truncated Polypeptides.

| Immunogen | ELISA Titer | | Neutralization |
| | Self polypeptide | Native Leukotoxin | Titer |
| --- | --- | --- | --- |
| UPS | 9,600 ± 1,693 | 19 ± 17 | <5 |
| BSBSE | 10,420 ± 1,142 | 10,680 ± 1,653 | 1,460 ± 71 |
| SX | 8,754 ± 983 | 7,480 ± 1,593 | <5 |
| GAS | 8,748 ± 865 | 8,100 ± 1,297 | 1,280 ± 89 |
| SH | 10,180 ± 1,789 | 8,220 ± 1,301 | <5 |
| FINAL | 9,750 ± 1,343 | 9,440 ± 1,262 | <5 |

ELISA titers are presented as the mean of three determinations expressed as the reciprocal of the highest dilution giving a positive reaction (± standard deviation). The neutralization titer is the reciprocal of the greatest dilution of antiserum able to neutralize the activity of 200 units of native leukotoxin in an MTT assay.

Antisera raised against the individual polypeptides were tested for neutralization activity against the native leukotoxin from *F. necrophorum*. An ELISA assay was utilized to measure the reactivity of each antiserum against the leukotoxin. An MTT dye reduction assay was then utilized to determine if the antiserum could neutralize the toxic effects of the leukotoxin against bovine peripheral leukocytes. As shown in Table 1, two of the antisera could neutralize the leukotoxin. The active antisera were raised against the N terminal polypeptide (BSBSE) and the middle polypeptide (GAS). The other three antisera did not have neutralizing activity in this assay, although the ELISA data indicated that each antiserum recognized the *F. necrophorum* leukotoxin.

Figure 7C:
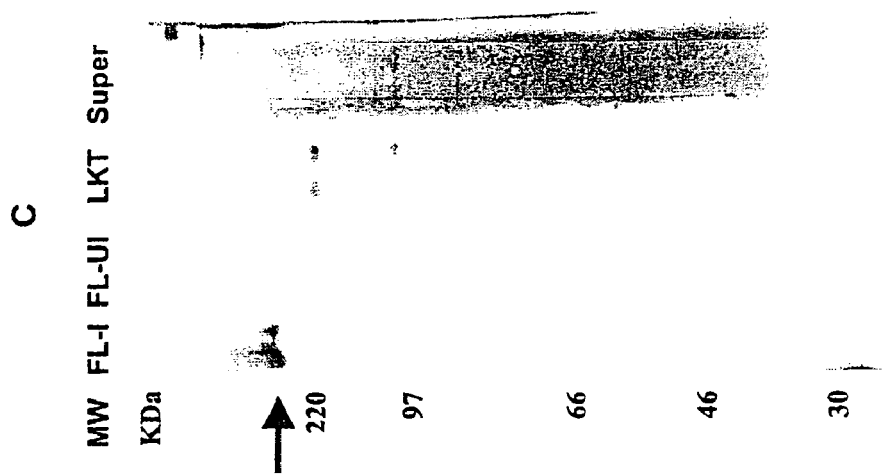
FIG. 7c is a Western blot of whole-cell lysates from *E. coli* clones expressing full-length recombinant leukotoxin probed with the monoclonal anti-leukotoxin antibody.

Creation of Full-length Recombinant Leukotoxin and its Toxicity to Bovine Peripheral Blood Polymorphonuclear Cells The entire leukotoxin gene (9,726 bp) was cloned into the pQE30 expression vector. Unlike certain truncated versions of the leukotoxin protein, full-length recombinant leukotoxin upon expression was not toxic to *E. coli* host cells. When whole-cell lysates from clones expressing full-length leukotoxin were subjected to western blot assays, both polyclonal (not shown) and monoclonal antileukotoxin antibodies reacted to high-molecular weight (>220 kDa) protein species (FIG. 7c). In this Figure, MW is molecular weight markers; Lkt, is affinity-purified leukotoxin from *F. necrophorum*; FL-I and FL-UI are full-length clone induced or uninduced with IPTG; Super is concentrated *F. necrophorum* A25 culture supernatant. Additionally, the arrows denote the positions of the reactive BSBSE band in FIG. 7b and the full-length leukotoxin in FIG. 7c. The amount of full-length leukotoxin in the culture supernatant in panel C was insufficient to be visualized as a distinct band in this blot. The protein was extremely unstable, as evident by the presence of numerous smaller molecular weight species, which presumably represent breakdown products. This instability was also observed with native leukotoxin that was immunoaffinity-purified from *F. necrophorum* culture supernatants. Antisera raised against all the truncated leukotoxin polypeptides, including the C-terminal FINAL polypeptide, reacted to recombinant leukotoxin suggesting that the protein may be expressed in its full-length (data not shown). As expected, antibody raised against the upstream polypeptide failed to react to the full-length recombinant leukotoxin.

Figure 8:
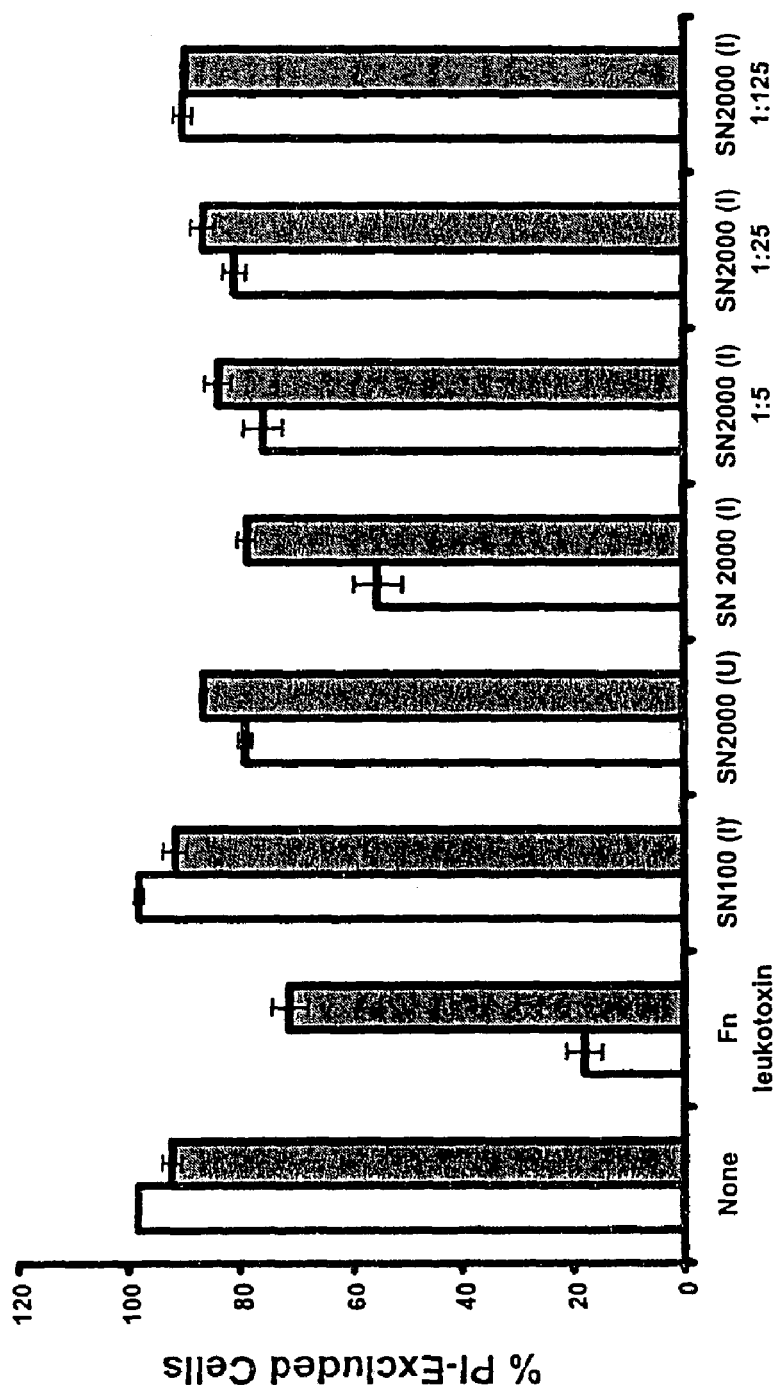
FIG. 8 is a graph illustrating the evaluation of leukotoxic activity by flow cytometry.

Bovine peripheral polymorphonuclear leukocytes exposed to whole-cell lysates of full-length or truncated recombinant clones (12 mg/ml protein) prior to or after induction with IPTG were tested for membrane integrity using propidium iodide exclusion and flow cytometry. Control cells untreated with leukotoxin gave a baseline value of 5.4% PI-staining cells (FIG. 8). In this Figure, membrane damage was assessed by staining of the cells with propidium iodide. Shown are the values obtained after counting 10,000 PMNs (stippled bars) or the lymphocyte fraction (hatched bars). Cells were untreated (control), treated with 200 units of affinity purified leukotoxin from *F. necrophorum* (Fn leukotoxin) or lysates of *E. coli* harboring expression plasmids bearing the upstream polypeptide (pSN100) or the full-length lktA open reading frame (pSN2000). The "U" and "I" designations refer to lysates from uninduced cultures and cultures induced with 1 mM IPTG, respectively. Induced lysates were also tested after 1:5, 1:25, and 1:125 dilutions in PBS. The results shown are the averages of three experiments and the standard deviation is indicated.

The addition of 200 MTT units of affinity-purified native leukotoxin resulted in 75.4% of the PMNs taking up the dye. An MTT unit of the toxin is defined as the reciprocal of the dilution causing a 10% decrease in MTT-dye reduction activity. The affinity-purified leukotoxin preparation used in this study had an activity of $2\times10^5$ units/ml. Lysates from the clone expressing the upstream polypeptide (SN100) did not increase the percentage of PI-staining cells, indicating that the truncated form of this protein lacked membrane-damaging activity. Whole-cell lysates from *E. coli* carrying recombinant full-length leukotoxin gene (SN2000), uninduced with IPTG, gave rise to 9.6% PI-staining bovine PMNs, whereas lysates from induced clones gave 27.3% staining PMNs. The low percentage of damaged cells from the uninduced lysate resulted from leaky expression of the toxin with this vector, consistent with the results obtained by western blot analysis (not shown). The membrane damaging activity in the induced lysate was proportionately lost when the samples were diluted in phosphate-buffered saline. The data indicate that recombinant full-length leukotoxin is toxic to bovine neutrophils.

Figure 9:
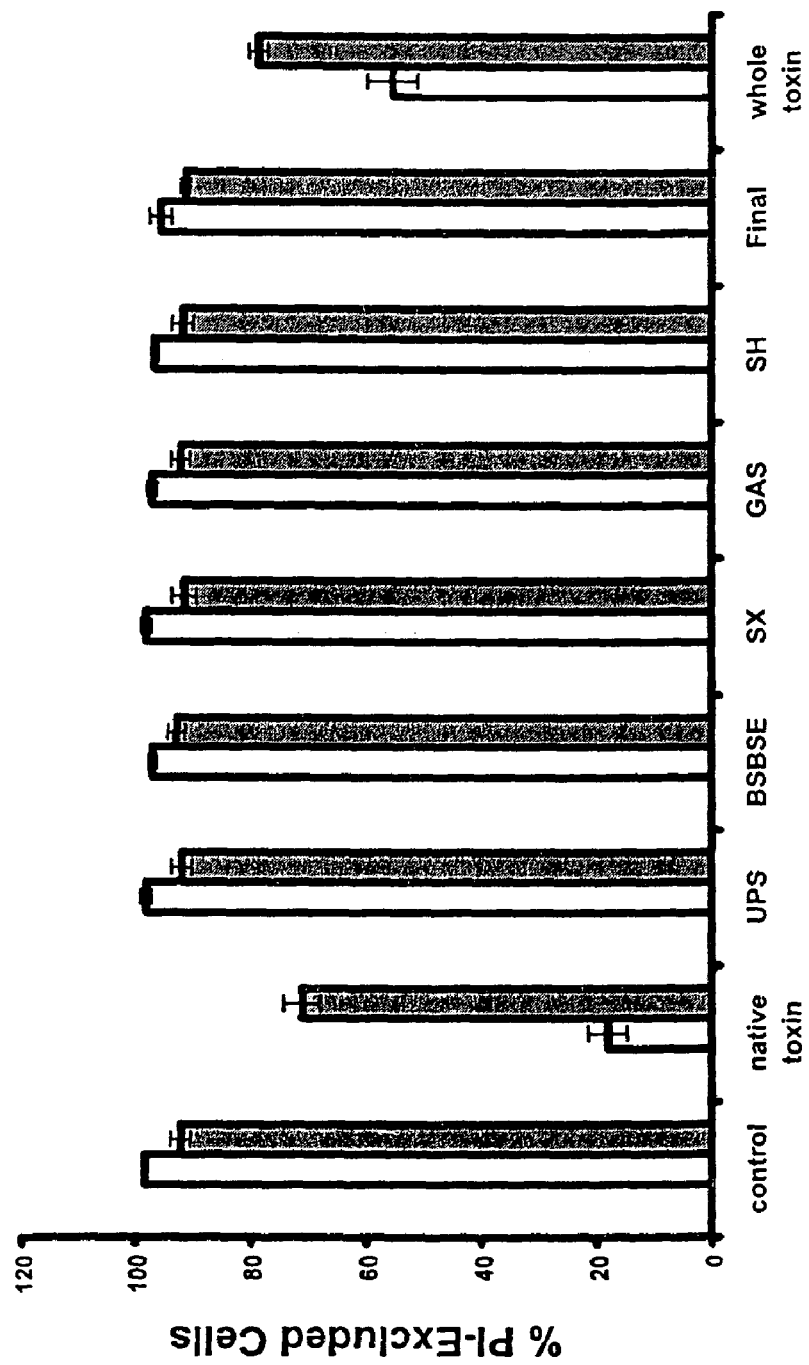
FIG. 9 is graph illustrating the toxicity of the recombinant leukotoxin and the truncated polypeptides by flow cytometry.

Preparations of PMNs had residual contaminating cells of smaller size and granularity, which were found to be predominantly lymphocytes by immunophenotyping with anti-CD3 and anti-IgM specific monoclonal antibody. These cells were gated, and the effects of various leukotoxin preparations on the viability of these cells were measured as described for PMNs. Untreated control lymphocytes gave a baseline value of 13.6% staining cells, whereas inclusion of 200 units of affinity-purified native leukotoxin resulted in 31.3% of the lymphocytes taking up the PI (FIG. 8). The apparently lower sensitivity of lymphocytes compared to PMNs is characteristic of *F. necrophorum* leukotoxin. Furthermore, the recombinant toxin displayed the same degree of activity against lymphocytes as did the native leukotoxin. Among lymphocytes treated with lysates from *E. coli* carrying uninduced recombinant full-length lktA, 12.8% were PI-positive compared to 19.2% obtained with lysates from induced clones. Thus the expressed recombinant leukotoxin had toxicological properties similar to those of the native leukotoxin purified from *F. necrophorum* culture supernatant. Lysates from *E. coli* with IPTG-induced expression of the leukotoxin truncated polypeptides or the upstream polypeptide did not display membrane-damaging activity against either bovine PMNs or the lymphocyte-containing population (FIG. 9). In this Figure, membrane damage was assessed by staining of the cells with propidium iodide. Shown are the values obtained after counting 10,000 PMNs (stippled bars) or the lymphocyte fraction (hatched bars). Cells were untreated (control), treated with 200 units of affinity purified leukotoxin from *F. necrophorum* (native toxin), lysates from IPTG-induced cultures of clones expressing the truncated polypeptides (ups, BSBSE SE, SX, GAS, SH, and Final) or the whole recombinant leukotoxin (whole toxin). The results shown are the averages of three experiments and the standard deviation is indicated.

Presence of the Leukotoxin Determinant in *F. necrophorum* Isolates

Figure 10:
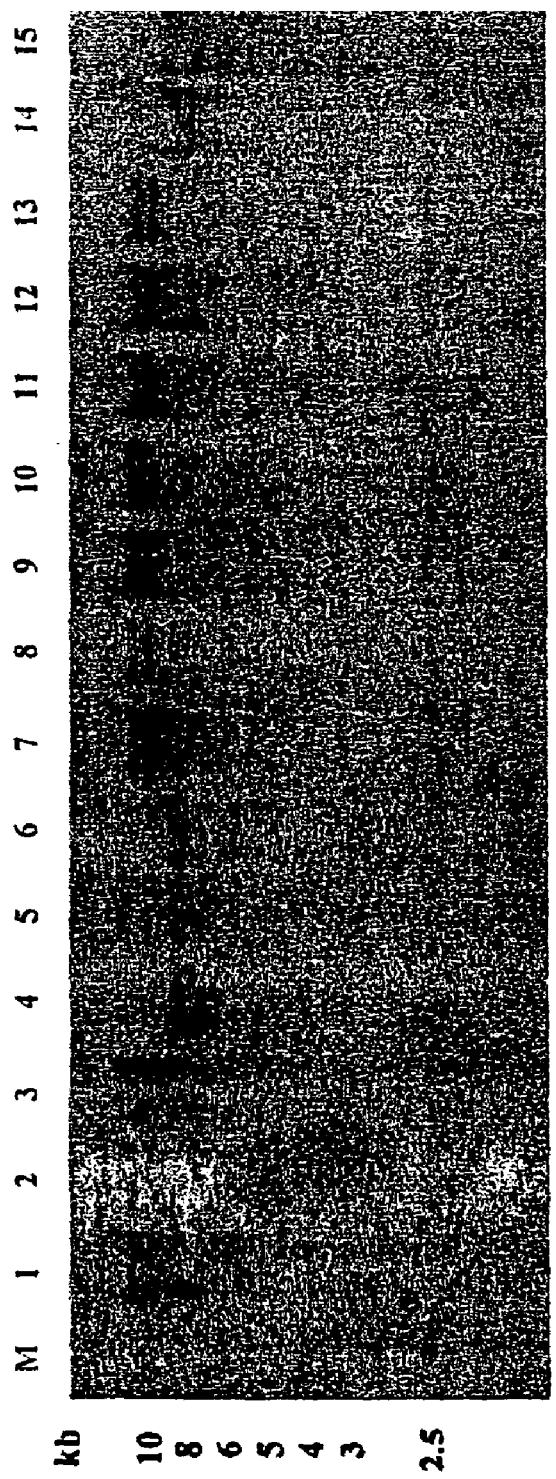
FIG. 10 is an illustration of the hybridization patterns of radiolabeled lktA with Southern blotted HaeIII digested restriction fragments of genomic DNAs from *F. necrophorum* subsp. *necrophorum* isolates from liver abscesses.

The leukotoxin gene was cloned and sequenced from *F. necrophorum* subsp. *necrophorum* A25, a strain originally isolated from a bovine liver abscess. Southern blot hybridization of the chromosomal DNA extracted from various *F. necrophorum* strains of both subspecies isolated from ruminal contents or liver abscesses was carried out using the leukotoxin ORF as a probe (FIG. 10). In this Figure, *F. necrophorum* subsp. *necrophorum* from liver abscesses are in lane 1 which is strain A21; lane 2 which is A25; and lane 3 which is A39. *F. necrophorum* subsp. *necrophorum* from ruminal contents are in lane 7 which is RA13; lane 8 which is RA15; lane 9 which is RA16; lane 10 which is RA18; lane 11 which is RA26; lane 12 which is RA28; and lane 13 which is RA29. The *F. necrophorum* subsp. *funduliforme* isolates from liver abscesses are in lane 4 which is B17; lane 5 which is B29; lane 6 which is B35 or ruminal contents which are in lane 14 which is RB33; and lane 15 which is RB37. Strains are described in reference 24. M, DNA molecular weight markers. The restriction endonuclease HaeIII was used to digest the chromosomal DNA from *F. necrophorum* isolates. A single recognition site for this enzyme occurs 5,933 bp from the start codon in the lktA ORF. Thus, two hybridizing fragments should be present in strains carrying this gene. All strains of *F. necrophorum* subsp. *funduliforme* isolated from liver abscesses (B17, B29, and B35) or ruminal contents (RB33 and RB37) were identical in their hybridization patterns showing two bands at approximately 7 and 8 kb each. Also, all isolates of *F. necrophorum* subsp. *necrophorum*, except A39, isolated from liver abscesses (A21 and A25) and those isolated from ruminal contents (RA13, RA15, RA16, RA18, RA26, RA28, and RA29) had identical hybridization patterns showing two bands of approximately 10 and 11 kb each. A single band of approximately 10.5 kb, presumably a doublet, hybridized to the leukotoxin gene in chromosomal DNA of strain A39 (FIG. 10, lane 4). This suggests that some heterogeneity may be present in the leukotoxin locus sequences among strains of *F. necrophorum* subsp. *necrophorum*. However, the hybridization pattern does appear to be a good indicator for subspecies determination.

EXAMPLE 3

Construction of Truncated Forms of the Leukotoxin

A 3.5 kb sequence from the 5' end of lktA gene was amplified by PCR and cloned in-frame in the expression vector pQE 30 (Qiagen Corporation). Induced expression of this truncated version of the leukotoxin protein with IPTG resulted in the immediate cessation of growth and caused lysis of the host *E. coli* cells. In order to obtain better expression of recombinant protein, smaller truncations of the leukotoxin gene were constructed. Polymerase chain reaction using thermostable polymerase with proof reading ability (EXTaq; Takara Corp.) was used to amplify five overlapping regions of the leukotoxin gene. The forward primers were designed to contain a SacI site, and the reverse primers had a XmaI site. *F. necrophorum* A25 chromosomal DNA was used as the template, and the amplified products were digested with restriction enzymes SacI and XmaI, and cloned in-frame in the His-tag expression vector pQE 30. Five truncated leukotoxin proteins and the C-terminus of the upstream protein were purified using nickel chelation chromatography to apparent homogeneity as indicated by silver-stained SDS-PAGE gels. The proteins were then tested for their reactivity with polyclonal antisera raised in rabbits against affinity purified native leukotoxin using western blot analysis. Purified proteins were injected in rabbits to produce polyclonal antisera, which in turn were used to carry out western blot analysis and neutralization tests (Table 2). Antisera raised against each protein recognized native leukotoxin from *F. necrophorum*. Antisera directed against the BSBSE9 and GAS polypeptides were able to neutralize the activity of native leukotoxin. Thus the cloned ORF does indeed represent the *F. necrophorum* leukotoxin.

Immunogenicity of the Inactivated Recombinant Leukotoxin in Mice

Immunogenicity and protective effects of the inactivated recombinant full length, and truncated leukotoxins are evaluated in comparison with the native leukotoxin (culture supernatant of *F. necrophorum*, strain A25). Five overlapping truncations and the recombinant full-length leukotoxin are purified using the nickel-affinity columns. The treatment groups include control (0.2 ml PBS), native leukotoxin, recombinant full length, and truncated leukotoxins individually or in combination (all five truncations individually, and a mixture of all five truncated proteins in equimolar ratio). Additionally, a mixture of the two truncated proteins BSBSE and GAS in equimolar concentrations is tested for immunogenicity, because polyclonal antisera raised against these two proteins neutralize the activity of native leukotoxin against bovine neutrophils. Each leukotoxin preparation is tested at

TABLE 2

Characterization of the Truncated Upstream and Leukotoxin Proteins

| Truncated Leukotoxin Proteins (N to C terminal) | Number of Amino Acids | Size (in Daltons) | Recognized by Anti-native Leukotoxin Antibodies | Antisera Raised Against Truncated Proteins Recognized Native Leukotoxin | Antisera Neutralizes Activity of Leukotoxin Against PMNs |
|---|---|---|---|---|---|
| UPS 9 | 339 | 38324 | − | − | − |
| BSBSE 9 | 377 | 40810 | + | + | + |
| SX 7 | 926 | 97453 | + | + | − |
| GAS 15 | 713 | 71949 | − | + | + |
| SH 12 | 628 | 63457 | − | + | − |
| FINAL 2 | 774 | 80590 | + | + | − |

Production of an Inactivated Recombinant Leukotoxin Vaccine

The immunogenicity and protective immunity of the recombinant full length and truncated leukotoxin proteins is determined in mice and compared to the efficacy of immunization with inactivated native leukotoxin in *F. necrophorum* culture supernatant. The usefulness of the mouse model in studying experimental Fusobacterium infections has been well documented (Abe et al., 1986, Emery and Vaughn, 1986).

Vaccine Preparations

Purified recombinant leukotoxins (described above) including the full-length protein are inactivated by the addition of formalin (final concentration 0.3%) and homogenized with Ribi or other suitable adjuvant (10% vol/vol; Ribi Immunochem, Hamilton, Mont.). The native leukotoxoid vaccine is prepared with culture supernatant from *F. necrophorum* subsp. *necrophorum*, strain A25 grown in PRAS-BHI broth (Saginala et al., 1997). The leukotoxic activities of the recombinant leukotoxin and culture supernatant, before and after formalin inactivation, are then tested by MTT-dye reduction assay using bovine polymorphonuclear (PMN) leukocytes as target cells (Tan et al., 1992). The quantity of native leukotoxin is then assayed using a sandwich ELISA using purified monoclonal antibody (Tan et al., 1994b).

10 and 50 μg doses (total protein concentration), administered subcutaneously on days 0 and 21. Six mice (7-8 wk old BALB/c) are used in each treatment group. Blood samples are collected on days 0, 14, 21, 35, and 42. Serum is stored at −70° C. until assayed for antileukotoxin antibody. After the last blood sampling (on day 42), mice are challenged intraperitoneally with 0.4 ml of late-log phase *F. necrophorum* strain A25 culture (6-7 hour culture in PRAS-BHI broth with an absorbance of 0.65 at 600 nm and with a cell concentration of approximately 1 to $5 \times 10^8$ CFU/ml). The number of bacteria used for inoculation is enumerated by viable counts on blood agar plates in an anaerobic glove Box (Forma Scientific, Marietta, Ohio). Mice are observed for 4 days after challenge to record mortality and clinical signs, and those that survive the challenge are euthanized. Mice are then necropsied and examined grossly for abscesses in the liver. Additionally, other organs and liver tissue will be cultured for anaerobic bacterial isolation.

Following this study, the efficacious dose and the recombinant leukotoxin preparation is selected and one more immunization and challenge study in mice to confirm the protective effect of recombinant leukotoxin is conducted. Groups of 7-8 week old BALB/c mice (10 per group) are used and each group receives one of the following leukotoxin preparations: most immunogenic recombinant leukotoxin protein, combination (two or more) of most immunogenic recombinant leukotoxin proteins, and native leukotoxin (*F. necrophorum* culture supernatant). The leukotoxin proteins are inactivated with 0.3% formalin, mixed with Ribi or any other suitable adjuvant and emulsified with a homogenizer and administered subcutaneously on days 0 and 21. Blood samples are collected on days 0, 14, 21, 35 and 42. Serum samples are assayed for antileukotoxin antibody. After the last blood sampling (on day 42), mice are challenged as described above. Overlapping variants of effective polypeptides (the truncated protein fragments) are identified and are constructed in order to identify the polypeptide sequences that are most effective in conferring protection.

Determination of Antileukotoxin Antibody Induced by Immunization

Mouse serum is analyzed for antileukotoxin antibody by two methods. First, serum samples are assayed for leukotoxin neutralizing antibody by testing its ability to neutralize the toxin using the MTT dye reduction assay with mouse and bovine PMNs as the target cells (Saginala, et al., 1996b; Tan et al., 1994a). Second, serum samples are tested for antileukotoxin IgG antibodies by enzyme linked immunosorbent assay (ELISA) using affinity-purified leukotoxin as the coating antigen. Affinity purification of the leukotoxin is carried out using monoclonal antibody MAbF7B10 (Tan et al., 1994b).

Tris-HCl [pH 8.0] and 1 mM EDTA) and was run for 20 hours in a cesium-chloride gradient (60% to 43.5%) containing ethidium bromide (0.4 mg/ml final volume). The chromosomal DNA band was extracted with cesium-chloride saturated isopropanol to remove ethidium bromide and dialyzed against double distilled water. DNA concentration and purity were checked spectrophotometrically.

The primers were designed to amplify the leukotoxin gene as five overlapping truncations (Table 3). The sites for annealing of the primers were chosen, so that there is an overlap of approximately 100 bp with the adjacent truncated leukotoxin gene product. Each forward primer was designed to contain a SacI site and reverse primers carried a XmaI site (Table 3). PCR amplifications were carried out under following conditions using a thermostable DNA polymerase with a proofreading function ExTaq (Takara Corp., Madison, Wis.): initial denaturation 94° C. for 3 min; 36 cycles of denaturation 94° C. for 1 min, 59° C. for 45 sec, 67° C. for 30 sec, and 72° C. for 1 to 3 min (at min per kb), and a final extension at 72° C. for 4 min.

TABLE 3

PCR primers used for amplifying truncated leukotoxin gene segments.

| Truncated segment | Location in lktA gene (bp) | Designation | Primer Sequence[a] |
|---|---|---|---|
| bsbse | 1–22 | BS-START | tccgagctcATGAGCGGCATCAAAAATAACG |
|  | 1130–1112 | BS-END | tcgccccgggATAGGAGAAATAGAACCTG |
| sx | 919–940 | SX-START | tccgagctcGGGAGATTTATAAAGAAAGAAG |
|  | 3698–3679 | SX-END | tcgccccgggGATCCGCCCCATGCTCCAAC |
| gas | 3553–3572 | GAS-START | tccgagctcGGAGCTTCTGGAAGTGTTTC |
|  | 5693–5674 | GAS-END | tcgccccgggGTACTATTTTTTATATGTGC |
| sh | 5623–5641 | SH-START | tccgagctcGCTGCAGTAGGAGCTGGAG |
|  | 7510–7492 | SH-END | tcgccccgggCTGCAGTTCCCAAACCACC |
| final | 7405–7425 | FIN-START | tccgagctcGGAATTAAAGCCATTGTGAAG |
|  | 9726–9706 | FIN-END | tcgccccgggTCATTTTTTCCCTTTTTCTCC |

[a]Lower case letters in primer sequences represent extra bases added to incorporate restriction sites.

EXAMPLE 4

DNA Extraction and Polymerase Chain Reaction

Figure 11:
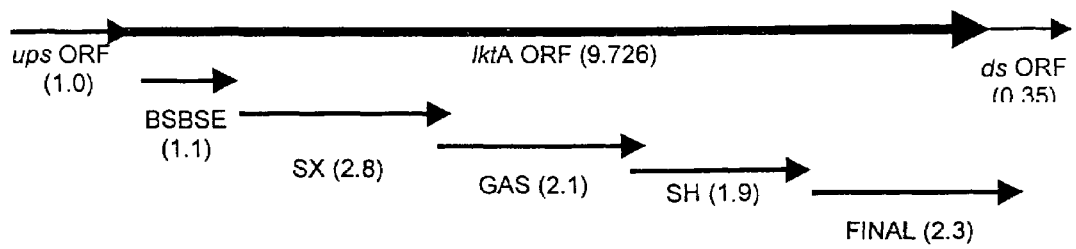
FIG. 11 is an illustration of the expression clones for the truncated proteins designated UPS, BSBSE, SX, GAS, SH, and FINAL.

Chromosomal DNA was isolated from *F. necrophorum* subspecies *necrophorum*, strain A25. Briefly, *F. necrophorum* was grown overnight in a PRAS-BHI broth in serum bottles at 39° C. Cell pellets were resuspended in TES buffer (25% sucrose, 50 mM Tris-HCl [pH 7.5] and 1 mM EDTA), spheroplasted with lysozyme at room temperature for 30 min, and lysed using sarkosyl in the presence of proteinase K at 60° C. for 1 hour. The DNA was extracted with buffer-saturated phenol and chloroform and was precipitated in 2.5 volumes of ice-cold ethanol and ⅒ volume of sodium acetate (3 M, pH 5.2). The DNA pellet was resuspended in TE buffer (10 mM Directional Cloning in an Expression Vector The amplified gene products which are overlapping truncations extending from 5' to 3' end of the leukotoxin gene (lktA), were named BSBSE, SX, GAS, SH, and FINAL (FIG. 11). In this Figure the numbers in parentheses indicate the size in kilobases of each insert. They were extracted with phenol and chloroform and precipitated with ethanol as described above. The amplified lktA gene products and expression vector pQE30 (Qiagen Corp., Valencia, Calif.) were digested with restriction endonucleases SacI and XmaI as per manufacturer's instructions (New England Biolabs, Beverly, Mass.). After digestion, the vector and insert DNA were phenol and chloroform extracted, ethanol precipitated, and ligated overnight at 16° C. using T4 DNA ligase (Promega Corp., Madison, Wis.). Ligated DNA was digested with restriction enzyme KpnI before transforming chemically competent *E. coli* M15 cells as per standard procedures. Restriction sites for KpnI is absent in the entire lktA gene and present in a single location between SacI and XmaI sites in pQE 30. The expression vector pQE 30 lacks blue/white selection, thus the above manipulation helped us to enrich clones that carry truncated leukotoxin gene products. The transformants were plated on Luria-agar plates containing ampicillin (100 ug/ml) and kanamycin (20 ug/ml) to select for clones containing plasmids pQE30 and pRep4.

Expression of Truncated Leukotoxin Polypeptides

Plasmid DNA from the transformants were purified using Wizard SV miniprep columns (Promega), and the orientation of the insert was checked by sequencing with a vector specific 5'QE primer which anneals upstream to the MCS using a Applied Biosystems 373A automated sequencer. Positive clones were induced for the expression of polypeptides with IPTG, the whole cell lysates from uninduced and induced were compared for immunoreactive polypeptides in a western-blot using polyclonal antisera raised in rabbits against affinity purified native leukotoxin (Tan et al, 1994d).

Antigen Preparation

Due to the presence of its codons in the sequence upstream of the MCS in the vector pQE 30, six histidine residues are added in the N-terminus of the expressed polypeptides. The expressed polypeptides were purified using nickel-affinity columns under denaturing conditions using guanidium hydrochloride, as per the manufacturer's instructions (Qiagen). The column purified polypeptides were dialyzed for 48 hours at 4° C. against sterile phosphate buffered saline (0.1 M, pH 7.2) to remove any traces of urea, and concentrated in Ultrafree-Biomax 30 filters (Millipore Corp. Bedford, Mass.), which retains molecules of sizes over 30 kDa. The protein concentrations were analyzed using the BCA assay (Pierce, Rockfort, Ill.) and the purity checked with SDS-PAGE analysis followed by silver staining. Native leukotoxin from *F. necrophorum* culture supernatant was purified using immunoaffinity columns with anti-leukotoxin monoclonal antibody (F7B10) as described previously. Also, leukotoxoid vaccine (12 hours culture supernatant inactivated with 0.3% formaldehyde) was made as described previously (Saginala et al., 1997).

Preparation of Polyclonal Antiserum against Truncated Polypeptides

Five New-Zealand White rabbits were injected intramuscularly with the five truncated leukotoxin polypeptides (0.5 mg/animal) precipitated with aluminum hydroxide. A booster dose was given on day 21 (0.5 mg/animal). Serum samples were collected on days 21 and 42 and antileukotoxin titers were determined by indirect ELISA using affinity purified native leukotoxin. Leukotoxin neutralizing activities of the 42 day serum samples were determined by the MTT dye neutralization assay. A neutralization ratio, which was the dilution of the antiserum that caused neutralization divided by its ELISA titer, was calculated for each truncated polypeptide.

EXAMPLE 5

Vaccine and Immunization

One hundred (100) 8 to 10 week old mice, identified by ear-markings, were randomly divided into 10 groups of 10 mice each. The groups received five truncated leukotoxin polypeptides (BSBSE, SX, GAS, SH, and FINAL) individually, a mixture of BSBSE and GAS, a mixture of all five truncated polypeptides, affinity purified native leukotoxin, inactivated culture supernatant, or PBS emulsified with Ribi adjuvant. Each mouse was injected subcutaneously (in two locations of 100 μl each between the shoulder blades) on day 0 and day 21 with 200 μl of one of the above preparations. The total amount of antigen in each injection (except with culture supernatant or PBS) was 10 μg per animal. Inactivated culture supernatant (12 mg/ml protein concentration) was used without dilution to reconstitute Ribi adjuvant (Ribi Immunochem, Hamilton, Mont.) and each mouse was injected with 200 μl (2.4 mg protein) of the emulsified preparation. Negative control group received 200 μl of PBS emulsified with the Ribi adjuvant.

EXAMPLE 6

Determination of Antileukotoxin Antibodies Induced by Immunization

Blood for serum separation was collected from the right saphenous vein of each mouse on days 0, 21 and 42, and directly from the heart after euthanasia. Antileukotoxin antibody titers were assayed by an indirect ELISA as described previously with slight modifications. Briefly, 96-well microtiter plates (Falcon Probind assay plates, Beckton Dickinson Labware, Lincoln Park, N.J.) were coated with 50 μl (2 μg/ml) per well of affinity purified native leukotoxin at 37° C. for 2 hours. The wells were blocked with 3% bovine serum albumin (Sigma Chemical Company, St. Louis, Mo.) in PBS at 37° C. for 2 hours. Fifty μl of a 1 in 25 dilution of serum samples in PBS-T (0.05% Tween 20 in PBS) were added in duplicate and the plates were incubated at 37° C. for 1 hour. Following 6 washes with PBS-T, 100 μl of biotinylated goat anti-mouse immunoglobulin (Accurate Chemicals and Scientific Corp., Westbury, N.Y.) was added to each well and incubated at 37° C. for 1 hour. The plates were washed 6 times with PBS-T and 50 μl of streptavidin conjugated with horseradish peroxidase was added to each well, and incubated at 37° C. for 1 hour. After washing the wells 6 times with PBS-T, 100μl of ABTS substrate (2,2'-azino-di-[3-ethyl-benzthiazoline-6-sulfonic acid]; Sigma) and $H_2O_2$ in phosphate-citrate buffer (pH 4.0) was added to each well, and the plates were incubated for 30 min, or until color development, at room temperature. The absorbance was measured colorimetrically at 410 nm in a 96-well plate reader (Molecular Devices, Calif.).

EXAMPLE 7

Experimental Challenge with *Fusobacterium necrophorum*

*Fusobacterium necrophorum* subsp. *necrophorum*, strain A25 was grown to an $OD_{600}$ of 0.7 in PRAS-BHI broth and 0.4 ml of this late-log-phase culture was injected intraperitoneally in mice. The inoculum had a bacterial concentration of $4.7 \times 10^8$ CFU/ml as determined by spread-plating on blood agar plates (Remel, Lenexa, Kans.) incubated in an anaerobic glove box (Forma Scientific, Marietta, Ohio). Mice were observed for 4 days post-challenge to record clinical signs and mortality. Mice that survived for 4 days post-challenge were euthanized, necropsied and examined for the presence of abscesses in liver and other internal organs.

EXAMPLE 8

Enumeration of *Fusobacterium necrophorum* Load in the Liver

Livers from mice were collected at necropsy, weighed and homogenized in a tissue homogenizer for 1 min in PRAS-BHI broth. A 10-fold dilution of the homogenate was taken inside an anaerobic Glove box for further processing. Two hundred μl of modified lactate medium was dispensed into each well of the 96-well tissue culture plate (Falcon, Beckton Dickinson Labware, Lincoln Park, N.J.). Fifty μl of 1 in 10 dilution of homogenated liver was transferred to the wells on the first lane (8 wells) and serially diluted (five-fold) up to the eleventh well. The wells in the 12th lane were negative controls. The plates were incubated in a Glove box at 39° C. for 48 hours. Kovac's reagent (20 μls each) was added to each well to detect indole production, presumptive of *F. necrophorum*. The bacterial load of *F. necrophorum* in liver was enumerated by most probable number (MPN) analysis (Rowe, R., Todd, R., and Waide, J. 1977. Microtechnique for most-probable-number analysis. Appl. Environ. Microbiol. 33:675-680.). Homogenized liver tissue samples were also streaked on blood agar plates and colonies identified using Rapid ANAII system (Innovative Diagnostic Systems, Norcross, Ga.).

EXAMPLE 9

Statistical Analyses

Serum ELISA measurements (absorbance values per ml of serum) were analyzed using Proc Mixed procedure of SAS (SAS systems, Cary, N.C.). The weights of liver and bacterial counts, log-transformed, were analyzed using PROC GLM program of SAS. P-values less than 0.01 were considered significant.

Results

Cloning and Expression of Leukotoxin Gene Truncations

In-frame cloning of the PCR amplified truncations of the leukotoxin gene (lktA) in plasmid pQE 30 was carried out as described above by incorporating restriction sites for SacI and XmaI in the forward and reverse primers respectively. Inducing the clones carrying various truncations did not produce inclusion bodies in the *E. coli* host cells. However, purification of the expressed polypeptides under native conditions was unsuccessful. Therefore, polypeptides were purified using nickel affinity columns after denaturation with guanidium isothiocyanate. The denatured truncated polypeptides, after dialysis against PBS, lacked toxicity to PMNs.

Antileukotoxin Antibody Titers in Rabbits.

The anti-leukotoxin antibody titers in rabbits injected with truncated polypeptides are shown below in Table 4. Antisera raised against truncated leukotoxin polypeptides, BSBSE and GAS, neutralized the toxicity of affinity purified native leukotoxin against bovine peripheral PMNs. The neutralizing activities for polyclonal antisera raised against BSBSE and GAS were similar as evident from their identical neutralization ratios (0.146).

TABLE 4

Anti leukotoxin antibody titers in rabbits injected with truncated leukotoxin proteins

| Truncated proteins | Size (in daltons) | LISA titer on day 21 | LISA Titer on day 42 (b) | Neutralization titer on day 42 (a) | Neutralization ratio (a/b) |
|---|---|---|---|---|---|
| BSBSE | 40810 | 1250 | 10000 | 1460 | 0.146 |
| SX | 97453 | 1000 | 8750 | 0 | 0 |
| GAS | 71949 | 1150 | 8750 | 1280 | 0.146 |
| SH | 63457 | 1000 | 10000 | 0 | 0 |
| FINAL | 80590 | 875 | 9750 | 0 | 0 |

Anti-Leukotoxin Antibody Response in Mice

The mean absorbances per ml of serum, determined by ELISA, from mice vaccinated with various leukotoxin polypeptides are shown in Table 5.

TABLE 5

Anti-leukotoxin antibody response in mice injected with various leukotoxin preparations.

| Vaccine Preparations | D 0 | D 21 | D 42 | D 46 (post-mortem) |
|---|---|---|---|---|
| PBS | 63.6$^a$ | 65.3$^a$ | 66.9$^a$ | 126.3$^d$ |
| BSBSE | 52.9$^a$ | 90.2$^b$ | 179.4$^c$ | 129.1$^d$ |
| SX | 54.1$^a$ | 77.6$^{ab}$ | 186.4$^{c*}$ | 144.5$^d$ |
| GAS | 61.0$^a$ | 77.6$^{ab}$ | 97.1$^{bc}$ | 109.6$^{cd}$ |
| SH | 60.95$^a$ | 101$^{b*}$ | 163.8$^{c*}$ | 130.0$^d$ |
| FINAL | 63.9$^a$ | 66.2$^{ab}$ | 95.7$^{bc*}$ | 121.7$^{cd}$ |
| BSBSE + GAS | 79.7$^a$ | 82.5$^a$ | 161.1$^{c*}$ | 172.7$^{cd*}$ |
| ALL FIVE | 66.1$^a$ | 98.9$^{b*}$ | 189$^{c*}$ | 219$^{d*}$ |
| Native Leukotoxin | 59.6$^a$ | 101.3$^{b*}$ | 235.5$^{c*}$ | 205.2$^{d*}$ |
| Culture Supernatant | 76.4$^a$ | 105.7$^{b*}$ | 205.4$^{c*}$ | 230.1$^{cd*}$ |

Numbers with same superscripts were not significantly different from the ELISA values from mice belonging to same group at a different sampling period.
*Significantly different from negative control (PBS).

On day 21, mice vaccinated with affinity purified native leukotoxin, truncations BSBSE or SH, mixture of all five, or culture supernatant had higher antileukotoxin antibody levels compared to day 0. Serum collected on day 21 from groups vaccinated with truncated polypeptide SH, mixture of five truncations, native affinity purified leukotoxin or culture supernatant, had significantly higher anti-leukotoxin antibody levels compared to the control (PBS) group (p<0.01). There was no significant rise in the antibody levels on day 21 among mice vaccinated with truncated polypeptides SX, GAS, FINAL, a combination of BSBSE and GAS or PBS. Mice belonging to group that was vaccinated with culture supernatant, had significantly higher (P<0.01) antibody titers to leukotoxin than mice in other groups.

On day 42, there was a significant increase in antibody response compared to day 21 among mice vaccinated with all leukotoxin preparations except GAS (P<0.01). Anti-leukotoxin antibody levels in serum from mice vaccinated with different leukotoxin polypeptides (including GAS) were significantly higher compared to the control. The antibody response to a mixture of BSBSE+GAS was similar to BSBSE alone but higher than GAS polypeptide. The antibody response to mixture of all five was similar to BSBSE, SX, SH but higher than GAS or FINAL polypeptides. Mice vaccinated with affinity purified native leukotoxin had the highest anti-leukotoxin antibody levels on day 42, followed by those vaccinated with the culture supernatant and a mixture of all five overlapping truncations. The truncated polypeptide GAS failed to raise anti-leukotoxin antibody levels significantly after the second vaccination compared to the day 21.

On day 46, 4 days after challenge with *F. necrophorum* (post-mortem), serum samples from mice vaccinated with leukotoxin polypeptides, BSBSE, SX, and SH, and affinity purified native leukotoxin had lower anti-leukotoxin antibody titers compared to day 42. Anti-leukotoxin antibody levels in mice vaccinated with GAS, FINAL, mixture of truncated polypeptides or culture supernatant had higher antibody levels compared to day 42. Also, anti-leukotoxin antibody levels in mice in the control group (vaccinated with PBS) on day 46 showed a significant increase than serum collected before challenge (day 42). However, antibody levels in mice injected with BSBSE+GAS, mixture of all five, native leukotoxin and culture supernatant were higher than the control group.

Experimental Infection

Following the challenge with *F. necrophorum*, mice in all groups exhibited acute shock within 24 hours perhaps induced by LPS. Mice in the control or in the group vaccinated with inactivated culture supernatant seemed to be affected most. The mice were listless, recumbent and did not seem to consume food or water. Mice vaccinated with various leukotoxin preparations recovered after 2 days post-challenge. Mice in the control group did not recover completely from the symptoms of shock even by day 4 after challenge. Two mice in the control group and one mouse in the group vaccinated with GAS polypeptide died about 36 hours after challenge. Pure cultures of *F. necrophorum* subsp. *necrophorum* were isolated from the heart blood of all three mice.

Hepatic Pathology

Mice were euthanized 4 days after challenge and the internal organs were examined for abscesses. None of the mice vaccinated with leukotoxin truncation SH had any liver abscesses (Table 6).

TABLE 6

Mortality, liver abscess formation, weight of liver and bacterial load in liver in mice vaccinated with leukotoxin preparations after experimental challenge with *Fusobacterium necrophorum*.

| Leukotoxin preparations | Number of dead mice | No. of mice with liver abscess (%) | Average weight of liver (g) | MPN counts in the liver |
|---|---|---|---|---|
| Control (PBS) | 2/10 | 0/8 (0)$^a$ | 1.86 | $5.3 \times 10^6$ |
| BSBSE | 0/10 | 1/10 (10) | 1.29* | $1.2 \times 10^{3*}$ |
| SX | 0/10 | 5/10 (50) | 1.39* | $8.2 \times 10^{5*}$ |
| GAS | 1/10 | 3/9 (33) | 1.32* | $1.5 \times 10^6$ |
| SH | 0/10 | 0/10 (0) | 1.20* | $5.3 \times 10^{2*}$ |
| FINAL | 0/10 | 3/10 (30) | 1.44* | $6.8 \times 10^{5*}$ |
| BSBSE + GAS | 0/10 | 3/10 (30) | 1.27* | $1.4 \times 10^{5*}$ |
| ALL FIVE | 0/10 | 3/10 (30) | 1.33* | $5.5 \times 10^{5*}$ |
| Native leukotoxin | 0/10 | 3/10 (30) | 1.31* | $5.9 \times 10^{4*}$ |
| Culture supernatant | 0/10 | 1/10 (10) | 1.51* | $1.6 \times 10^{4*}$ |

*Differs from the control group ($P < 0.01$)
$^a$Livers lacked abscesses, but were highly congested and icteric.

The eight mice that survived in the control group had highly congested and icteric livers, but had no abscesses. Thirty percent of mice vaccinated with affinity purified native leukotoxin, truncations GAS or FINAL, or mixtures (BSBSE and GAS, or all five truncations) had liver abscesses. Five out of ten mice vaccinated with leukotoxin truncated polypeptide SX developed liver abscesses. However, in the groups vaccinated with the truncated leukotoxin polypeptide BSBSE or inactivated culture supernatant, only one out of 10 had liver abscesses.

The mean weight of livers from the control group was significantly higher than mean weights of livers from other groups. Livers from the group that received inactivated culture supernatant had the next biggest liver size. This correlated with the clinical signs of acute shock displayed by these two groups.

Enumeration of *F. necrophorum* in Liver Tissue

*Fusobacterium necrophorum* subsp. *necrophorum* was isolated from homogenized liver tissue and abscesses from all mice. The counts of *F. necrophorum* from livers of mice injected with any leukotoxin preparation were lower ($p<0.01$) than the control (Table 6). Livers from mice vaccinated with leukotoxin truncations BSBSE or SH showed significantly lower bacterial counts ($p<0.01$) than mice vaccinated with other preparations. Among leukotoxin truncations, SX showed least protection followed by FINAL and GAS polypeptides as evidenced by the bacterial counts in the livers of mice vaccinated with these polypeptides. Bacterial counts were considerably lower among groups vaccinated with mixtures of leukotoxin truncations (BSBSE and GAS or all five truncations), or affinity purified native leukotoxin as compared to the control group but higher than SH, BSBSE or inactivated culture supernatant (Table 6).

The five overlapping truncated leukotoxin polypeptides created allowed expression of the entire leukotoxin gene without toxicity to the *E. coli* host cells. Primers for the amplification of various truncated leukotoxin gene products were designed in such a way that the expressed polypeptides were not toxic to *E. coli* host cells, but were big enough (at least 30 kDa) to be a good immunogen. The nickel affinity column purified polypeptides were tested for purity in terms of contaminating proteins or lipopolysaccharides by silver-staining the SDS-PAGE separated proteins. Because all truncated polypeptides were purified under denaturing conditions, they were not toxic as determined by the MTT assays. *Fusobacterium necrophorum* culture supernatant and affinity purified native leukotoxin were inactivated with 0.3% formalin before injection, thus were nontoxic.

Neutralization of toxicity of *F. necrophorum* leukotoxin against bovine peripheral PMNs by antiserum raised against BSBSE and GAS polypeptides suggested that biologically important domains, such as those responsible for toxicity or host cell receptor binding was located in these regions. Therefore, a mixture of these two polypeptides (BSBSE+GAS) was also used in a vaccine preparation in our challenge experiments with mice.

The significantly higher antibody levels noticed among groups vaccinated with preparations containing full-length leukotoxin proteins (native affinity purified leukotoxin, culture supernatant, or a mixture of recombinant leukotoxin polypeptides containing all five truncations) maybe due to determinant spreading, or due to augmentation of anti-leukotoxin antibody response by the presence of multiple immunodominant epitopes on the leukotoxin protein. Truncated leukotoxin GAS produced a low antibody response. The high hydrophobicity of this polypeptide may be the reason for its reduced immunogenicity. Also, the wells in the ELISA plates were coated with native immunoaffinity purified leukotoxin, and the domains represented by the GAS polypeptide could possibly be hidden and not exposed for the antibodies against GAS polypeptide to bind.

Decrease in anti-leukotoxin antibody levels among various groups of mice on day 46 (4 days after experimental challenge with F. necrophorum) suggested neutralizing effect and clearance of toxin secreted by F. necrophorum used for experimental challenge by these antibodies. Pure cultures of F. necrophorum subsp. necrophorum were isolated from the heart blood of the three mice (two from negative control group and one from group injected with GAS polypeptide) that died on day 2 after challenge, suggesting that death was due to septicemia induced by F. necrophorum. The hepatic tissue from the negative control group showed inflammation, congestion and icterus characteristic of an acute phase response, but showed no abscesses.

Multiple responses including mortality, clinical signs, weights of liver, presence of abscesses, and the bacterial load in liver were considered to evaluate the effectiveness of various vaccine preparations in providing immunity and protection against experimental challenge with F. necrophorum. Leukotoxin truncation SH was a very effective immunogen as evidenced by a rise in anti-leukotoxin antibody levels in serum samples on day 21 or 42. Also, there were no mortality, hepatic inflammation or abscesses in mice vaccinated with this polypeptide after experimental challenge. The mean bacterial load in the livers of mice from this group was the lowest ($5.3 \times 10^2$). Interestingly, leukotoxin truncated polypeptide SH did not induce neutralizing antibodies in rabbits. Production of high-affinity antibodies against certain immunodominant domains that brings about effective opsonization and clearance of leukotoxin in an experimental challenge model may render this truncated polypeptide (SH) a protective antigen.

Vaccination with N-terminal truncation BSBSE or culture supernatant followed by experimental challenge with F. necrophorum caused no mortality, but livers were abscessed in 10% of the mice. Mice vaccinated with BSBSE, however, had less clinical signs of LPS induced shock after vaccinations or challenge, lower liver weights and lower hepatic-bacterial counts compared to mice vaccinated with inactivated culture supernatant.

Native leukotoxin purified by immunoaffinity columns from F. necrophorum culture supernatant was the fourth best vaccine preparation (behind SH, BSBSE, and culture supernatant) in terms of serum antibody levels, protection against formation of liver abscess (30%), and number of bacteria in the liver tissue. The vaccine consisting of a mixture of all five recombinant truncated leukotoxin polypeptides also protected 70% of mice from abscess formation and the bacterial counts in their hepatic tissue were not significantly different from mice that were vaccinated with native leukotoxin.

Truncated polypeptide GAS, although it invoked neutralizing antibodies in rabbits, was a poorer immunogen and protected 67% of the mice in its group from formation of liver abscesses but one of the ten mice in this group died after challenge. As mentioned above, this region could contain domain(s) of toxicological importance such as, target cell binding, biological activities. However, multiple host-factors such as, availability of specific lymphocyte sub-population for clonal selection, type of helper T-cells stimulated, ability to invoke antibodies capable of opsonization, decide if an antibody response to a particular protein is protective in the species of animal tested.

The truncated leukotoxin polypeptide SX provided least protection from liver abscess formation. The number of bacteria in the hepatic tissue of mice vaccinated with GAS or SX were significantly higher ($P<0.01$) than in livers of mice vaccinated with SH, BSBSE, culture supernatant or full-length native or recombinant leukotoxin (mixture of five truncations), but was lower than the mice in the negative control group. A mixture of BSBSE and GAS or the FINAL polypeptides provided only a mediocre protection against experimental challenge. Polyclonal antisera raised in rabbits against BSBSE or GAS neutralized the activity of native leukotoxin against PMNs used as target cells and were thus chosen to be used in combination.

Recombinant truncated leukotoxin polypeptides SH and BSBSE provided significant protection in mice when used as a vaccine individually. Dilution of immunodominant and protective epitopes present within these regions by including other truncated polypeptides as seen in vaccine preparations containing affinity purified leukotoxin or combinations of truncated leukotoxin polypeptides possibly caused a decrease in overall protection. Further studies to test the effectiveness of leukotoxin truncations BSBSE and SH individually or in combination providing protection against natural or experimental infections with F. necrophorum infections need to be carried out. This study provided further credence to the importance of leukotoxin as the major virulence factor of F. necrophorum and the protein carries a domain (s) or epitope (s) that induces protective immunity against experimental infection. The vaccine that produced best antileukotoxin titer did not always afford good protection against experimental infection. Therefore, certain epitopes may be more important in conferring protective immunity to infection. The results of this study suggest that some of these important epitopes reside on the BSBSE and SH polypeptides.

Discussion

Fusobacterium necrophorum subsp. necrophorum is isolated more often than subsp. funduliforme from necrotic abscesses. The strains of subsp. necrophorum produces the high molecular weight leukotoxin in greater quantities than strains of subsp. funduliforme. In this study, we have cloned the leukotoxin gene from the highly virulent F. necrophorum subsp. necrophorum strain A25. The evidence that the lktA determinant encodes the leukotoxin is as follows: (1) the ORF encodes a 336 kDa protein, a size consistent with previous studies of the toxin; (2) the protein encoded by the recombinant lktA determinant is recognized by both polyclonal and monoclonal antibodies raised against purified leukotoxin from F. necrophorum; (3) antisera raised against polypeptides from the cloned lktA determinant recognized the native toxin in western blots; (4) antisera raised against two of the truncated polypeptides neutralized the toxic activity of the leukotoxin; and (5) the recombinant protein expressed in E. coli is relatively more toxic to bovine neutrophils as compared to bovine lymphocytes. These differing degrees of toxicity toward neutrophils relative to lymphocytes is also observed with leukotoxin that was affinity-purified from F. necrophorum culture supernatants.

Figure 3:
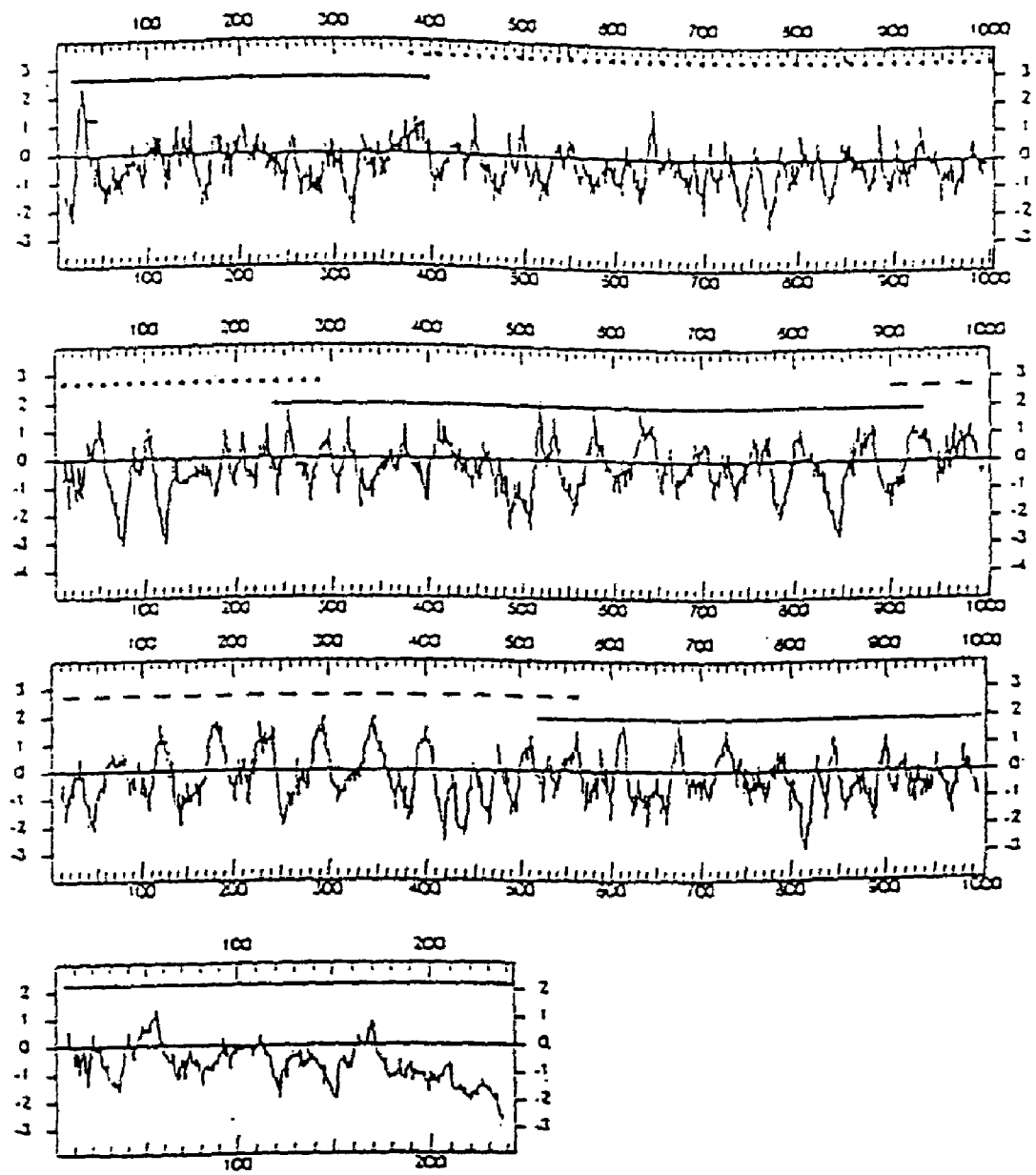
FIG. 3 is a Kyte-Doolittle hydropathy plot of the leukotoxin from *F. necrophorum*.

The leukotoxin ORF is 9,726 base pairs long encoding a 3,241 amino acid protein with an overall molecular mass of 335,956 daltons. The DNA and deduced amino acid sequences were compared with sequences in Genbank but no significant (greater than 25% identity) similarities were found with other bacterial toxins. For example, the closest identity was found with HmwA from Haemophilus influenzae (22% or 356 out of 1,625 residues). Other similar homologies were found in SrpA from Streptococcus cristatus (17% or 388 out of 2,239 residues), OmpA from Ricketsia australis (21% or 321 out of 1,489 residues) and the 190 kDa surface antigen of *Rickettsia ricketsii* (21% or 379 out of 1,770 residues). Other Thus, the *F. necrophorum* leukotoxin appears to be distinct from all known leukotoxins and RTX-type toxins. When the deduced amino acid sequence of the lktA region was subjected to the Kyte-Doolittle hydropathy analysis (FIG. 3), 14 sites of sufficient length and hydrophobic character to be potential membrane spanning regions, were found. Upstream to the leukotoxin ORF is an open reading frame of at least 1.4 kb in length, which is in the same orientation. It encodes a protein that has some sequence identity to the heme-hemopexin utilization protein (UxuB) of *Haemophilus infuenzae*.

Additionally, the protein is larger than any bacterial exotoxins identified to date and shows no sequence similarity to other known leukotoxins. Thus, this protein may represent a new class of bacterial leukotoxins. The protein is unusual in that it is devoid of cysteine. This is not a characteristic of proteins from anaerobes, as evidenced by the normal content of cysteine residues in the clostridial toxins including *Clostridium botulinum* neurotoxin, *Cl. difficile* cytotoxin B, *Cl. septicum* alpha-toxin, and *Cl. tetani* tetanus toxin (Genbank accession numbers AB037166, AB217292, D17668, and X06214, respectively). The leukotoxin protein has a sequence at its N-terminus that has the properties of a signal sequence. This may indicate that the protein is exported across the cytoplasmic membrane in *F. necrophorum* in a Sec pathway-dependent manner.

The DNA sequences flanking lktA suggests that this toxin gene may be part of a multigene operon with at least one ORF upstream and another downstream of this gene. The activity of the LktA protein expressed in *E. coli* indicates that the other proteins encoded in the putative leukotoxin operon are not required to produce a biologically active toxin. Their role may be in secretion of the toxin across the cytoplasmic and outer membranes of *F. necrophorum* into the culture fluid.

If the lktA determinant is part of an operon, it would be greater than 12 kb in length. A dilemma with such a large operon might be to efficiently translate the messenger RNA species without premature dissociation of ribosome from the message. A peculiarity in the cloned region is an abundance of potential ribosome binding site sequences. Within the cloned region, there are 26 occurrences of GGAGG, which is a perfect match to the sequence at the 3' end of the 16S rRNA. The complementary sequence, CCTCC, which has the same G+C content but does not act as a ribosome binding site, is present only two times in the sequence. The abundance of the GGAGG sequence could provide translation reinforcement sequences to help ensure that a ribosome remains associated with the message and completes the translation of the ORFs. The abundance of the putative RBS sequence (GGAGG) is due to the presence of di-glycine repeats in the amino acid sequence. The GGA glycine codon occurs 263 times in the leukotoxin ORF and 24 of the 26 occurrences of GGAGG in the 11,130 bp sequenced to date correspond to tandem repeats of this codon. This feature of the amino acid sequence in the protein may provide the additional benefit of enabling more efficient translation of the message.

Expressing the 3.5 kb sequence from the 5' end of lktA caused immediate cessation of growth and lysis of *E. coli* carrying this recombinant expression vector. Creation of overlapping truncations allowed the expression of the entire leukotoxin gene without significant toxicity to the *E. coli* host cells. Polyclonal antileukotoxin antiserum reacted strongly to three truncated polypeptides (BSBSE, SX and FINAL) and more weakly to the other two truncated polypeptides (GAS and SH) in western blot analysis. This low reactivity was not due to poor immunogenicity of these relatively hydrophobic polypeptides, because both polypeptides (GAS and SH), produced high antibody titers in rabbits. Thus, it may been due to the tertiary folding pattern of leukotoxin under native conditions. The toxin being a secreted protein, would have its hydrophobic domains internalized when the protein was properly folded. The epitopes corresponding to these domains may not be as accessible to the immune system. Antibodies against these epitopes would thus be underrepresented when the whole un-denatured toxin is used as the immunogen. Interestingly, antibodies to one of these polypeptides, GAS, was neutralizing. Thus at least some of the critical epitopes are available in the active toxin.

The intact leukotoxin gene was introduced into *E. coli* under the control of the lac promoter. Inducible expression of full-length leukotoxin protein was achieved without any recognizable toxicity to *E. coli* host cells. Expression of the full-length leukotoxin instead of truncated polypeptides may allow correct folding of the toxin. This would result in internalization of the hydrophobic domains with a corresponding reduction of toxicity in *E. coli* host cells. Both polyclonal and monoclonal antibodies against native leukotoxin recognized a protein species with a size consistent with that of the intact leukotoxin in western blot analysis of cell lysates of *E. coli* harboring pSN2000. Antibodies raised against all five truncated leukotoxin polypeptides, but not the upstream polypeptide, recognized full-length recombinant leukotoxin as well.

In order to determine the prevalence and heterogeneity of leukotoxin gene in this species, 15 *F. necrophorum* strains belonging to subsp. *necrophorum* and subsp. *funduliforme* isolated from liver abscesses (opportunistic pathogen) or rumen contents (normal inhabitant) were screened for lktA by Southern blotting. Strains belonging to *F. necrophorum* subsp. *necrophorum*, irrespective of its location of isolation (liver abscess or ruminal contents) had similar hybridizing patterns. Similarly, all strains of *F. necrophorum* subsp. *funduliforme*, irrespective of the site from which it was isolated had identical hybridization patterns, but which differed from the subspecies *necrophorum* pattern. The difference in Southern blot hybridization patterns suggest that the disparity in levels of leukotoxin produced between the two subspecies may be due to differences in genetic organization of the leukotoxin locus.

We claim:

1. An isolated nucleic acid that comprises a nucleotide sequence comprising at least about 95% sequence identity with a nucleotide sequence selected from the group consisting of SEQ ID NO: 8, SEQ ID NO: 9, SEQ ID NO: 10, SEQ ID NO: 11, SEQ ID NO: 12, SEQ ID NO: 13, and SEQ ID NO: 14 said nucleotide sequence encoding a polypeptide selected from the group consisting of SEQ ID NO: 1, SEQ ID NO: 2, SEQ ID NO: 3, SEQ ID NO: 4, SEQ ID NO: 5, SEQ ID NO: 6, and SEQ ID NO: 7.

2. An expression vector that comprises the isolated nucleic acid of claim 1.

3. An isolated nucleic acid encoding a truncated protein comprising the amino acid sequence of SEQ ID NO: 2.

4. The isolated nucleic acid of claim 3 comprising the nucleotide sequence of SEQ ID NO: 9.

5. An expression vector that comprises the isolated nucleic acid of claim 3.

6. An isolated nucleic acid encoding a truncated protein comprising the amino acid sequence of SEQ ID NO: 3.

7. The isolated nucleic acid of claim 6 comprising the nucleotide sequence of SEQ ID NO: 10.

8. An expression vector that comprises the isolated nucleic acid of claim 6.

9. An isolated nucleic acid encoding a truncated protein comprising the amino acid sequence of SEQ ID NO: 4.

10. The isolated nucleic acid of claim 9 comprising the nucleotide sequence of SEQ ID NO: 11.

11. An expression vector that comprises the isolated nucleic acid of claim 9.

12. An isolated nucleic acid encoding a truncated protein comprising the amino acid sequence of SEQ ID NO: 5.

13. The isolated nucleic acid of claim 12 comprising the nucleotide sequence of SEQ ID NO: 12.

14. An expression vector that comprises the isolated nucleic acid of claim 12.

15. An isolated nucleic acid encoding a truncated protein comprising the amino acid sequence of SEQ ID NO: 6.

16. The isolated nucleic acid of claim 15 comprising the nucleotide sequence of SEQ ID NO: 13.

17. An expression vector that comprises the isolated nucleic acid of claim 15.

18. An isolated nucleic acid comprising a nucleic acid sequence selected from the group consisting of:
a nucleotide sequence having at least 95% sequence identity with a nucleic acid selected from the group consisting of SEQ ID NO: 8, SEQ ID NO: 9, SEQ ID NO: 10, SEQ ID NO: 11, SEQ ID NO: 12, SEQ ID NO: 13, and SEQ ID NO: 14.

19. An isolated nucleic acid comprising a nucleic acid sequence selected from the group consisting of a nucleotide sequence encoding a polypeptide selected from the group consisting of SEQ ID NO: 1, SEQ ID NO: 2, SEQ ID NO: 3, SEQ ID NO: 4, SEQ ID NO: 5, SEQ ID NO: 6, and SEQ ID NO: 7.

20. An expression vector that comprises the isolated nucleic acid of claim 18.

21. An expression vector that comprises the isolated nucleic acid of claim 19.

* * * * *